(12) United States Patent
Shefer

(10) Patent No.: US 12,297,438 B2
(45) Date of Patent: May 13, 2025

(54) GENE EXPRESSION ELEMENTS AND SYSTEMS AND USE THEREOF

(71) Applicant: GENENEER LTD., Shoham (IL)

(72) Inventor: Kinneret Shefer, Shoham (IL)

(73) Assignee: GENENEER LTD., Shoham (IL)

( * ) Notice: Subject to any disclaimer, the term of this patent is extended or adjusted under 35 U.S.C. 154(b) by 641 days.

(21) Appl. No.: 17/419,759

(22) PCT Filed: Jan. 1, 2020

(86) PCT No.: PCT/IL2020/050004
§ 371 (c)(1),
(2) Date: Jun. 30, 2021

(87) PCT Pub. No.: WO2020/141528
PCT Pub. Date: Jul. 9, 2020

(65) Prior Publication Data
US 2022/0064656 A1   Mar. 3, 2022

Related U.S. Application Data

(60) Provisional application No. 62/787,302, filed on Jan. 1, 2019.

(51) Int. Cl.
*C12N 15/82* (2006.01)

(52) U.S. Cl.
CPC ..... *C12N 15/8209* (2013.01); *C12N 15/8216* (2013.01); *C12N 15/8274* (2013.01); *C12N 15/8282* (2013.01); *C12N 15/8283* (2013.01); *C12N 15/8286* (2013.01)

(58) Field of Classification Search
CPC .................................................. C12N 15/8209
USPC ........................................................ 800/279
See application file for complete search history.

(56) References Cited

U.S. PATENT DOCUMENTS

| | | | |
|---|---|---|---|
| 5,034,506 | A | 7/1991 | Summerton |
| 5,235,033 | A | 8/1993 | Summerton |
| 5,384,253 | A | 1/1995 | Krzyzek |
| 9,133,477 | B2 | 9/2015 | Alphey |
| 9,273,364 | B2 | 3/2016 | Hagiwara |
| 9,399,779 | B2 | 7/2016 | Daines |
| 9,399,799 | B2 | 7/2016 | Gordon |
| 10,059,961 | B2 | 8/2018 | Alphey |
| 2009/0183269 | A1 | 7/2009 | Alphey |
| 2010/0081177 | A1 | 4/2010 | Schatz |
| 2010/0196335 | A1 | 8/2010 | Samulski |
| 2015/0056655 | A1 | 2/2015 | Aebischer-Gumy |

FOREIGN PATENT DOCUMENTS

| | | |
|---|---|---|
| GB | 2443186 A | 4/2008 |
| WO | 0018963 A1 | 4/2000 |

OTHER PUBLICATIONS

Hyvonen et al. Rna 12(8), 1569-1582 (Year: 2006).*
Ni et al. Genes & Development 21(6), 708-718 (Year: 2007).*
Hyvonen et al., Rna 12:1569-1582 (Year: 2006).*
Wang et al. Journal of Biological Chemistry 273:34623-34630 (Year: 1998).*
Ni et al. Genes & development 21:708-718 (Year: 2007).*
Hyvönen et al., (2012) Tissue-specific alternative splicing of spermidine/spermine N1-acetyltransferase. Amino Acids 42(2-3): 485-493.
Almeida and Turecki (2016) A Slice of the Suicidal Brain: What Have Postmortem Molecular Studies Taught Us? Curr Psychiatry Rep 18(11): 98; 10 pages.
Bocobza et al., (2007) Riboswitch-dependent gene regulation and its evolution in the plant kingdom. Genes Dev 21 (22): 2874-2879.
Chandler et al., (1989) Two regulatory genes of the maize anthocyanin pathway are homologous: isolation of B utilizing R genomic sequences. Plant Cell 1(12): 1175-1183.
Ebert et al., (1987) Identification of an essential upstream element in the nopaline synthase promoter by stable and transient assays. Proc Natl Acad Sci U S A 84(16): 5745-5749.
Gleba et al., (2007) Viral vectors for the expression of proteins in plants. Curr Opin Biotechnol 18(2): 134-141.
Hyvönen et al., (2006) Polyamine-regulated unproductive splicing and translation of spermidine/spermine N1-acetyltransferase. RNA 12(8): 1569-1582.
Lawton et al., (1987) Expression of a soybean β-conclycinin gene under the control of the Cauliflower Mosaic Virus 35S and 19S promoters in transformed petunia tissues. Plant Mol Biol 9(4): 315-324.
Leple et al., (1992) Transgenic poplars: expression of chimeric genes using four different constructs. Plant Cell Rep 11(3): 137-141.
Leplé et al., (2007) Downregulation of cinnamoyl-coenzyme A reductase in poplar: multiple-level phenotyping reveals effects on cell wall polymer metabolism and structure. Plant Cell 19(11): 3669-3691.
Marton et al., (2010) Nontransgenic genome modification in plant cells. Plant Physiol 154(3): 1079-1087.
Ni et al., (2007) Ultraconserved elements are associated with homeostatic control of splicing regulators by alternative splicing and nonsense-mediated decay. Genes Dev 21(6): 708-718.
Odell et al., (1985) Identification of DNA sequences required for activity of the cauliflower mosaic virus 35S promoter. Nature 313(6005): 810-812.

(Continued)

*Primary Examiner* — Li Zheng
(74) *Attorney, Agent, or Firm* — RAPHAEL BELLUM PLLC

(57) ABSTRACT

The present invention provides a versatile platform system for regulating gene expression in cells of eukaryotic organisms, including plants, algae and fungi, and mammals. A platform system of the invention includes an expression control element and expression system comprising the same. Expression control elements according to the invention can be inserted into a variety of cell types having the capability of alternative splicing and can be regulated by a polyamine or polyamine analogues. Host cells comprising the expression control elements of the invention are typically grown in a cell or tissue culture, or form part of a living plant, algae, or fungi.

19 Claims, 12 Drawing Sheets

Specification includes a Sequence Listing.

(56) References Cited

OTHER PUBLICATIONS

Pedersen et al., (1982) Cloning and sequence analysis reveal structural variation among related zein genes in maize. Cell 29(3): 1015-1026.
Potrykus (1991) Gene Transfer to Plants: Assessment of Published Approaches and Results. Annual Review of Plant Physiology and Plant Molecular Biology 42: 205-225.
Shimamoto et al., (1989) Fertile transgenic rice plants regenerated from transformed protoplasts. Nature 338: 274-276.
Tzfira et al., (2005) pSAT vectors: a modular series of plasmids for autofluorescent protein tagging and expression of multiple genes in plants. Plant Mol Biol 57(4): 503-516.
Upadhyaya et al., (2000) Agrobacterium-mediated transformation of Australian rice cultivars Jarrah and Amaroo using modified promoters and selectable markers. Australian Journal of Plant Physiology 27(3): 201-210. Abstract.
Walker et al., (1987) DNA sequences required for anaerobic expression of the maize alcohol dehydrogenase 1 gene. Proc Natl Acad Sci U S A 84(19): 6624-6628.
Wang et al., (1998) The identification of a cis-element and a trans-acting factor involved in the response to polyamines and polyamine analogues in the regulation of the human spermidine/spermine N1-acetyltransferase gene transcription. J Biol Chem 273(51): 34623-34630.
Weinmann et al., (1994) A chimeric transactivator allows tetracycline-responsive gene expression in whole plants. Plant J 5(4): 559-569.
Wu et al., (2009) Tape-*Arabidopsis* Sandwich—a simpler *Arabidopsis* protoplast isolation method. Plant Methods 5: 16; 10 pages.
Yang and Russell (1990) Maize sucrose synthase-1 promoter directs phloem cell-specific expression of Gus gene in transgenic tobacco plants. Proc Natl Acad Sci U S A 87(11): 4144-4148.

\* cited by examiner

GENE EXPRESSION ELEMENTS AND SYSTEMS AND USE THEREOF

FIELD OF THE INVENTION

The present invention relates to an expression control element and expression system comprising same, particularly to an expression control element regulated by a polyamine or polyamine analogue, host cells comprising same and methods of use thereof.

BACKGROUND OF THE INVENTION

Alternative splicing is also known as pre-mRNA splicing and involves the removal of one or more introns and ligation of the flanking exons. This reaction is catalyzed by the spliceosome, a macromolecular machine composed of five RNAs and hundreds of proteins. Alternative splicing generates multiple mRNAs from a single gene, thus increasing proteome diversity. Alternative splicing also plays a key role in the regulation of gene expression in many developmental processes ranging from sex determination to apoptosis, and defects in alternative splicing have been linked to many human disorders. One of the regulatory mechanisms surrounding pre-mRNA splicing, includes metabolites and small molecules that can bind RNA structures and directly regulate splicing. The responsive regulatory element is termed "riboswitch", with most of the riboswitches found in bacteria and typically located at the 5'-untranslated region (5'-UTR) of the main coding region of a particular mRNA. A riboswitch is a region in an mRNA molecule that can directly bind a small molecule ligand, wherein the binding of the ligand affects the gene's activity. The binding is selective through a conserved sensor domain. Upon substrate binding the conformation of a variable "expression platform" coupled to the sensor domain is changed and this can affect different modes of gene control including transcription termination, translation initiation or mRNA processing. Notably, riboswitches exert their functions without the need for protein cofactors. In most cases, they act in feedback regulation mechanisms: once the level of an end product in a metabolic pathway rises riboswitch binding occurs, triggering a repression of gene expression in the same pathway. The substrate specificity of riboswitches is extremely high, allowing them to perform their activity amid the presence of numerous related compounds. In prokaryotes, genetic control mediated by riboswitches is a prevalent phenomenon and the dozen riboswitches identified to date regulate over 3% of all bacterial genes.

Polyamines, spermidine and spermine and their precursor putrescine, are small ubiquitous organic cations that are essential for cell growth and proliferation and for the synthesis of proteins and nucleic acids. Due to their positive charge, polyamines interact with different polyanionic macromolecules such as DNA and RNA. Spermidine/spermine $N^1$-acetyltransferase (SSAT) is a eukaryotic enzyme in the inter-conversion of polyamines. The enzyme acetylates spermidine and spermine, which are then either excreted out from the cell or converted back to putrescine or spermidine, respectively, by polyamine oxidase. SSAT pre-mRNA has been recently found to undergo alternative splicing (Hyvonen M T et al., 2006. RNA 12:1569-1582).

Use of alternative splicing for controlling gene expression has been described. For example, U.S. Pat. No. 9,133,477 discloses a gene expression system capable of mediating alternative slicing in a sex-specific, stage-specific, germline-specific and tissue-specific manner. The system comprises at least one coding sequence to be expressed in an organism, and at least one promoter operably linked thereto. It further comprises at least one splice control sequence which, in cooperation with a spliceosome, mediates alternative splicing of RNA transcripts of the coding sequence. U.S. Pat. No. 9,399,799 discloses CD44 based alternative splicing constructs useful in high-throughput assays for testing the effects of compounds on splicing and for achieving targeted cell death. U.S. Pat. No. 9,273,364 discloses transgenic reporter system that reveals expression profiles and regulation mechanisms of alternative splicing in mammalian organisms. U.S. Application Publication No. 2009/0183269 discloses gene expression system using alternative splicing in insects. U.S. Application Publication No. 2010/0196335 discloses methods and compositions for regulated expressions of nucleic acid at post-transcriptional level. U.S. Application Publication No. 2015/0056655 discloses an expression construct for the expression of polypeptides in host cells using alternative splicing. The expression construct can be used for the expression of polypeptides such as antibodies, antibody fragments and bi-specific antibodies by expressing the gene products required for protein expression at the ratio leading to the highest titer or the best product quality profile.

In plants and algae, thiamine pyrophosphate (TPP)-binding riboswitch has been reported to determine mRNA transcription level by alteration of the splicing pathway. In *Arabidopsis*, TPP binding to THIAMINE C SYNTHASE (THIC) pre-mRNA engenders alternative splicing that leads to the generation of an unstable transcript, which in turn lowers TPP biosynthesis (Bocobza S et al., 2007. Genes Dev 21, 2874-2879). This mechanism has been reported to be active in the whole plant kingdom from the mosses through angiosperms.

Plants, algae and fungi are commonly used as "factories" for production of high amounts of biologically active (including therapeutic) agents, where a precise control of gene expression and thus the agent production is highly desired. Cultures of mammalian cells may also be used for production of exogenous biologically active agents. Regulation of gene expression during various developmental stages, particularly in plants, is also of high interest.

There is a recognized need for, and it would be highly advantageous to have a versatile platform system for regulating gene expression in eukaryotic cells

SUMMARY OF THE INVENTION

The present invention provides a versatile platform system for regulating gene expression in cells of eukaryotic organisms, particularly plants, algae and fungi, but also in mammals. The expression elements of the present invention can be inserted into a variety of cell types having the capability of alternative splicing. The cells are typically grown in a cell or tissue culture, and can also form part of a living plant, alga or fungus. The expression control elements of the present invention can be used to control and regulate the expression of heterologous as well as endogenous genes within cells of the target eukaryotic organism in a cost effective and reliable manner. Controlling gene expression may include increasing or decreasing the formation and/or stability of an RNA (including RNA viruses) that may be the desired end product or an RNA that leads to protein synthesis and alteration of the protein levels in the cell compared to a base line. The regulation of the expression of a transcribable polynucleotide enabled by the systems of the present invention renders the systems suitable for a wide variety of uses, from prevention of undesired expression of foreign gene(s) in transgenic organism under certain circumstances to fine tuning of the production of a desired product.

The system of the present invention is based in part on the unexpected discovery that insertion of a minimal segment of a region of the gene encoding mouse spermidine/spermine $N^1$-acetyltransferase (SSAT), comprising a polyamine (or polyamine analog) responsive sequence can effectively control splicing and expression of a polynucleotide comprising the segment in a plant cell. The present invention shows for the first time that exposing the plant cell comprising the heterologous polyamine-responsive sequence to t the polyamine analog $N^1,N^{11}$-Diethylnorspermine tetrahydrochloride resulted in increased expression of a functional splice variant compared to its expression in the absence of the analog.

The present invention discloses an artificially designed expression control element (ECE), which can be part of and regulate the expression of any polynucleotide encoding any RNA (including viral RNA) or protein of interest, in a variety of eukaryotic cells, wherein the expression can be tightly regulated by altering the level of polyamines or their analogs to which the cells are exposed.

According to one aspect, the present invention provides an isolated expression control element (ECE) comprising a polyamine or polyamine analog responsive nucleic acid sequence flanked by splice sites or variants thereof.

According to certain embodiments, the polyamine or polyamine analog responsive nucleic acid sequence comprises at least one stop codon.

According to certain embodiments, the polyamine or polyamine analog responsive nucleic acid sequence is derived from a gene encoding SSAT.

According to certain embodiments, the polyamine or polyamine analog responsive nucleic acid sequence is derived from a gene encoding mouse SSAT or a homolog thereof. According to certain embodiments, the SSAT encoding gene comprises a nucleic acid sequence having at least 85% identity to the nucleic acid sequence set forth in SEQ ID NO:1. According to certain exemplary embodiments, the SSAT encoding gene comprises the nucleic acid sequence set forth in SEQ ID NO:1.

According to certain embodiments, the polyamine or polyamine analog responsive nucleic acid sequence has at least 95% sequence identity to the nucleic acid sequence set forth in SEQ ID NO:2. According to some embodiments, the polyamine or polyamine analog responsive nucleic acid sequence consists of SEQ ID NO:2.

According to certain exemplary embodiments, the polyamine or polyamine analogue responsive nucleic acid sequence comprises the nucleic acid sequence set forth in SEQ ID NO:3. According to some embodiments, the polyamine or polyamine analog responsive nucleic acid sequence consists of SEQ ID NO:3.

According to certain embodiments, the flanking splice sites comprise a nuclei acid sequence of a splice acceptor site located 5' to the polyamine or polyamine analog responsive nucleic acid sequence and a nucleic acid sequence of a splice donor site located 3' to the polyamine or polyamine analog responsive nucleic acid sequence. 10 According to some embodiments, the splice acceptor site comprises the consecutive nucleotides CTTCAGGT (SEQ ID NO:4) or a functional variant thereof.

According to some embodiments, a mutation in SEQ ID NO:4 results in a splice acceptor site variant that reduces the splicing frequency. According to certain exemplary embodiments, the variant comprises the consecutive nucleotides CTTTAGGT (SEQ ID NO: 5). According to some embodiments, a mutation in SEQ ID NO:4 results in a splice acceptor site variant that enhances the splicing frequency. According to certain exemplary embodiments, the variant comprises the consecutive nucleotides TTGCAGGT (SEQ ID NO:6).

According to some embodiments, the splice donor site comprises the consecutive nucleotides GAGGTAAGGTCC (SEQ ID NO:7) or a functional variant thereof. According to some embodiments, a mutation in SEQ ID NO:7 results in a splice donor site variant that reduces the splicing frequency. According to certain exemplary embodiments, the variant comprises the consecutive nucleotides TAGGTAAGTTCC (SEQ ID NO:8). According to some embodiments, a mutation in SEQ ID NO:7 results in a splice donor site variant that enhances the splicing frequency. According to certain exemplary embodiments, the variant comprises the consecutive nucleotides AAGGTAAGTTCC (SEQ ID NO:9). According to additional certain exemplary embodiments, the variant comprises the consecutive sequence GAGGTAAGAGTC (SEQ ID NO:10).

According to some embodiments, the splice acceptor site comprises the consecutive nucleotides CCCACCCTTAG (SEQ ID NO:15) or a functional variant thereof. According to some embodiments, a mutation in SEQ ID NO:15 results in a splice acceptor site variant that enhances the splicing frequency. According to certain exemplary embodiments, the variant comprises the consecutive nucleotides CCCACCCGCAG (SEQ ID NO:16). According to some embodiments, a mutation in SEQ ID NO:15 results in a splice acceptor site variant that reduces the splicing frequency. According to certain exemplary embodiments, the variant comprises the consecutive nucleotides CCCCCCCT-TAG (SEQ ID NO:17).

According to some embodiments, the donor site comprises the consecutive nucleotides GGCGGTTGGTAT (SEQ ID NO:18) or a functional variant thereof. According to some embodiments, a mutation in SEQ ID NO:18 results in a splice donor site variant that enhances the splicing frequency. According to certain exemplary embodiments, the variant comprises the consecutive nucleotides AAGGGTTGGTAT (SEQ ID NO:19). According to some embodiments, a mutation in SEQ ID NO:18 results in a splice donor site variant that reduces the splicing frequency. According to certain exemplary embodiments, the variant comprises the consecutive nucleotides GGCGGTTGTTAT (SEQ ID NO:20).

According to some embodiments, the ECE splice acceptor site comprises the consecutive nucleotides ATAGTTACAG (SEQ ID NO:32) or a functional variant thereof. According to some embodiments, a mutation in SEQ ID NO:32 results in a splice acceptor site variant that enhances the splicing frequency. According to certain exemplary embodiments, the variant comprises the consecutive nucleotides TTTTTGCAG (SEQ ID NO:33). According to some embodiments, a mutation in SEQ ID NO: 32 results in a splice acceptor site variant that reduces the splicing frequency. According to certain exemplary embodiments, the variant comprises the consecutive nucleotides AGTTATAG (SEQ ID NO:34).

According to some embodiments, the donor site comprises the consecutive nucleotides GAGGGTAAATTT (SEQ ID NO:35) or a functional variant thereof. According to some embodiments, a mutation in SEQ ID NO:35 results in a splice donor site variant that enhances the splicing frequency. According to certain exemplary embodiments, the variant comprises the consecutive nucleotides AAGGTAAGTTT (SEQ ID NO:36). According to some embodiments, a mutation in SEQ ID NO:35 results in a splice donor site variant that reduces the splicing frequency. According to certain exemplary embodiments, the variant comprises the consecutive nucleotides AAAGTAAATTT (SEQ ID NO:37).

According to certain embodiments, the splice acceptor site comprises consecutive nucleotide sequence selected from the group consisting of SEQ ID NO:4, SEQ ID NO: 5, SEQ ID NO:6, SEQ ID NO:15, SEQ UD NO: 16, SEQ ID NO:17, SEQ ID NO: 32, SEQ ID NO:33, SEQ ID NO:34 and any combination thereof. Each possibility represents a separate embodiment of the present invention.

According to certain embodiments, the splice donor site comprises consecutive nucleotide sequence selected from the group consisting of SEQ ID NO:7, SEQ ID NO: 8, SEQ ID NO:9, SEQ ID NO:10, SEQ ID NO:18, SEQ ID NO:19, SEQ ID NO:20, SEQ ID NO:35, SEQ ID NO:6, SEQ ID NO:37 and any combination thereof. Each possibility represents a separate embodiment of the present invention.

According to certain embodiments, the isolated ECE further comprises at least one intron sequence. According to certain embodiments, the intron sequence comprises at least 10 nucleotides. According to some embodiments, the intron sequence comprises at least 20, at least 30, at least 40, at least 50 or at least 60 nucleotides. According to certain exemplary embodiments, the intron sequence comprises from about 40 nucleotides to about 150 nucleotides.

According to certain embodiments, the at least one intron sequence is flanking each of the splice sites or the variants thereof. The intron sequence flanking the splice donor site and the splice acceptor site can be the same or different. According to certain embodiments, the intron sequence can be derived from naturally occurring introns that are alternately spliced, and from constitutively spliced introns.

According to certain embodiments, the at least one intron sequence comprises a nucleic acids sequence of an intron of a gene encoding SSAT, a homolog or a variant thereof. According to certain exemplary embodiments, the gene encoding SSAT comprises a nucleic acid sequence having at least 85% identity to the nucleic acid sequence set forth in SEQ ID NO:1.

According to certain embodiments, the ECE comprises an intron sequence located 5' to the splice acceptor site. According to certain embodiments, the intron sequence comprises a branch point. According to certain exemplary embodiments, the branch point comprises the consecutive nucleotides CTTTAAT (SEQ ID NO:11) or a functional variant thereof. According to some embodiments, a mutation in the branch point sequence reduces the splicing frequency at the splice acceptor site. According to certain exemplary embodiments, the variant comprises the consecutive nucleotides CTTTTAT (SEQ ID NO:12). According to some embodiments, a mutation in the branch point enhances the splicing frequency at the splice acceptor site. According to certain exemplary embodiments, the variant comprises the consecutive nucleotides CTCTTAT (SEQ ID NO:13).

According to certain exemplary embodiments, the isolated expression control element comprises a nucleic acid sequence selected from the group consisting of SEQ ID NO: 21, SEQ ID NO:26, SEQ ID NO:27, SEQ ID NO:51 and SEQ ID NO:58. Each possibility represents a separate embodiment of the present invention.

According to certain exemplary embodiments, the isolated expression control element comprises the nucleic acid sequence set forth in SEQ ID NO:21.

According to certain exemplary embodiments, the isolated expression control element comprises the nucleic acid sequence set forth in SEQ ID NO:26.

According to certain embodiments, each of the introns flanking the splice sites comprises a chimeric combination of intron nucleic acid sequences. According to certain embodiments, the chimeric combination comprises an intron sequence derived from a gene encoding SSAT having the nucleic acid sequence set forth in SEQ ID NO:1 or a homolog thereof and an intron sequence derived from a gene encoding beta-globin a nucleic acid sequence at least 85% identical to the nucleic acid sequence set forth in SEQ ID NO:14.

According to certain exemplary embodiments, the intron comprises the nucleic acid sequence set forth in SEQ ID NO:22 flanked by the nucleic acid sequence set forth in SEQ ID NO:23 derived from globin. According to theses embodiments, the intron is located 5' to the splice acceptor site. According to additional certain exemplary embodiments, the intron comprises the nucleic acid sequence set forth in SEQ ID NO: 24 flanked by the nucleic acid sequence set forth in SEQ ID NO:25. According to theses embodiments, the intron is located 3' to the splice donor site.

According to further certain embodiments, each of the introns flanking the splice sites comprises a combination of an intron sequence derived from a gene encoding SSAT having the nucleic acid sequence set forth in SEQ ID NO:1 or a homolog thereof and an intron sequence derived from a gene encoding GUS comprising the nucleic acid sequence set forth in SEQ ID NO:29 or a homolog thereof. According to certain exemplary embodiments, the intron comprises the nucleic acid sequence set forth in SEQ ID NO:22 flanked by the nucleic acid sequence set forth in SEQ ID NO:30. According to theses embodiments, the intron is located 5' to the splice acceptor site.

According to additional certain exemplary embodiments, the intron comprises the nucleic acid sequence set forth in SEQ ID NO:24 flanked by the nucleic acid sequence set forth in SEQ ID NO:31. According to theses embodiments, the intron is located 3' to the splice donor site.

According to a further aspect, the present invention provides a host cell comprising an expression control element (ECE) located within a transcribable polynucleotide of the host cell, wherein the ECE comprises a polyamine or polyamine analog responsive nucleic acid sequence flanked by splice sites or variants thereof.

The polyamine or polyamine analog responsive nucleic acid sequence, and the splice sites and variants thereof are as described hereinabove.

According to certain embodiments, the ECE further comprises at least one intron sequence as described hereinabove.

According to alternative embodiments, the ECE is located within an intron of an endogenous transcribable polynucleotide of the host cell.

According to certain embodiments the ECE is capable of mediating alternative splicing of RNA transcripts of the transcribable polynucleotide in cooperation with a spliceosome in response to the level of polyamine or analog thereof in the host cell.

According to additional aspect, the present invention provides a polynucleotide expression system comprising at least one promoter operably linked to at least one transcribable polynucleotide to be expressed in a host cell, the transcribable polynucleotide comprising an expression control element, wherein the expression control element comprises a polyamine or polyamine analogue responsive nucleic acid sequence flanked by splice sites or variants thereof.

The polyamine or polyamine analog responsive nucleic acid sequence and the splice sites and variants thereof are as described hereinabove.

According to certain embodiments, the ECE further comprises at least one intron sequence as described hereinabove.

According to yet another aspect, the present invention provides a host cell comprising at least one heterologous polynucleotide expression system comprising at least one promoter operably linked to at least one transcribable polynucleotide to be expressed in the host cell, the transcribable polynucleotide comprising an expression control element (ECE), wherein the ECE comprises a polyamine or polyamine analog responsive nucleic acid sequence flanked by splice sites or variants thereof.

The ECE elements are as described herein above.

According to certain embodiments the ECE is capable of mediating alternative splicing of RNA transcripts of the transcribable polynucleotide in cooperation with a spliceosome in response to the level of polyamine or analog thereof in the host cell.

According to certain embodiments, the host cell comprising the heterologous ECE or polynucleotide expression system is selected from the group consisting of a plant cell, an algal cell, a fungus cell, a mammalian cell and a fish cell. Each possibility represents a separate embodiment of the present invention.

According to certain embodiments, a plurality of the host cells forms a cell culture or a tissue culture.

According to certain embodiments, when the host cell is a plant, alga or a fungus cell the host cell or a plurality of the host cells can form part of an intact plant, alga or fungus or a part thereof, respectively.

Thus, according to additional aspect, the present invention provides a plant, an alga or a fungus comprising at least one cell comprising the ECE or the polynucleotide expression system of the present invention.

The promoter operably linked to the transcribable polynucleotide can be any promoter active in the host cell. According to certain embodiments, the promoter is selected from the group consisting of a constitutive promoter, an inducible promoter and development stage specific promoter. Each possibility represents a separate embodiment of the present invention. When the host cell is a plant cell forming part of an intact plant or a plant organ the promoter can be a tissue specific promoter.

Advantageously, the expression control element of the present invention mediates alternative splicing of RNA transcripts of the transcribable polynucleotide in dependence with the level of polyamines or polyamine analogs in the host cell. Elevating the polyamine level above the basal endogenous cell level, and/or exposing the cell to effective amount of polyamine analog(s), enhances the frequency of the polyamine or polyamine analog responsive sequence exclusion (splicing out) from the transcript of the transcribable polynucleotide. Basal or reduced levels of endogenous polyamines enhance retention of the responsive sequence within the transcribable polynucleotide.

According to certain exemplary embodiments, exclusion (splicing out) of the polyamine or polyamine analog responsive sequence from the transcript of the transcribable polynucleotide results in expression of a functional transcript of said transcribable polynucleotide. According to these embodiments, retention of the polyamine or polyamine analog responsive sequence within the transcribable polynucleotide results in a non-functional transcript. According to certain embodiments, the non-functional transcript is amenable to degradation by nonsense-mediated decay (NMD) system pathway.

According to other embodiments, exclusion of the polyamine or polyamine analog responsive sequence from the transcribable polynucleotide results in expression of a non-functional transcript of the transcribable polynucleotide. According to these embodiments, retention of the responsive sequence within the transcribable polynucleotide results in a functional transcript of the transcribable polynucleotide.

According to certain embodiments, the transcribable polynucleotide comprises a polynucleotide encoding a product selected from the group consisting of an RNA molecule and a protein. Each possibility represents a separate embodiment of the present invention. According to some embodiments, the RNA molecule is a viral RNA.

According to some embodiments, the polynucleotide expression system further comprises at least one additional regulatory element operable in the host cell. According to certain embodiments, the regulatory element is selected from the group consisting of an enhancer, a terminator, a transcriptional activator and a combination thereof.

The transcribable polynucleotide of the expression system of the present invention can encode for any RNA molecule or protein of interest. According to certain embodiments, the expressed RNA molecule or protein is endogenous to the host cell. According to other embodiments, the expressed RNA molecule or protein is heterologous to the host cell.

According to some embodiments, the functional transcript or protein product encoded by same is a regulatory element According to certain embodiments, the regulatory element is selected from the group consisting of transcription control factor, translation control factor and the like. The regulatory element can have a positive or negative regulatory effect on a gene comprising said regulatory sequence recognition sequence. Each possibility represents a separate embodiment of the present invention.

According to some embodiments, the functional spliced RNA molecule encodes a functional protein product. Any protein can be encoded by the coding sequence of the expression system of the present invention, including proteins that have beneficial effects, regulatory effects, and deleterious effects on the cell in which they are expressed or that are inert to the cell in which they are expressed. The later protein type is typically expressed when the cell is used as a "factory" for protein synthesis. According to certain embodiments, the produced proteins have therapeutic or industrial use.

The expression control element of the present invention may have a significant beneficial use when expressed in plants comprising heterologous genes encoding products that confer to the plant resistance to herbicides, pesticides, and/or fungicides. Constitutive expression of such products may have deleterious effects to the plant itself; more importantly, such constitutive expression may be harmful to the environment, particularly by "leakage" of the resistance-conferring genes to relative wild type species. The expression system of the invention enables to synchronize expression of the resistance-conferring genes with the application of herbicides, pesticides, and/or fungicides by co-application of polyamine and/or analog thereof according to the teachings of the present invention.

Thus, according to certain exemplary embodiments, when the cell comprising the polynucleotide expression system is a plant cell, the transcribable polynucleotide encodes a product conferring resistance to at least one of herbicides, pesticides, and fungicides. Each possibility represents a separate embodiment of the present invention.

According to certain embodiments, the transcribable polynucleotide encodes a product conferring resistance to at least one herbicide. According to some embodiments, the herbicide is selected from the group consisting of, but not limited to, glyphosate, mesotrione, bialaphos atrazine, metolachlor, paraquat clopyralid, fluazifop, fluroxypyr, imazapyr, imazapic, imazamox, linuron, MCPA (2-methyl-4-chloro-phenoxyacetic acid), pendimethalin, and triclopyr.

According to certain exemplary embodiments, the herbicide is glyphosate and the transcribable polynucleotide encodes a glyphosate-resistant enolpyruvylshikimate 3-phosphate synthase (EPSPS).

According to these embodiments, exposing the plant to cells to polyamine and/or analog thereof results in the expression of functional resistance-conferring gene.

According to some embodiments, the functional spliced RNA molecule encodes a product comprising functional RNA and protein that can serve as a functional unit such as a virus that can infect other cells and therefore allow the expression of the system in the infected cells.

According to certain embodiments, the expression control element is located between two exons of the transcribable polynucleotide.

According to certain embodiments, the expression control element is located within an intron of the transcribable polynucleotide.

According to certain embodiments, the expression control element is located within an exon of the transcribable polynucleotide.

According to certain embodiments, the expression control element is located between regulatory sequence (such as promoter or terminator) and coding sequence of the transcribable polynucleotide.

According to certain exemplary embodiments the expression control element is located between the promoter and the coding sequence of the transcribable polynucleotide. According to some embodiments, the expression control element is located between the ATG start codon and the coding sequence of the transcribable polynucleotide.

According to additional exemplary embodiments, the expression control element is located between the coding sequence of the transcribable polynucleotide and a terminator sequence.

The components of the expression control element are as described hereinabove.

According to certain embodiments, wherein the expression control element of the system of the present invention comprises an intron, the intron comprises the nucleic acid sequence selected from the group consisting of SEQ ID NO:22; SEQ ID NO:23; SEQ ID NO:30 and a combination thereof. According to these embodiments, the intron is located 5' to the acceptor splice site. Each possibility represents a separate embodiment of the present invention.

According to certain embodiments, wherein the expression control element of the system of the present invention comprises an intron, the intron comprises the nucleic acid sequence selected from the group consisting of SEQ ID NO:24; SEQ ID NO:25; SEQ ID NO:31 and a combination thereof. According to these embodiments, the intron is located 3' to the donor splice site. Each possibility represents a separate embodiment of the present invention.

According to some embodiments, the expression system of the present invention comprises an expression control element having a nucleic acid sequence set forth in any one of SEQ ID NO:21, SEQ ID NO:26, SEQ ID NO:27, SEQ ID NO: 51 and SEQ ID NO: 58. According to some embodiments, the expression system of the present invention comprises an expression control element consisting of a nucleic acid sequence set forth in any one of SEQ ID NO:21, SEQ ID NO:26, SEQ ID NO:27, SEQ ID NO: 51 and SEQ ID NO:58. Each possibility represents a separate embodiment of the present invention.

Advantageously, the expression control element of the expression system of the present invention comprises a nucleic acid sequence responsive to the level of polyamines or polyamine analogs in the cell. Thus, the product expressed by the transcribable polynucleotide depends on the presence, absence, or the amount of the regulating polyamine or analog thereof to which the cell comprising the system is exposed. Product expression may be regulated by the specific design of the expression control element and by tuning the amounts of polyamines or analogs thereof to which the cells are exposed.

Regulation of product expression can be "on/off" or enhanced/reduced kind of regulation.

According to another aspect, the present invention provides a method for regulating the expression of a transcribable polynucleotide within a host cell, the method comprises transforming into the host cell at least one polynucleotide comprising the expression control element (ECE) or the expression system of the present invention and regulating the amount of polyamine or analog thereof to which said host cell is exposed.

According to some embodiments, the transcribable polynucleotide forming part of the expression system is a sequence endogenous to the host cell. According to other embodiments, the transcribable polynucleotide forming part of the expression system is a sequence heterogonous to the host cell.

According to certain embodiments, the method further comprises exposing the cell to an effective amount of polyamine or analog thereof, thereby inducing exclusion of the polyamine or polyamine analog-responsive sequence from the transcript of the coding sequence. According to certain embodiments, exclusion of the exon results in a functional transcript of the transcribable polynucleotide. According to other embodiments, exclusion of the exon results in a non-functional transcript of the transcribable polynucleotide.

According to certain embodiments, an effective amount of the polyamine or analog ligand refers to an amount which is above the basal level of endogenous polyamines with the host cell and/or an amount of polyamine or analogs thereof which increases splicing out of the polyamine or polyamine analog-responsive sequence present within the expression element of the system of the invention.

The level of polyamine or analog thereof to which the host cell comprising the expression system of the invention is exposed to can be manipulated by various compositions and methods as are known to a person skilled in the Art.

According to certain embodiments, the polyamine and/or analog thereof is exogenous to the cell. According to these embodiments, application can be performed by incubating, immersing, suspending, spraying, dipping or otherwise covering the cell, cell culture, tissue culture, plant, alga or fungus with the polyamine or analog thereof. When the cell forms part of an intact plant, the polyamine or analog thereof can also be applied to the plant roots, particularly by exposing the roots to a solution comprising the polyamine and/or polyamine analog. According to certain exemplary embodiments, the exogenous polyamine or analog thereof is applied within a composition compatible to plants and/or algae and/or fungi.

According to certain embodiments, the polyamine analog is any linear carbon chain with at list 5 carbon atoms.

According to certain embodiments, the polyamine analog is N-diethylated polyamine analog. According to some embodiments, the polyamine analog is selected from the group consisting of, but not limited to, $N^1,N^{11}$-diethylnorspermine (DENSpm, also known as N,N'-bis [3-(Ethylamino) propyl]-1,3-propanediamine tetrahydrochloride); $N^1,N^{11}$-Diethylnorspermine tetrahydrochloride (BENZ); N1,N7-Diethylnorspermidine (DENSpd); N1,N12-diethylspermine (DESpm); Polyethylenimine (PEI); spermine and spermidine.

According to certain embodiments, the polyamine is endogenous to the eukaryotic cell. According to these embodiments, the level of the endogenous polyamines can be manipulated by various reagents or molecules, depending on the origin of the cell.

According to certain exemplary embodiments, difluoromethylornithine (DFMO), an irreversible inhibitor of the rate-controlling enzyme in the biosynthesis of putrescine and spermidine, ornithine decarboxylase (ODC), can be used to reduce the level of the host cell endogenous polyamine levels.

The presence of a promoter operably linked to the transcribable polynucleotide of the invention enables additional regulation of expression of the coding sequence. According to certain embodiments, the promoter is selected from the group consisting of a constitutive promoter, an inducible promoter and a tissue specific promoter. A person skilled in the Art knows to the select a suitable promoter according to the type, intended function and/or use of the encoded product as well as the type of the eukaryotic cell comprising the expression system of the invention.

According to certain embodiments, the method comprises transforming the expression system to a plurality of cells. According to some embodiments, the plurality of cells forms part of a cell culture or a tissue culture. According to some embodiments, the cell is of a eukaryotic organism selected from the group consisting of a plant, an alga and a fungus and the plurality of transformed cells form part of a plant, an alga and a fungus.

The products of the transcribable polynucleotide are as described hereinabove. According to certain embodiments, the encoded product is an RNA molecule. According to other embodiments, the encoded product is a protein. According to other embodiments, the encoded product is an RNA and proteins complex.

According to certain embodiments, the method comprising (i) transforming into at least one cell of a plant at least one polynucleotide expression system comprising at least one promoter operably linked to at least one transcribable polynucleotide, wherein the transcribable polynucleotide encodes a product conferring resistance to at least one of herbicide, pesticide, and fungicide; (ii) exposing the plant or parts thereof to an effective amount of polyamine or analog thereof; and (iii) applying to the plant an effective amount of at least one of herbicide, pesticide and fungicide.

According to certain exemplary embodiments, exposing the plant or parts thereof to an effective amount of polyamine or analog thereof results in slicing out of the polyamine/polyamine analog responsive nucleic acid sequence and the production of functional product conferring resistance to the at least one of herbicide, pesticide, and fungicide.

According to certain embodiments, the transcribable polynucleotide encodes a product conferring resistance to herbicide. According to some embodiments, the herbicide is selected from the group consisting of glyphosate, mesotrione, bialaphos atrazine, metolachlor, paraquat clopyralid, fluazifop, fluroxypyr, imazapyr, imazapic, imazamox, linuron, MCPA (2-methyl-4-chlorophenoxyacetic acid), pendimethalin, triclopyr.

According to certain exemplary embodiments, the herbicide is glyphosate. According to these embodiments, the transcribable polynucleotide encodes a glyphosate resistant EPSPS and the method comprises applying to the plant an effective amount of glyphosate. According to these embodiments, regulating the amount of polyamine or analog.

According to yet additional aspect, the present invention provides a method for regulating the expression of an endogenous transcribable polynucleotide within a host cell, the method comprises transforming into the cell the expression control element of the present invention.

According to certain embodiments, the method further comprises exposing the cell to an effective amount of polyamine or analog thereof, thereby inducing exclusion of the polyamine or polyamine analog-responsive nucleic acid sequence from the transcript of the transcribable polynucleotide. According to certain embodiments, exclusion of the polyamine or polyamine analog-responsive nucleic acid sequence results in a functional transcript of the transcribable polynucleotide. According to other embodiments, exclusion of the polyamine or polyamine analog-responsive nucleic acid sequence results in a non-functional transcript of the coding sequence.

Methods for insertion an exogenous polynucleotide into a pre-determined region within endogenous polynucleotide of a host cell are constantly developed and improved and become available to the skilled Artisan. The expression control element of the invention can thus be inserted into specific regions of the transcribable polynucleotide the expression of which is to be regulated.

According to certain embodiments, the expression control element is transformed into an intron of the transcribable polynucleotide.

According to other embodiments, the expression control element is transformed into between two exons of the coding sequence.

According to yet additional embodiments, the expression control element is transformed into an exon of the transcribable polynucleotide.

According to certain embodiments, the expression control element is transformed into between the promoter and the coding sequence of the transcribable polynucleotide. According to some embodiments, the expression control element is transformed into between the ATG start codon and the coding sequence of the transcribable polynucleotide.

According to certain embodiments, the expression control element is transformed into between the coding sequence of the transcribable polynucleotide and a terminator sequence.

It is to be understood explicitly that the scope of the present invention encompasses homologs, analogs, variants and derivatives, including shorter and longer polypeptides, proteins and polynucleotides, as well as polypeptide, protein and polynucleotide analogs with one or more amino acid or nucleic acid substitution, as well as amino acid or nucleic acid derivatives, non-natural amino or nucleic acids and synthetic amino or nucleic acids as are known in the art, with the stipulation that these variants and modifications must preserve the capacity of expression regulated by polyamine or analog thereof according to the teachings of the present invention.

It is to be understood that any combination of each of the aspects and the embodiments disclosed herein is explicitly encompassed within the disclosure of the present invention.

Other objects, features and advantages of the present invention will become clear from the following description and drawings.

BRIEF DESCRIPTION OF THE FIGURES

FIG. 2 demonstrates BENZ-depended GUS expression in *Nicotiana benthamina* leaf discs transfected with GUS (β-glucuronidase) encoding gene comprising within its intron the expression control element of the invention.

DETAILED DESCRIPTION OF THE INVENTION

Figure 1:
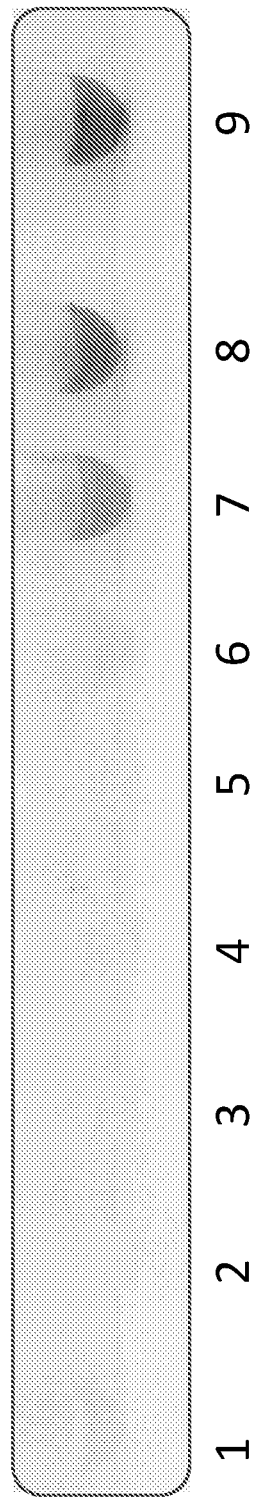
FIG. 1 demonstrates BENZ-depended GUS expression in *Arabidopsis thaliana* protoplasts transformed with GUS (β-glucuronidase) encoding gene comprising within its intron the expression control element of the invention. Blue color spots/area is indicated by arrows.

The present invention provides a platform system for controlling gene expression in a variety of eukaryotic cell types capable of mediating alternative slicing. The system of the present invention provides versatile options of use, which can be adapted to the cell type or organism in which it is expressed, the desired expressed product and the desired degree of expression control. The present invention further provides host cells comprising the systems of the present invention as well as intact plants, algae or fungi comprising same.

Definitions

The terms "comprise", "comprising", "includes", "including", "having" and their conjugates mean "including but not limited to".

As used herein, the singular form "a", "an" and "the" include plural references unless the context clearly dictates otherwise. For example, the term "a compound" or "at least one compound" may include a plurality of compounds, including mixtures thereof.

When reference is made to particular sequence or sequence ID NO., such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

As used herein, the terms "Spermidine/spermine $N^1$-acetyltransferase" and "SSAT" refer to an enzyme mediating the $N^1$-acetylation of spermidine or spermine. The SSAT enzyme sequence is highly conserved in a variety of species (FIG. 7). According to certain exemplary embodiments, the gene encoding SSAT comprises a nucleic acid sequence having at least 85% identity to SSAT of murine origin having the nucleic acid sequence set forth in SEQ ID NO:1. According to certain embodiments, the murine SSAT protein comprises the amino acid sequence set forth in SEQ ID NO: 28.

As used herein, the terms "sequence identity" or "identity" in the context of two nucleic acid or polypeptide sequences includes reference to the residues in the two sequences which are the same when aligned. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are considered to have "sequence similarity" or "similarity".

Identity can be determined using any homology comparison software, including for example, the BlastN software of the National Center of Biotechnology Information (NCBI) such as by using default parameters.

According to some embodiments of the invention, the identity is a global identity, i.e., an identity over the entire nucleic acid sequences or the amino acid sequences.

According to some embodiments of the invention, the term "homology" or "homologous" refers to identity of two or more nucleic acid sequences; or identity of two or more amino acid sequences; or the identity of an amino acid sequence to one or more nucleic acid sequence.

According to some embodiments of the invention, the homology is a global homology, i.e., a homology over the entire nucleic acid or amino acid sequences.

The degree of homology or identity between two or more sequences can be determined using various known sequence comparison tools.

The terms "splice donor site" and "5' splice site" are used herein interchangeably and refer to the splicing recognition site at the 5' end of an intron. The terms "splice acceptor site" and "3' splice site" are used herein interchangeably and refer to the splicing recognition site at the 3' end of an intron.

The term "derived" as used herein with regard to a gene refers to a sequence having homology to a part of that gene. According to certain exemplary embodiments, the polyamine or polyamine analogue-responsive nucleic acid sequence forming part of the expression control element of the present invention is derived from a gene encoding murine SSAT or a homolog thereof.

The term "coding sequence" as used herein refers to a sequence of Deoxyribonucleic acid (DNA) bases necessary for the production of RNA. According to certain exemplary embodiments of the present invention the coding sequence comprises at least one intron. The end product of the coding sequence according to the teachings of the present invention can be RNA or a protein. The RNA can be a functional transcript, including, but not limited to, RNA inhibitory molecule (e.g. dsRNA, antisense), protein encoding RNA, and viral RNA; or a non-functional transcript. The production of functional or non-functional transcript depends on splicing of the pre-RNA transcribed from the coding sequence, which in turn depends on the amount of polyamine or analog thereof reaching the expression system comprising the coding sequence.

The terms "expression system" and "polynucleotide expression system" are used herein interchangeably and refer to an artificially assembled or isolated nucleic acid molecule which includes the coding sequence encoding the product of interest and is assembled such that the product can be expressed. The system may further include a marker gene which in some cases can encode a protein of interest. The expression system further comprising appropriate regulatory sequences operably linked to the coding sequence. It should be appreciated that the inclusion of regulatory sequences in the system of the invention is optional, for example, such sequences may not be required in situations where the regulatory sequences of a host cell are to be used and the expression system is introduced into the host cell genome to be operable by the regulatory elements of the host cell.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation.

The term "cell" is defined herein as to comprise any type of eukaryotic cell capable of RNA splicing, isolated or not, cultured or not, differentiated or not, and comprising also higher-level organizations of cells such as tissues, organs, calli, organisms or parts thereof. Exemplary cells include, but are not limited to: plant cells, algal cell, fungal cells and mammalian cells, including human cells and animal cells.

The terms "polyamine-responsive nucleic acid sequence", "polyamine or polyamine analogue responsive nucleic acid sequence", "polyamine or polyamine analogue responsive sequence" and "polyamine or polyamine analogue responsive exon" are used herein interchangeably and refer to any sequence that is spliced in (i.e. retain) when polyamine levels in the cell are below a threshold and spliced out when polyamine levels are above a predetermined threshold. Examples of such sequences include the 110 bp exon derived from Spermidine/spermine $N^1$-acetyltransferase (SSAT) and homologues thereof as well as sequences capable of binding a polyamine and/or forming one secondary structure in the presence of a polyamine and another in the absence of the polyamine.

Polyamines, spermidine and spermine and their precursor putrescine, are small ubiquitous organic cations that are essential for cell growth and proliferation and for the synthesis of proteins and nucleic acids. Due to their positive charge, polyamines interact with different polyanionic macromolecules such as DNA and RNA. Spermidine/spermine $N^1$-acetyltransferase (SSAT) is a eukaryotic rate-controlling enzyme in the inter-conversion of polyamines. The enzyme acetylates spermidine and spermine, which are then either excreted out from the cell or converted back to putrescine or spermidine, respectively, by polyamine oxidase. SSAT pre-mRNA has been recently found to undergo alternative splicing to yield, along with normal SSAT mRNA, a longer variant (SSAT-X) by insertion of an additional 110-bp exon between exons 3 and 4. The exon inclusion introduces three in-frame premature termination codons (PTC). It has been shown that alterations in the intracellular polyamine level results in a change in the relative abundance of SSAT transcripts. Addition of polyamines or their N-diethylated analogs reduced the amount of the variant transcript, whereas polyamine depletion enhanced the exon inclusion. It was further shown that the variant transcript was degraded by nonsense-mediated mRNA decay (NMD) (Hyvonen M T et al., 2006. RNA 12:1569-1582).

Experiments conducted by the present inventor have shown for the first time that the 110 bp exon isolated from Spermidine/spermine $N^1$-acetyltransferase (SSAT) maintains its polyamine-responsive splicing behavior when inserted into introns of heterologous genes (see Examples section) and that this activity can be induced in organisms that lack SSAT such as plants.

Thus, according to one aspect, the present invention provides an isolated polynucleotide that functions as an expression control element (ECE). The ECE comprises a polyamine/polyamine analogue-responsive nucleic acid sequence (also referred to herein as "polyamine or polyamine analogue responsive exon") flanked by splice sites.

According to certain embodiments, the polyamine or polyamine analogue responsive nucleic acid sequence comprises at least one stop codon.

According to certain embodiments, the polyamine or polyamine analogue responsive nucleic acid sequence is derived from a gene encoding SSAT.

According to certain embodiments, the polyamine or polyamine analogue responsive nucleic acid sequence is derived from a gene encoding mouse SSAT or a homolog thereof. According to certain embodiments, the SSAT encoding gene comprises a nucleic acid sequence having at least 85%, at least 86%, at least 87%, at least 88%, at least 89%, at least 89%, at least 90%, at least 91%, at least 92%, at least 93%, at least 94%, at least 95%, at least 96%, at least 97%, at least 98%, at least 99% or 100% identity to the nucleic acid sequence set forth in SEQ ID NO:1. According to certain exemplary embodiments, the SSAT encoding gene comprises the nucleic acid sequence set forth in SEQ ID NO:1.

According to certain embodiments, the polyamine or polyamine analogue responsive nucleic acid sequence has at least 95% sequence identity to the nucleic acid sequence set forth in SEQ ID NO:2. According to certain embodiments, the polyamine or polyamine analogue responsive nucleic acid sequence has at least 96%, at least 97%, at least 98%, at least 99% or 100% sequence identity to the nucleic acids sequence set forth in SEQ ID NO:2. According to some embodiments, the polyamine or polyamine analogue responsive nucleic acid sequence consists of SEQ ID NO:2.

According to certain exemplary embodiments, the polyamine or polyamine analogue responsive nucleic acid sequence comprises the nucleic acid sequence set forth in SEQ ID NO:3. According to some embodiments, the polyamine or polyamine analogue responsive nucleic acid sequence consists of SEQ ID NO:3.

According to certain embodiments, the flanking splice sites comprise a nuclei acid sequence of a splice acceptor site located 5' to the polyamine or polyamine analogue responsive nucleic acid sequence and a nuclei acid sequence of a splice donor site located 3' to the polyamine or polyamine analogue responsive nucleic acid sequence.

According to certain embodiments, the isolated ECE further comprises at least one intron sequence. According to certain embodiments, the intron sequence comprises at least 10 nucleotides. According to some embodiments, the intron sequence comprises at least 20, at least 30, at least 40, at least 50 or at least 60 nucleotides. According to certain exemplary embodiments, the intron sequence comprises from about 40 nucleotides to about 150 nucleotides.

According to certain exemplary embodiments, the isolated polynucleotide of the present invention comprises in a 5' to 3' direction: a first splice donor site; a first flanking intron sequence comprising at least 10 bases; a first splice acceptor site; a polyamine or polyamine analogue responsive exon; a second splice donor site; a second flanking intron comprising at least 10 bases; and a second splice acceptor site.

Figure 8:
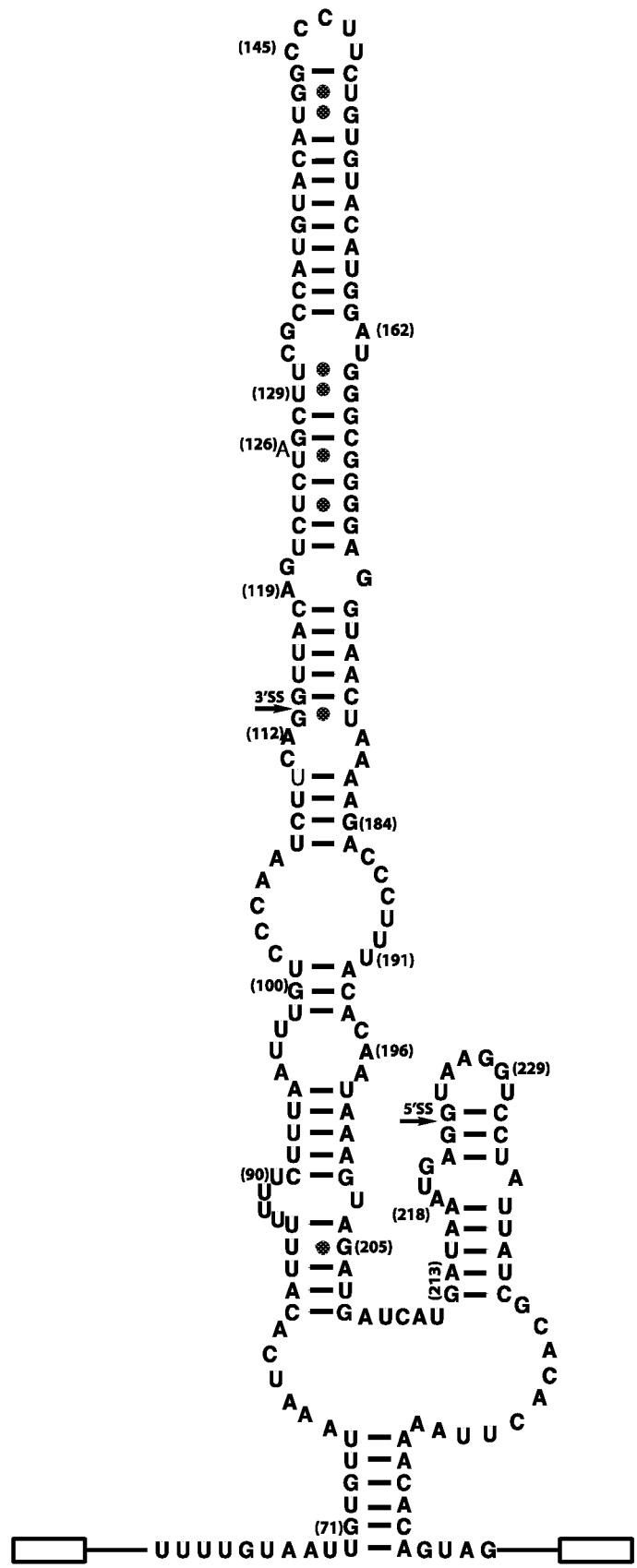
FIG. 8 represents the predicted stem loop structures (mFold) of the ECE and its flanking intronic sequence

Without wishing to be bound by any specific theory or mechanism of action, the polyamine/polyamine analog induced splicing regulation is associated with the formation of a stem loop structure of the ECE (FIG. 8) in the presence of the polyamine/polyamine analog.

According to additional aspect, the present invention provides a polynucleotide expression system comprising at least one promoter operably linked to at least one transcribable polynucleotide to be expressed in a host cell, the transcribable polynucleotide comprising an expression control element, wherein the expression control element an expression control element, wherein the expression control element comprises a polyamine or polyamine analogue responsive nucleic acid sequence flanked by splice sites or variants thereof.

The polyamine or polyamine analogue responsive nucleic acid sequence and the splice sites and variants thereof are as described hereinabove.

According to certain embodiments, the ECE further comprises at least one intron sequence as described hereinabove.

According to yet another aspect, the present invention provides a host cell comprising the heterologous ECE or the expression system comprising same according to the teachings of the present invention. The host cell is selected from the group consisting of a plant cell, an algal cell, a fungal cell, and a mammalian cell. Each possibility represents a separate embodiment of the present invention.

The present invention also encompasses a plant, an alga or a fungus comprising at least one cell comprising the heterologous ECE or the expression system comprising same according to the teachings of the present invention.

According to another aspect, the present invention provides a method for regulating the expression of a transcribable polynucleotide within a host cell, comprising transforming into the host cell at least one polynucleotide comprising the ECE or the expression system of the present invention and regulating the amount of polyamine or analogue thereof to which the host cell is exposed.

The ECE or expression system of the present invention can be transformed to any eukaryotic cell in which splicing can take place. Recombinant expression is usefully accomplished using a vector, such as a plasmid. As used herein, vector refers to any carrier containing exogenous DNA. Thus, vectors are agents that transport the exogenous nucleic acid into a cell without degradation yielding expression of the nucleic acid in the cells into which it is delivered. Vectors include but are not limited to plasmids, viral nucleic acids, viruses, phage nucleic acids, phages, cosminds, and artificial chromosomes. The vectors can be used, for example, in a variety of in vivo and in vitro situation. For example PZP or pSAT plasmids can be used as described in Tzfira et al (Tzfira T et al Plant Mol Biol. 2005. 57 (4): 503-16). The vector can include a promoter operably linked to the desired coding sequence.

The terms "promoter element," "promoter," or "promoter sequence" as used herein, refer to a DNA sequence that is located upstream to the 5' end (i.e. proceeds) the coding sequence. The location of most promoters known in nature precedes the transcribed region. The promoter functions as a switch, activating the expression of a coding sequence. If the coding sequence is activated, it is said to be transcribed, or participating in transcription. Transcription involves the synthesis of pre-RNA and RNA from the encoding sequence. The promoter, therefore, serves as a transcriptional regulatory element and also provides a site for initiation of transcription of the coding sequence into RNA. Promoters may be derived in their entirety from a native gene, or be composed of different elements derived from different promoters found in nature, or comprise synthetic DNA segments. It is understood by those skilled in the art that different promoters may direct the expression of a coding sequence in different tissues or cell types, or at different stages of development, or in response to different environmental conditions. It is further recognized that since in most cases the exact boundaries of regulatory sequences have not been completely defined, DNA fragments of some variation may have identical promoter activity. Promoters which cause a gene to be expressed in most cell types at most times are commonly referred to as "constitutive promoters".

According to the teachings of the present invention, the promoter can be an organism native promoter or a heterologous promoter, which may be a constitutive promoter, an induced promoter or a tissue specific promoter. According to some embodiments, when the organism is a plant, the promoter can be a tissue specific promoter.

The expression system or a vector comprising same can comprise additional regulatory elements including, for example, an enhancer, a terminator, and a transcriptional activator.

"Enhancer" generally refers to a sequence of DNA that functions at no fixed distance from the transcription start site and can be either 5' or 3' to the transcription unit. Further-more, enhancers can be within an intron as well as within the coding sequence itself. Enhancers are usually between 10 and 300 bp in length, and they function in cis. Enhancers function to increase transcription from nearby promoters.

Enhancers, like promoters, also often contain response elements that mediate the regulation of transcription. Enhancers often determine the regulation of expression. Enhancers can be in trans and away from the control sequence.

Expression vectors used in eukaryotic host cells (yeast, fungi, insect, plant, animal, human or nucleated cells) can also contain sequences necessary for the termination of transcription which can affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs.

The vector can include nucleic acid sequence encoding a marker product. This marker product can be used to determine if the expression system has been delivered to the cell and once delivered is being expressed. Exemplary marker genes are the *E. coli* lacZ gene which encodes β-galactosidase, green fluorescent protein, and the GUS reporter system.

In some embodiments the marker can be a selectable marker. When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection include the drugs neomycin, mycophenolic acid, hygromycin or kanamycin.

It is to be explicitly understood that while the expression system and/or a vector comprising same may include a promoter and/or additional regulatory elements, the presence of such regulatory elements is not obligatory. The ECE or expression system of the present invention or the vector comprising same may be so designed to be inserted into the target cell genome as to be operably linked to the cell's endogenous regulatory elements.

Transforming the ECE, expression system of a vector comprising same into at least one host cell can be performed by any method as is known to a person skilled in the art. The terms "transformation" and "transfection" are used herein interchangeably and refer to the introduction of a polynucleotide into a living cell.

Transformation of a cell may be stable or transient. The term "transient transformation" or "transiently transformed" refers to the introduction of one or more heterologous (or exogenous) polynucleotides into a cell in the absence of integration of the exogenous polynucleotide into the host cell's genome. Transient transformation may be detected by, for example, enzyme-linked immunosorbent assay (ELISA), which detects the presence of a polypeptide encoded by one or more of the transcribable polynucleotides or by nucleotide-based (NAT)-assays such as polymerase chain reaction (PCR) using proper primers. Alternatively, transient transformation may be detected by detecting the activity of a marker protein (e.g. α-glucuronidase) encoded by the exogenous polynucleotide.

In contrast, the term "stable transformation" or "stably transformed" refers to the introduction and integration of one or more heterologous (or exogenous) polynucleotides into the genome of a cell. Stable transformation of a cell may be detected by Southern blot hybridization of genomic DNA of the cell with nucleic acid sequences which are capable of binding to one or more of the exogenous polynucleotides. Alternatively, stable transformation of a cell may also be detected by enzyme activity of an integrated gene in growing tissue or by PCR of genomic DNA of the cell to amplify exogenous polynucleotide sequences. The term "stable transformant" refers to a cell which has stably integrated one or more exogenous polynucleotides into the genomic or organellar DNA.

The terms "transformants" or "transformed cells" include the primary transformed cell and cultures derived from that cell regardless to the number of transfers. All progeny may not be precisely identical in DNA content, due to deliberate or inadvertent mutations. Mutant progeny that have the same functionality as screened for in the originally transformed cell are included in the definition of transformants.

According to certain exemplary embodiments, the cell comprising the ECE or expression system of the present invention is a plant cell. The plant cell can form part of a cell culture, tissue culture, a plant part or an intact plant. According to other exemplary embodiments, the cell comprising the ECE or expression system of the present invention is an alga cell. The alga cell can form part of a cell culture, tissue culture, an alga part or an intact alga. It is to be explicitly understood that intact plant, alga or fungus comprises at least one cell comprising the ECE or the expression system of the present invention are encompassed within the scope of the present invention.

Among the most commonly used promoters used for the expression of heterologous sequences in plants are the nopaline synthase (NOS) promoter (Ebert et al., 1987 Proc. Natl. Acad. Sci. U.S.A. 84:5745-5749), the octapine synthase (OCS) promoter, caulimovirus promoters such as the cauliflower mosaic virus (CaMV) 19S promoter (Lawton et al., 1987 Plant Mol Biol. 9:315-324), the CaMV 35S promoter (Odell et al., 1985 Nature 313:810-812), and the figwort mosaic virus 35S promoter, the light inducible promoter from the small subunit of rubisco, the ADH promoter (Walker et al., 1987 Proc Natl Aca. Sci U.S.A. 84:6624-66280, the sucrose synthase promoter (Yang et al., 1990 Proc. Natl. Acad. Sci. U.S.A. 87:4144-4148), the R gene complex promoter (Chandler et al., 1989. Plant Cell 1:1175-1183), the chlorophyll a/b binding protein gene promoter, etc. Other commonly used promoters are, the promoters for the potato tuber ADPGPP genes, the sucrose synthase promoter, the granule bound starch synthase promoter, the glutelin gene promoter, the maize waxy promoter, Brittle gene promoter, and Shrunken 2 promoter, the acid chitinase gene promoter, and the zein gene promoters (15 kD, 16 kD, 19 kD, 22 kD, and 27 kD; Perdersen et al. 1982 Cell 29:1015-1026). A plethora of promoters is described in International Patent Application Publication No. WO 00/18963.

Promoters useful to direct expression in algae are also well known in the art, and include inducible promoter and constitutive promoters. In some embodiments, the algal-specific promoter is a constitutive promoter or a light-induced promoter such as the RUBISCO rbcS promoter (e.g. U.S. Application Publication No. 2010/0081177). Additional promoters that can be used include, for example without limitation, a NIT1 promoter, an AMT1 promoter, an AMT2 promoter, an AMT4 promoter, an RH1 promoter, a cauliflower mosaic virus 35S promoter, a tobacco mosaic virus promoter, a simian virus 40 promoter, a ubiquitin promoter, a PBCV-I VP54 promoter, or functional fragments thereof, or any other suitable promoter sequence known to those skilled in the art.

There are various methods of introducing foreign genes into both monocotyledonous and dicotyledonous plants (for example, Potrykus I. 1991. Annu Rev Plant Physiol Plant Mol Biol 42:205-225; Shimamoto K. et al., 1989. Nature 338:274-276).

The principal methods of the stable integration of exogenous DNA into plant genomic DNA includes two main approaches: *Agrobacterium*-mediated gene transfer and Direct DNA uptake, the latter being applicable for transforming algal cells as well.

*Agrobacterium*-mediated gene transfer: The *Agrobacterium*-mediated system includes the use of plasmid vectors that contain defined DNA segments which integrate into the plant genomic DNA. Methods of inoculation of the plant tissue vary depending upon the plant species and the *Agrobacterium* delivery system. A widely used approach is the leaf-disc procedure, which can be performed with any tissue explant that provides a good source for initiation of whole-plant differentiation (Horsch et al., 1988. Plant Molecular Biology Manual A5, 1-9, Kluwer Academic Publishers, Dordrecht). A supplementary approach employs the *Agrobacterium* delivery system in combination with vacuum infiltration. The *Agrobacterium* system is especially useful in the generation of transgenic dicotyledonous plants.

Direct DNA uptake: There are various methods of direct DNA transfer into plant cells. In electroporation, the protoplasts are briefly exposed to a strong electric field, opening up mini-pores to allow DNA to enter. In microinjection, the DNA is mechanically injected directly into the cells using micropipettes. In microparticle bombardment, the DNA is adsorbed on microprojectiles such as magnesium sulfate crystals or tungsten particles, and the microprojectiles are physically accelerated into cells or plant tissues.

Alternative method for introducing the expression system into the genome of a host cell is by genome editing. Genome editing is a reverse genetics method which uses artificially engineered nucleases to cut and create specific double-stranded breaks at a desired location(s) in the genome, which are then repaired by cellular endogenous processes such as, homology directed repair (HDR) and non-homologous end-joining (NHEJ). NHEJ directly joins the DNA ends in a double-stranded break, while HDR utilizes a homologous sequence as a template for regenerating the missing DNA sequence at the break point. In order to introduce specific nucleotide modifications to the genomic DNA, a DNA repair template containing the desired sequence must be present during HDR. Genome editing cannot be performed using traditional restriction endonucleases since most restriction enzymes recognize a few base pairs on the DNA as their target and the probability is very high that the recognized base pair combination will be found in many locations across the genome resulting in multiple cuts not limited to a desired location. To overcome this challenge and create site-specific single- or double-stranded breaks, several distinct classes of nucleases have been discovered and bioengineered to date. These include the meganucleases, Zinc finger nucleases (ZFNs), transcription-activator like effector nucleases (TALENs) and CRISPR/Cas system.

The splicing pattern controlling the expression of the coding sequence is determined by the amounts of polyamines/polyamines analogs sensed by the cell comprising the ECE or expression system of the invention and/or other chemicals or molecules that increase or alter polyamines levels within the cell or its immediate environment. Increase in the polyamines/analogs levels results in reduction or prevention of the polyamine or polyamine analogue responsive exon inclusion within the RNA transcript. According to certain embodiments, the absence of the exon yields a functional RNA transcript. Reduced polyamines/analog levels result in increase of the polyamine or polyamine analogue responsive exon inclusion. According to certain embodiments, the presence of the exon results in the formation of non-functional RNA transcript. According to certain exemplary embodiments, inclusion of the exon within the transcribed RNA results in the insertion of premature stop codon into the transcribed RNA.

Mutations in the ECE sequence and/or introns flanking same may alter its structure and/or function and affect the splicing frequency and/or the ECE responsiveness to the polyamine or analogue thereof. As described hereinabove, the mutations can result in ether enhancing or reducing the splicing frequency/polyamine responsiveness. Moreover, the ECE can be combined with other regulatory elements, such as promoters, to strengthen the promoter control on expression. Inducible promoters known in the Art, for example heat shock responsive promoter, may provide for about 95% control of the expression (i.e. about 5% "leakiness", that is background expression regardless of heat). Combining the ECE and expression systems comprising same of the invention can reduce this background expression to less than 5% (under no polyamine/no heat conditions) and elevate the expression to near 100% under heat and polyamine induction. In this case, the expression control is close to off/on regulation.

Regardless of organism or construct type, the present invention can be used in an open loop manner by applying/administering a polyamine or analog or a chemical or factor that can modulate internal polyamine levels or in a closed loop manner in which the polyamine levels are internally controlled by an inducer.

The level of endogenous polyamines can be manipulated by various reagents or molecules. According to some embodiments, depletion of polyamines can be induced by chemicals affecting the activity of enzymes in the polyamine biosynthesis, for example difluoromethylornithine (DFMO), an irreversible inhibitor of ornithine decarboxylase (ODC), the rate-controlling enzyme in the biosynthesis of putrescine and spermidine. MG-132 inhibits proteasomal degradation of the spermine/spermidine actyl transferase (SSAT) and thus increases the amount of SSAT enzyme protein and reduces polyamines levels. Alternatively, or in addition, regulating expression of genes involved in the polyamine biosynthesis pathway can be used to alter the endogenous polyamine level and change the splicing pattern of ECE harboring genes. Coupling the expression of these polyamine-altering genes with developmental genes (under the same promotor) may result in a developmentally-dependent splicing pattern of other ECE harboring genes. For example, the promoter of a gene that induces flowering in plants such as CO (SEQ ID NO:46) can be used to control the gene encoding spermine synthase (SEQ ID NO: 47). In such a scenario, the spermine synthase will be expressed at flowering which in turn will result in increased spermine levels and silencing of ECE harboring genes. In another example, a gene encoding insect resistance in plants (e.g., HM107006 Synthetic construct delta-endotoxin (Cry1C) gene, SEQ ID NO:62) can be modified with the ECE sequence of the present invention and used with the above-described flowering-expressed spermine synthase in order to prevent expression of the insecticide during flowering.

Advantageously, preliminary experiments (see Example 3 hereinbelow) have shown that the endogenous level of polyamine within a plant cell transformed with an exemplary construct comprising the ECE of the present invention had no significant effect on the splicing pattern of the system. Accordingly, mediating splicing that would result in expression of the desired coding sequence requires exposure of the cells to an effective amount of polyamine or polyamine analog, which is significantly easier to control and manipulate compared to controlling the endogenous level of polyamine.

The ability to limit the expression of resistance genes (e.g., gene conferring resistance to herbicide or pesticide) to when needed has many advantageous. It is not only metabolically more efficient; it might also have a major role in protecting the environment from the deleterious effects of such gene products. For example, shutting down expression of an insecticide gene during flowering can be used to protect insects pollinating the crops.

The splicing pattern controlling the expression of the coding sequence is determined by the amounts of polyamines/polyamines analogs sensed by the cell comprising the expression system of the invention. Particular amounts will depend on the type and form of the host cell (e.g. cell culture, tissue culture or an intact organism) and can be determined by a person skilled in the Art.

As described hereinabove, the use of the expression control system of the present invention is not confined to specific type of host cells nor to particular transcribable polynucleotide, and thus provide for broad and versatile optional uses. The expression of a desired transcript, being based on polyamine or polyamine responsive alternative splicing, enables controlling the timing of the expression.

For example, algae, particularly microalgae are thought to offer great potential as expression system for various industrial, therapeutic and diagnostic recombinant proteins. Cultures of plant cells have also been developed for the same purposes. Microalgae and plant cell cultures combine high growth rates with all benefits of eukaryotic expression systems, and, moreover, are photosynthetic organisms hence the energy required for protein expression is based on natural $CO_2$ and involves only low production costs. However, a constitutive expression of exogenous RNA or protein product within the alga or plant host cell may interfere with the cell normal growth and establishment of a cell culture required for producing desired amounts of the expressed product. Using the system of the invention, the expression can be easily regulated to only after the cell culture has reached an optimal density by controlling the amount of polyamine or polyamine analogs to which the cells in the culture are exposed.

Additional example in which the use of the system of the present invention may be beneficial is in controlling developmental or other specific processes in the growth cycle of a host cell or a eukaryotic organism, particularly plant. The production of hybrid plants in agriculture, the hybrids known to be superior over each of the parental lines is highly depended on the ability to produce male sterile plants, such that self-pollination is avoided. However, crossing male sterile plants with fertile female plant typically results in the production of large fraction of sterile seeds, which, when sown, would produce sterile plants. This is a significant disadvantage when the crop is seeds (such as in wheat, rice and the like). Using the expression control elements of the present invention enables reversible expression of polynucleotides conferring male sterility, such that such trait is observed only when desired.

Genome editing is a powerful tool to impact target traits by modifications of the target plant genome sequence. It is a reverse genetics method which uses artificially engineered (endo) nucleases to cut and create specific double-stranded breaks at a desired location(s) in the genome, which are then repaired by cellular endogenous processes such as, homology directed repair (HDR) and non-homologous end-joining (NHEJ). Yet, nuclease expression may cause DNA damage to the targeted host cell due to non-specific DNA binding and digestion by such enzymes. For example, various methods have been developed to control zinc finger nucleases in living plant cells, yet none has been reported to enable tight control on zinc finger nucleases expression in specific cells and tissues. The system of the present invention enables controlling the timing of the nuclease expression. Such control may improve the preciseness of the enzyme activity and the genome editing.

Viral vectors are useful tools for transient gene expression in plant cells, organs and tissues. Upon local infection, viral genomes can multiply and move systematically into non-infected tissues, rendering the plant into a factory of protein production. In most cases, expression of the foreign genes coincides with viral spread. Engineering viral vectors to produce functional target proteins upon application of the foreign inducer, will allow more robust gene expression in infected plants as it will allow expression of the target genes only after efficient spread of the viral vector.

In more general terms, the expression control element of the present invention may be used to control the expression of any exogenous polynucleotide transformed to a host cell. The expression dependency on the presence and amount of polyamine and/or polyamine analogs significantly reduces or even prevents the risk of uncontrolled expression and contamination of the environment with genetically modified host cells and organisms. For example, the commercial use of transgenic plants is currently limited in many trees, grasses and various monocots with close wide type related species due to the risk of transgene flow into the environment and close relative species. Several methods have been developed to cause pollen or oval abolition in transgenic plants by spatial, tissue or cell specific expression of toxic genes. While such methods may abolish gene transfer into the wild, they also hinder our ability to further manipulate the transgenic plants in controlled environment for breeding and other purposes. Engineering these toxic genes in a way that their expression will be abolished by application of polyamine or polyamine analogues will allow for bypassing pollen or oval abolition under controlled environment.

According to some embodiments, the functional transcript or protein product encoded by same is a regulatory element According to certain embodiments, the regulatory element is selected from the group consisting of transcription control factor, translation control factor and the like. The regulatory element can have a positive or negative regulatory effect on a gene comprising said regulatory sequence recognition sequence. Each possibility represents a separate embodiment of the present invention.

An example is the GAL4-UAS system: The ECE can be embedded into the GALA gene to control its expression. The GAL4 gene encodes the yeast transcription activator protein GAL4. Therefore, the expression of genes that have UAS (upstream activation sequence-enhancer to which GAL4 specifically binds to activate gene transcription) is under the splicing regulation of the ECE of the invention.

Additional example describes the use of the ECE element of the invention to control viral expression: the sequence encoding a transcription factor (as above) or any other viral regulatory protein can be cloned into a sequence that code for a virus such as the TRV (tobacco tattle virus). The ECE embedded in such a construct controls the expression of genes with recognition site for the transcription factor or the virus in cells, tissues, organs or organism infected by the virus.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Material and Methods

Plasmids used for transforming the expression control element or a system comprising same to plants are presented in Table 1 hereinbelow

TABLE 1

| Plasmids for transforming plant cells | | | |
|---|---|---|---|
| Designated name/ number | Plasmid based on | Promoter | Regulatory sequence inserted |
| syz24-1.2 | Psat3A-5061 | NOS | GUS intron + wild type (wt) SSAT derived ECE |
| syz24-2.2 | Psat3A-5061 | NOS | GUS intron + Mutated SSAT derived ECE (GTC-to-AGT) |
| syz24-1.1 | Psat6A-5013/5304 | 35S | GUS intron + WT SSAT derived ECE |
| syz24-2.1 | Psat6A 5013/5304 | 35S | GUS intron + Mutated SSAT derived ECE (GTC-to-AGT) |
| Pzp4508/ syz24-1.2 | Ppzp based on Psat3 | NOS | GUS intron + wt SSAT derived ECE |
| Pzp 1503/ syz24-1.2 | Ppzp based on Psat3 | NOS | GUS intron + Mutated SSAT derived ECE (GTC-to-AGT) |
| To be designated | Ppzp based on Psat6 | 35S | GUS intron + WT SSAT derived ECE |
| To be designated | Ppzp based on Psat6 | 35S | GUS intron + Mutated SSAT derived ECE (GTC-to-AGT) |
| 5060 | mpr; plant expression vector, 35Sprom-TL-GUS-35SpolyA (TL is from pTL-7SN; GUS is from pRAJ275) J. | 35S | |
| 7653 | 35Spromoter-GUS plus NPTII resistance (Kan) in plants | | GUS intron |
| 5488 | Tetracycline repressor (TetR) controlled gene expression; binary vector expressing GUS + intron from 35Sprom. w/triple X operators (see MGG 220, 245-250 for GUS + intron description) and 35S polyA; Kan$^r$ in *E. coli* and Hygr$^r$ in plants; see Veinmann P et al., Plant J. 5, 559-569 (1994) | | GUS intron + Hygro |
| 5237 | plant stable transformation vector with constitutive expression cassette of the hpt gene as selection marker and heat shock (hsp) induced expression cassette of GUS; expression of hpt controlled by octopine synthase promoter-activator (ocsAocsP) and terminator (ocsT); expression of GUS controlled by heat sock inducible (hspP) promoter and 35S terminator (35ST); made by cloning the hspP.GUS expression | | GUS intron + Hygro |

TABLE 1-continued

Plasmids for transforming plant cells

| Designated name/ number | Plasmid based on | Promoter | Regulatory sequence inserted |
|---|---|---|---|
| | cassette from pSAT4.hspP.GUS (TT3087) as an I-SceI fragment into the same sites of pRCS2.ocs-hyg(b) (TT2287); RB-PI-TliI-PI-PspI-I-CeuI-ISceI-(hsp-GUS expression cassette)-I-SceI-IPacI-IPpoI-AscI-(hyg expression cassette)-AscI-LB; Specr/Strepr (20/50 µg/ml in *E. coli* and 300/200 µg/ml in Agro). | | |
| Pzp4508/ syz24-1.2Hygro | | | GUS intron + WT SSAT derived ECE + Hygro |
| Pzp 1503/ syz24-1.2Hygro | | | GUS intron + MUT SSAT derived ECE + Hygro |
| 5061 (Psat3A) | Ampr; plant expression vector, 35Sprom-TL-GUS-35SpolyA (TL is from pTL-7SN; GUS is from pRAJ275) | NOS | GUS intron |
| 5304 (Psat6A) | Plant transient gene expression vector with MCS; MCS + 35SpolyA cloned as NcoI-NotI PCR frag. w/pSAT6-EGFP-C1 (E1454) as template into the same sites of pAUX3133-35S-TL [=pAUX3133 (E1309) w/added 2 × 35Sprom. and TL translational enhancer from pRTL2-GUS (E088); PIPspI-AgeI-2 × 35Sprom.-TL-NcoI-MCS-XbaI-35SpolyA-NotI-PIPspI; MCS: BspEI(not unique, 35Sprom. has BspEI)-BglII-XhoI-SacI-HindIII-EcoRI-PstI-SalI-AccI-KpnI-SacII-XmaI-ApaI-SmaI-BamHI-XbaI; 3,884 bp; clone 13 Ampr | 35S | GUS intron |

Plasmid Preparation

Preparation of plasmid syz24-1.2, syz24-2.2, syz24-1.1, syz24-2.1, Pzp4508/syz24-1.2, Pzp 1503/syz24-1.2 was as follows:

Two fragments were synthesized (by Syntezza Bioscience Ltd.): SSAT derived ECE (including SSAT derived polyamine responsive polynucleotide flanked by SSAT derived first (upper) and second (lower) introns); and its mutated form+GUS derived introns and exon. The fragments were enzymatically digested by KpnI and BamHI and cloned (Syntezza Bioscience Ltd.) into 5061 (pSAT3) and 5304 (pSAT6) that were enzymatically digested by the same enzymes essentially as described in Tzfira et al., (2005, ibid). Plasmids were kindly given by Targetgene Biotechnologies Ltd. Four plasmids were generated (syz24-1.2, syz24-2.2, syz24-1.1, syz24-2.1). The SAT-ECE was located within the GUS intron. Gus intron split the GUS sequence to the AUG start codon and the rest of GUS sequence. Plasmids syz24-1.2 and syz24-2.2 were enzymatically digested by ppoI and clone into two pzp plasmids: 4508, 1503 (kindly given by Targetgene Biotechnologies Ltd.) to generate Pzp4508/syz24-1.2 and Pzp 1503/syz24-1.2.

Preparation of Pzp4508/syz24-1.2Hygro and Pzp 1503/syz24-1.2Hygro plasmids:

Plasmid 5237 was enzymatically digested by ascI. The fragment code for the hygromycin selection was extracted from gel.

Plasmids Pzp4508/syz24-1.2 and Pzp 1503/syz24-1.2 were digested by AscI and underwent dephosphorylation. The digested plasmids underwent ligation with the extracted fragment (hygromycin) to produce Pzp4508/syz24-1.2Hygro and Pzp 1503/syz24-1.2Hygro plasmids.

Example 1: Use of the Expression System of the Invention for Controlling GUS Expression in *Arabidopsis thaliana* Protoplasts The GUS reporter system (GUS: B-glucuronidase) was used to demonstrate the features of the expression system of the invention.

*Arabidopsis* protoplasts were prepared as previously described (Wu F-H et al. 2009. Plant methods 5:16 doi: 10.1186/1746-4811-5-16).

Plasmids syz24-2.1 and a control plasmid 5060 (constitutive GUS expression) were transformed (in the presence or without 10 µM BENZ (BZ-CAS 121749-39-1-BZ) into protoplasts (Wu et al., supra). Transfected protoplasts were washed and cultured in W5 solution with or without BENZ (BZ) in 1% bovine serum albumin-coated 15 ml tubes for 16 h at 28° C. to allow expression of the transfected DNA.

The GUS expression system enables detection of a functional β-glucuronidase when protoplasts expressing the gene are incubated with the enzyme substrate 5-bromo-4-chloro-3-indolyl glucuronide (X-Glu), where the product of the reaction is a clear blue color. As described hereinabove, the expression system of the invention was introduced into an intron within the GUS encoding gene. The polyamine analog $N^1,N^{11}$-Diethylnorspermine tetrahydrochloride (BENZ, CAS 121749-39-1) was used to mediate splicing.

The following assays were designed:
1. Non transformed protoplasts
2. Non transformed protoplasts exposed to 10 μM BENZ
3. Non transformed protoplasts exposed to 100 μM BENZ
4. Protoplast transformed with plasmid syz24-2.1 without exposure to BENZ
5. Protoplast transformed with plasmid syz24-2.1 exposed to 10 μM BENZ
6. Protoplast transformed with plasmid syz24-2.1 exposed to 100 μM BENZ
7. Protoplast transformed with plasmid 5060 without exposure to BENZ
8. Protoplast transformed with plasmid 5060 exposed to 10 μM BENZ
9. Protoplast transformed with plasmid 5060 exposed to 100 μM BENZ In all assays in which the transformed protoplasts were exposed to BENZ, the transformation and subsequent washes were performed in the presence of the corresponding BENZ concentration (10 or 100 μM). After the last wash, the protoplasts were suspended in W5 buffer containing 10 μM or 100 μM BENZ and placed at 28° C. for 48 h. Thereafter the protoplasts were collected (by spinning at 100gX3 minutes). Protoplasts were resuspended in 0.5 ml 0.5M monitol+0.5 mg X-glucuronide (sigma B5285) and incubated at 37° C. 24 h.

FIG. 1: *Arabidopsis thaliana* protoplasts transfected with plasmid comprising the expression system within the GUS intron sequence resulted in GUS expression (indicated by β-glucuronidase activity) in a BENZ (polyamine analog) depended manner.

Non-transformed protoplasts were incubated with W5 medium (1); with 10 μM BENZ (2) or with 100 μM BENZ (3). β-glucuronidase activity (blue color) was not observed in any of the non-transfected samples (1-3). Protoplast transformed with syz24-2.1 plasmid comprising the ECE within the GUS intron, incubated in W5 buffer (4); supplemented with 10 μM (5) or 100 μM (6) BENZ showed β-glucuronidase activity only when cells were incubated with W5 supplemented with 100 μM BENZ. Protoplast transformed with the control 5060-constitute GUS intron expression plasmid, incubated in W5 buffer (7) supplemented with 10 μM (8) or 100 μM (9) resulted in β-glucuronidase activity irrespective of the presence of BENZ. These results indicate that the intronic splice control sequence (ECE) is spliced out (mediated splicing out of the SSAT-derived premature termination codons) and allow transcription and translation of the GUS gene under BENZ supplementation.

Example 2: Use of the Expression System of the Invention for Controlling GUS Expression in Tobacco Leaf Discs Protocol 5 ml *Agrobacterium* starter (transfected with the relevant plasmids) were grown with the selection antibiotics at 28° C. with agitation of 350 rpm overnight. Thereafter, the solution was centrifuged for 5 min. at 4500 g. The pellet was resuspended in 10 ml Induction Medium supplemented with the relevant antibiotic and 100 μM Acetosyringone, incubated for 5-6 hours at 28° C., 250 rpm and then centrifuged for 5 min at 4500 g. The bacteria were resuspended in 10 ml Infiltration Medium supplemented with 200 μM Acetosyringone (1M in DMSO). The bacteria density is measured at 660 nm to obtain OD660=1.

The Induction Medium and Infiltration Medium are described herein below.

| Induction medium; (1 L) pH5.6 with 32% HCl | |
|---|---|
| | amount |
| K$_2$HPO$_4$ (Dibasic potassium phosphate) | 10.5 gr |
| KH$_2$PO$_4$ (Potassium dihydrogen phosphate) | 4.5 gr |
| (NH$_4$)$_2$SO$_4$ (Ammonium Sulfate) | 1 gr |
| NaCitrate (Sodium citrate) | 0.5 gr |
| Glucose (Dextrose) | 1 gr |
| Fructose | 1 gr |
| Glycerol | 4 ml |
| MgSO$_4$ (Magnesium Sulfate) | 0.12 gr |
| MES | 1.95 gr |

All the ingredients are autoclaved, or alternatively, glucose, fructose, and glycerol can be sterilized and mixed with the basal medium before use.

| Infiltration medium: (1 L) pH 5.6 with KOH | | |
|---|---|---|
| | final | amount |
| MgSO$_4$ (Magnesium sulfate) | 10 mM | 1.2 gr |
| MES | 10 mM | 1.95 gr |

All the ingredients are autoclaved.

Leaf discs were cut from *Nicotiana Benthamiana* plants and put in 24 wells with 400 μl of the relevant *Agrobacterium* with or without 50 μM BENZ. Vacuum was applied for 8 min and then slowly released, followed by additional vacuum cycle of 1 min and slow release and incubation for 10 min. The leaf discs were then separated from the *Agrobacterium* suspension and resuspended with MS buffer with or without 50 μM BENZ and incubated at 24° C. for three days. At the end of the incubation, the leaf discs were subjected to β-glucuronidase (GUS) assay.

β-Glucuronidase (GUS) Assay
1. Immerse leaf discs in staining solution (NaPO4 pH7 0.1M; EDTA 100 mM Triton X-100 0.1%; K$_3$Fe(CN)$_6$ 1 mM; x-gluc 2 mM
2. Incubate leaf discs overnight at 37° C.
3. Remove staining solution and wash several times with 70% ethanol Plasmid transformed into the leaf discs: plasmid Pzp 1503/syz24-1.2 or the control Plasmid 7653 (constitutive GUS expression). Transformation took place in the presence of or absence of 50 μM BENZ.

Figure 2A:
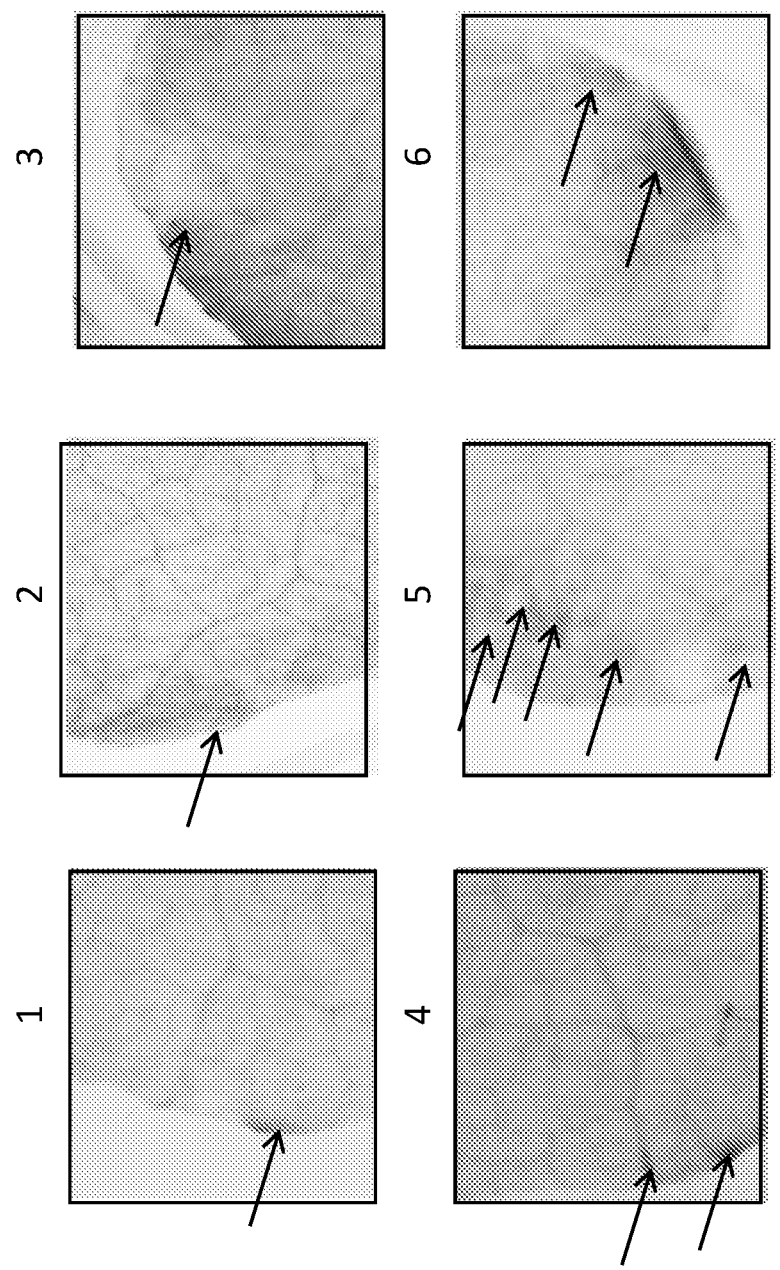
FIG. 2A: Leaf discs transfected with control plasmid (constitutive GUS expression) incubated in MS medium (1-3) or in MS supplemented with 50 μM BENZ (4-6).
Figure 2B:
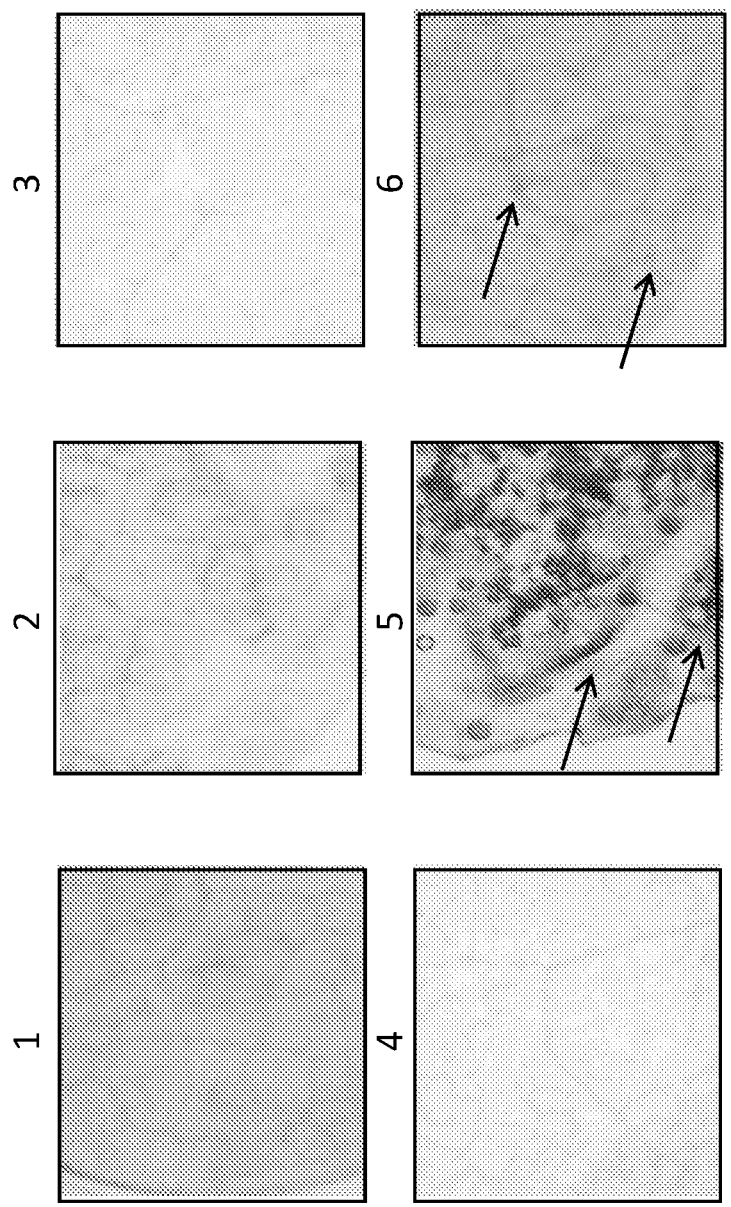
FIG. 2B: Leaf discs transfected with GUS comprising the expression control element incubated in MS medium (1-3) or in MS supplemented with 50 μM BENZ (4-6). Blue color spots/area is indicated by arrows.
Figure 3:
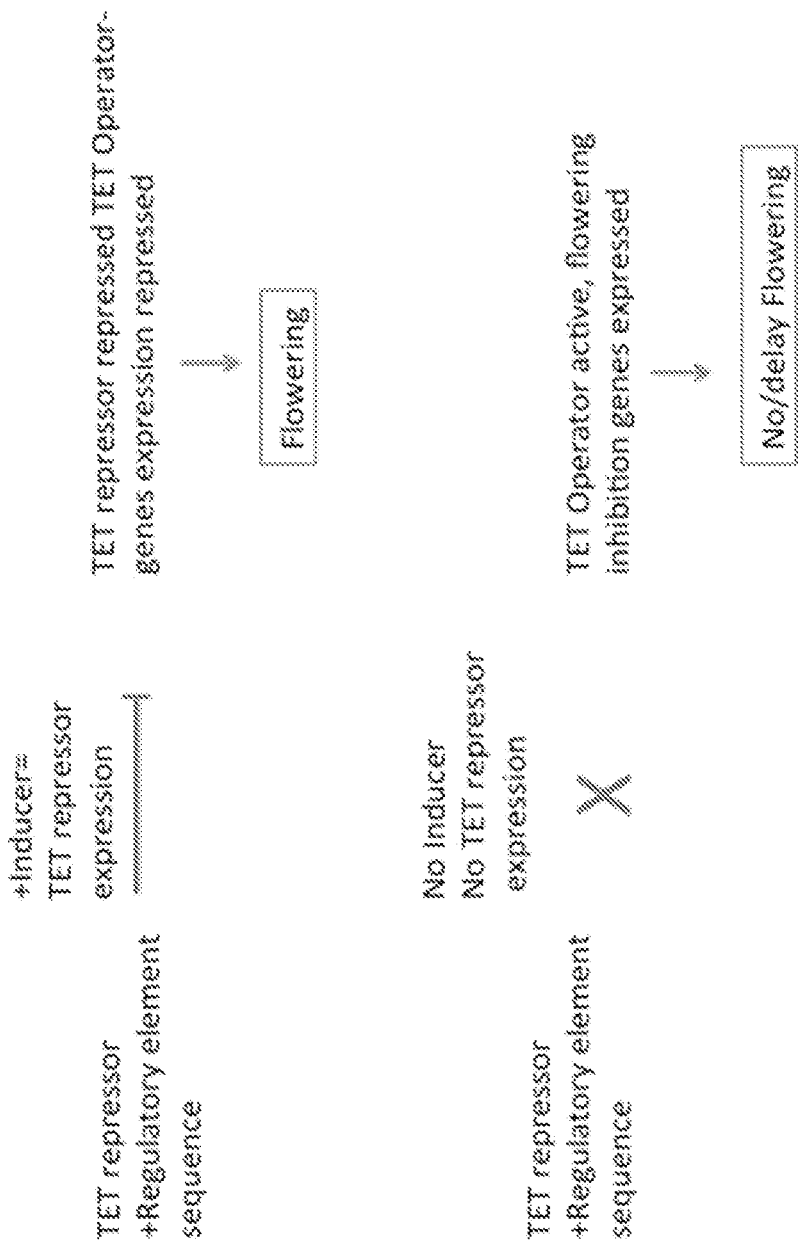
FIG. 3 schematically shows the first system including the expression system of the invention designed to control flowering in transgenic plants.
Figure 4:
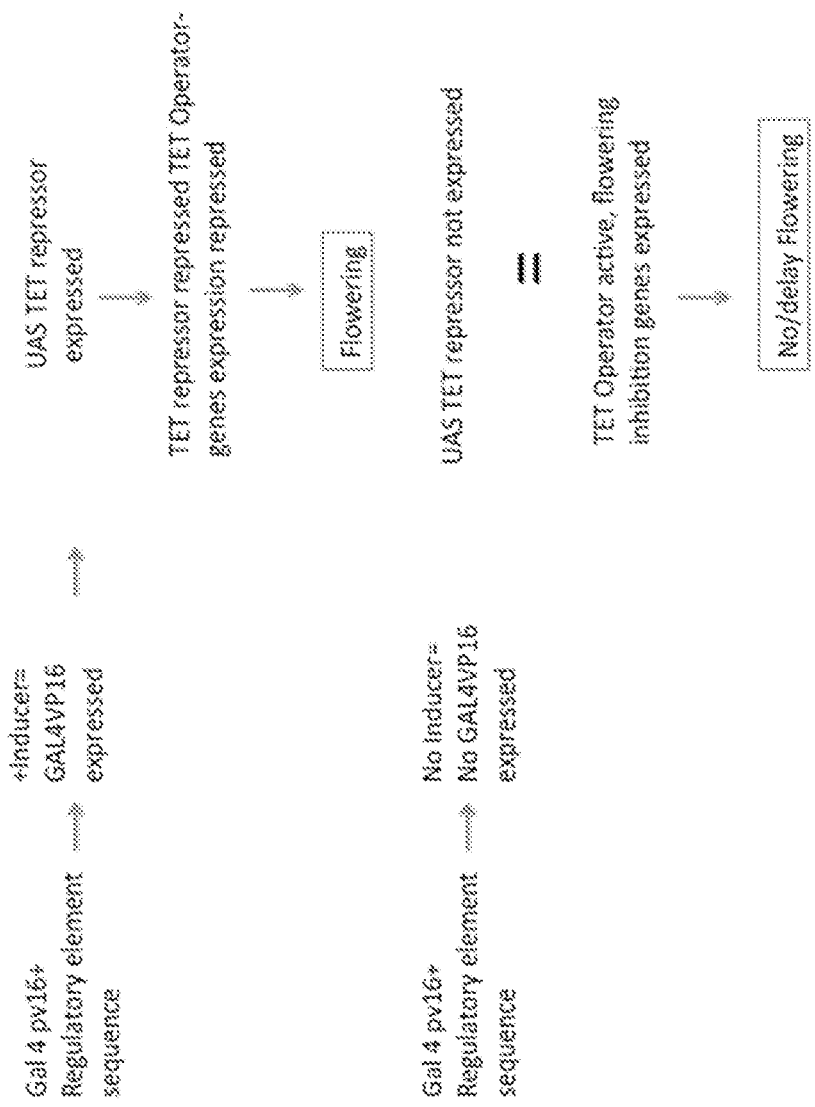
FIG. 4 schematically shows the second system including the expression system of the invention designed to control flowering in transgenic plants.
Figure 5B:
FIG. 5 shows transgenic T1 *Nicotiana benthamiana* plantlets produced from plants transformed with a plasmid comprising the ECE of the present invention (Pzp4508/syz24-1.2Hygro or Pzp 1503/syz24-1.2Hygro). The plantlets (with roors) are placed in containers containing water or PEI, such that the water/PEI is taken up by the plant's vascular system.
Figure 5A:

FIG. 2: *Nicotiana benthamina* leaf discs transfected with plasmid comprising the expression system within the GUS intron sequence resulted in GUS expression (indicated by β-glucuronidase activity) in a BENZ (polyamine analog) depended manner.

Leaf discs transformed with the control 7652 plasmid (constitutive GUS expression) expressed β-glucuronidase activity (blue color) when incubated in MS buffer (FIG. 2A 1-3) or with MS buffer supplemented with 50 μM BENZ polyamine analogue (FIG. 2A 3-6). Leaf discs transformed with the Pzp 1503/syz24-1.2 plasmid (GUS+the mutated ECE) showed no β-glucuronidase activity (blue color) when incubated in MS buffer (FIG. 2B 1-3). To the contrary, Leaf discs transformed with the Pzp 1503/syz24-1.2 plasmid and incubated with MS buffer supplemented with 50 μM BENZ showed β-glucuronidase activity. Blue spots indicated by arrows (FIG. 2B 4-6). These results demonstrate exclusion of the polyamine/polyamine analogue responsive exon in response to application of the polyamine analogue. In the experimental conditions described herein, exclusion of the exon resulted in functional β-glucuronidase transcript and formation of blue color in the presence of its substrate.

Example 3: Generating Tobacco Plants that Comprise the Expression System as Part of GUS Intron in their Genome Transfecting of *Nicotiana Benthamiana* plants was carried out as previously described (Maldonado-Mendoza I E et al. 1996. Transformation of tobacco and carrot using *Agrobacterium tumefaciens* and expression of the β-glucuronidase (GUS) reporter gene. Chapter 30, pp 261-274. In: *Plant Tissue Culture Concepts and Laboratory Exercises*. (Eds. R. N. Trigano and D. J. Gray). CRC Press, Boca Raton, USA). Plasmids Transfected:
1. Pzp4508/syz24-1.2Hygro
2. Pzp 1503/syz24-1.2Hygro The regeneration and growth process include the steps of selection of transformed cells based on antibiotic resistance, culturing those cells through the typical stages of embryonic development through the rooted plantlet stage. Transgenic embryos and seeds are similarly regenerated. The resulting transgenic rooted shoots were thereafter planted in hydroponic plant growth medium. Transgenic plants regenerated from transformed cells were grown to maturity and the presence of the inserted construct was verified by PCR. Positive transgenic plants (TO plants) were self-pollinated and seeds were collected. Selected seeds were used for producing T1 plants. T1 plants confirmed to harbor the transformed construct by PCR were used in the experiments. Polyamines were assembled into polyethylenimine (PEI) complexes based on the following equation:

$$m,PEI=15gr \to V,epoxide=14137\ \mu l(\text{calculation from synthesis}) \to V,EtOH=863\ \mu l$$

8230 μl of 100% Ethanol were add to 4 gr PEI (CAS Number: 25987 Jun. 8), then 3770 μl C14 Epoxide were added, and the mixture was shaken at 500 rpm for two hours. PEI final concentration was about 0.0284-0.046 gr per ml.

T1 Small *Nicotiana Benthamiana* plants (FIG. 5A) comprising either Pzp4508/syz24-1.2Hygro (grown from seed number 68) or with Pzp 1503/syz24-1.2Hygro (seed number 20) were extracted from soil and the cotyledon leaves were cut (using scissors), exposing the stem xylem. Each cut plantlet was soaked in either water or PEI solution (FIG. 5B) for 48 hours. Following the 48 hours, total proteins were extracted from 100 mg leaves. Proteins were loaded on SDS gel and Western blot was performed as previously described using GUS antibody (sigma G-5420).

Figure 6:
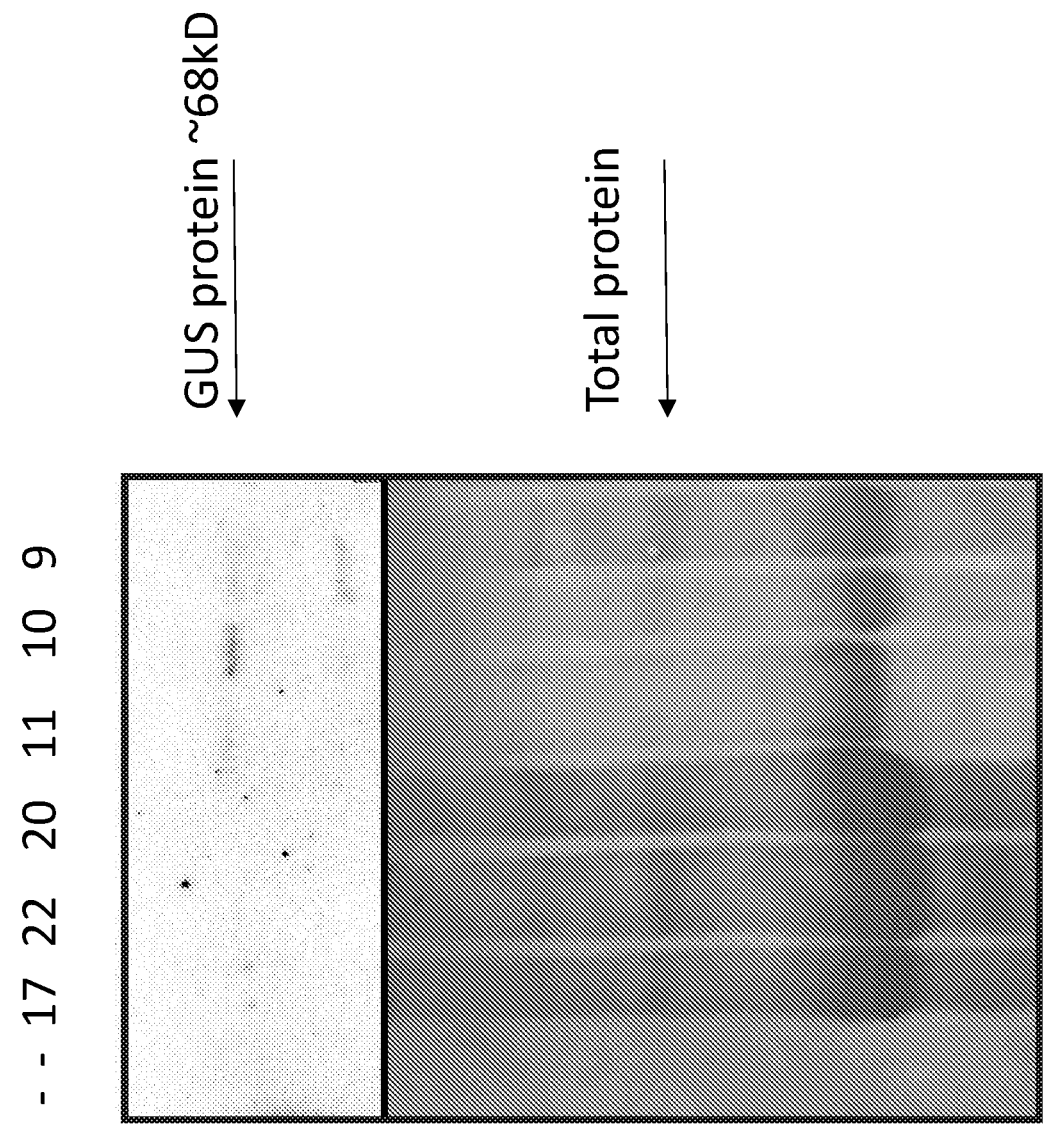
FIG. 6 demonstrate polyamine-depended expression of the GUS gene controlled by the ECE of the present invention by a Western blot of total proteins extracted from leaves of the transformed plant shown in FIG. 5. Each lane represents different T1 plant grown from seeds of TO plant 20, transformed with Pzp4508/syz24-1.2Hygro (lanes 9 and 17) or from TO plant 68 transformed with Pzp 1503/syz24-1.2Hygro (lanes 10,11,20 and 22). Lanes 9, 10 and 11 show proteins extracted from plants soaked in PEI. Lanes 20, 22, and 17 show proteins extracted from plants soaked in a water. The amount of loaded protein in the later (lanes 20, 22, and 17) was doubled compared to lanes 9, 10 and 11 to ensure that the protein amount is not a limiting factor of GUS detection.
Figure 7A:
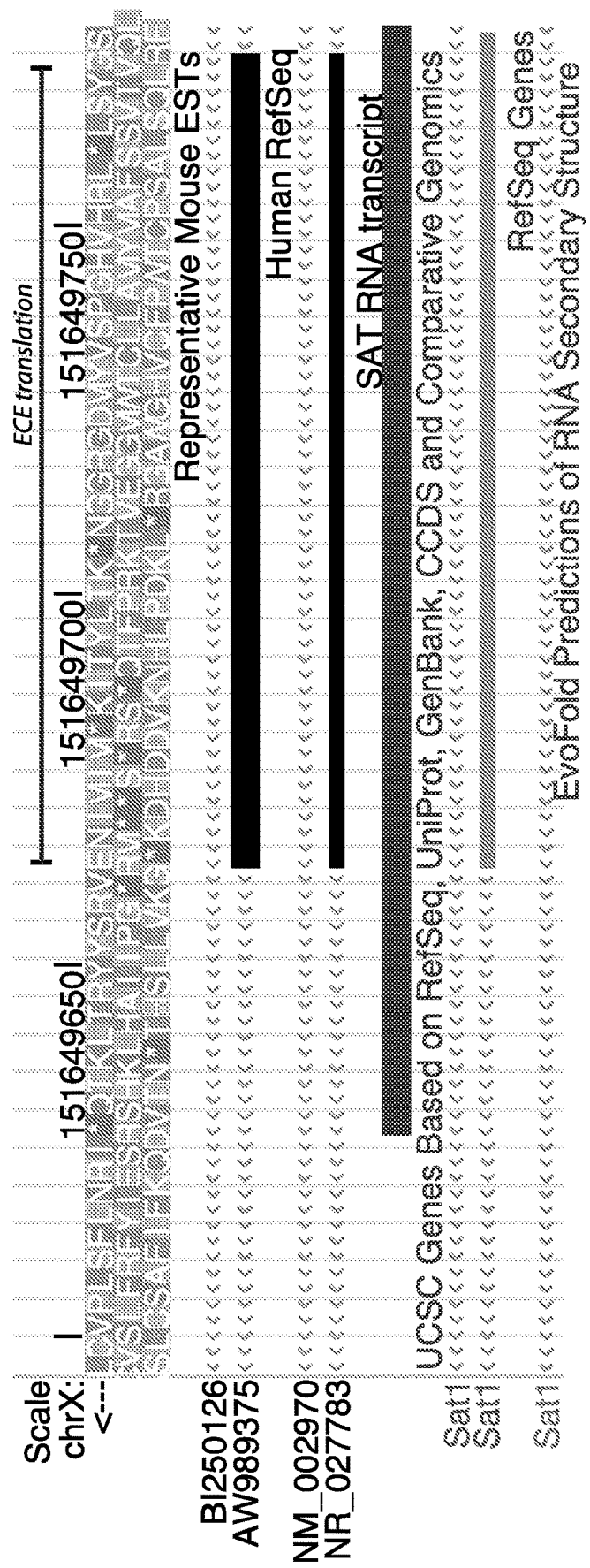
FIG. 7A-B shows phylogenetic alignment (FIG. 7A) and polynucleotide sequence alignment (FIG. 7B) of the ECE and its flanking intronic sequence from several vertebrate species
Figure 7A:
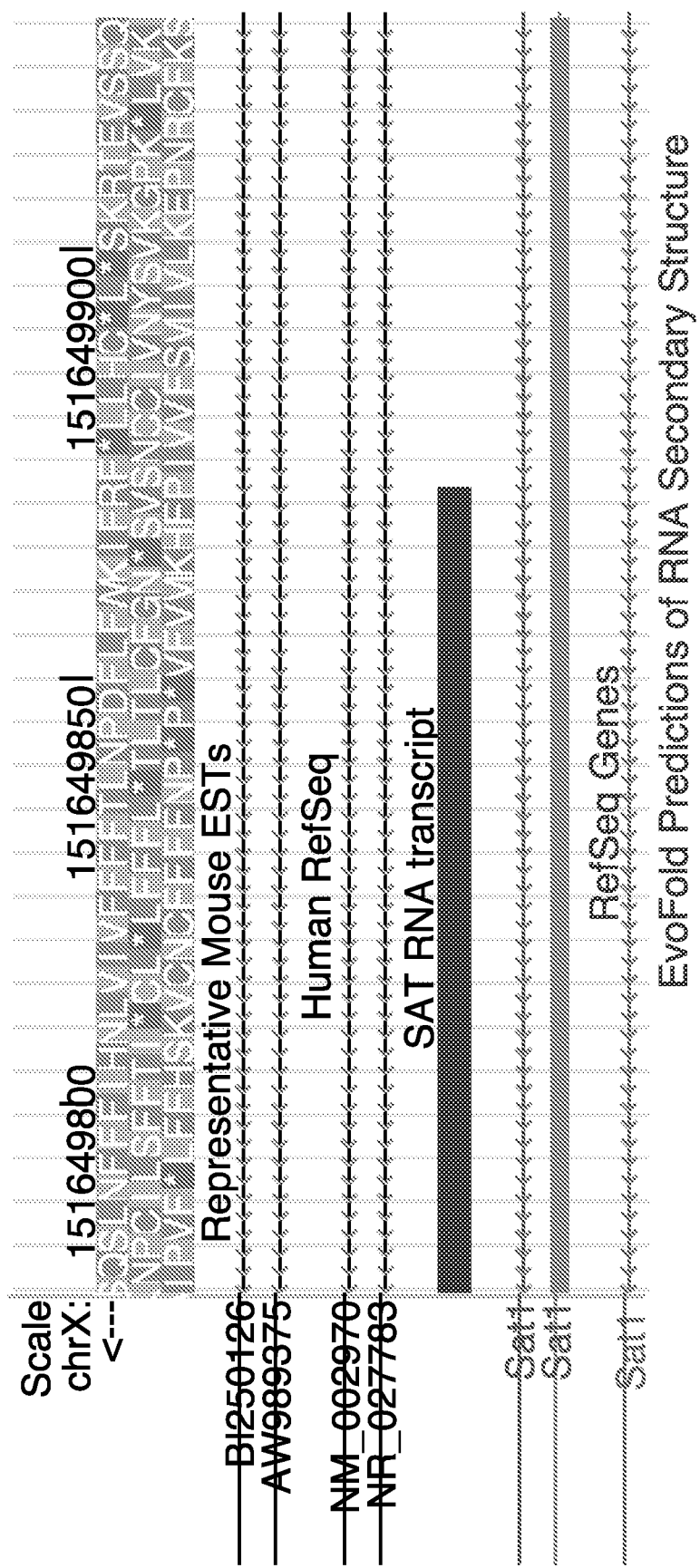
Figure 7B:
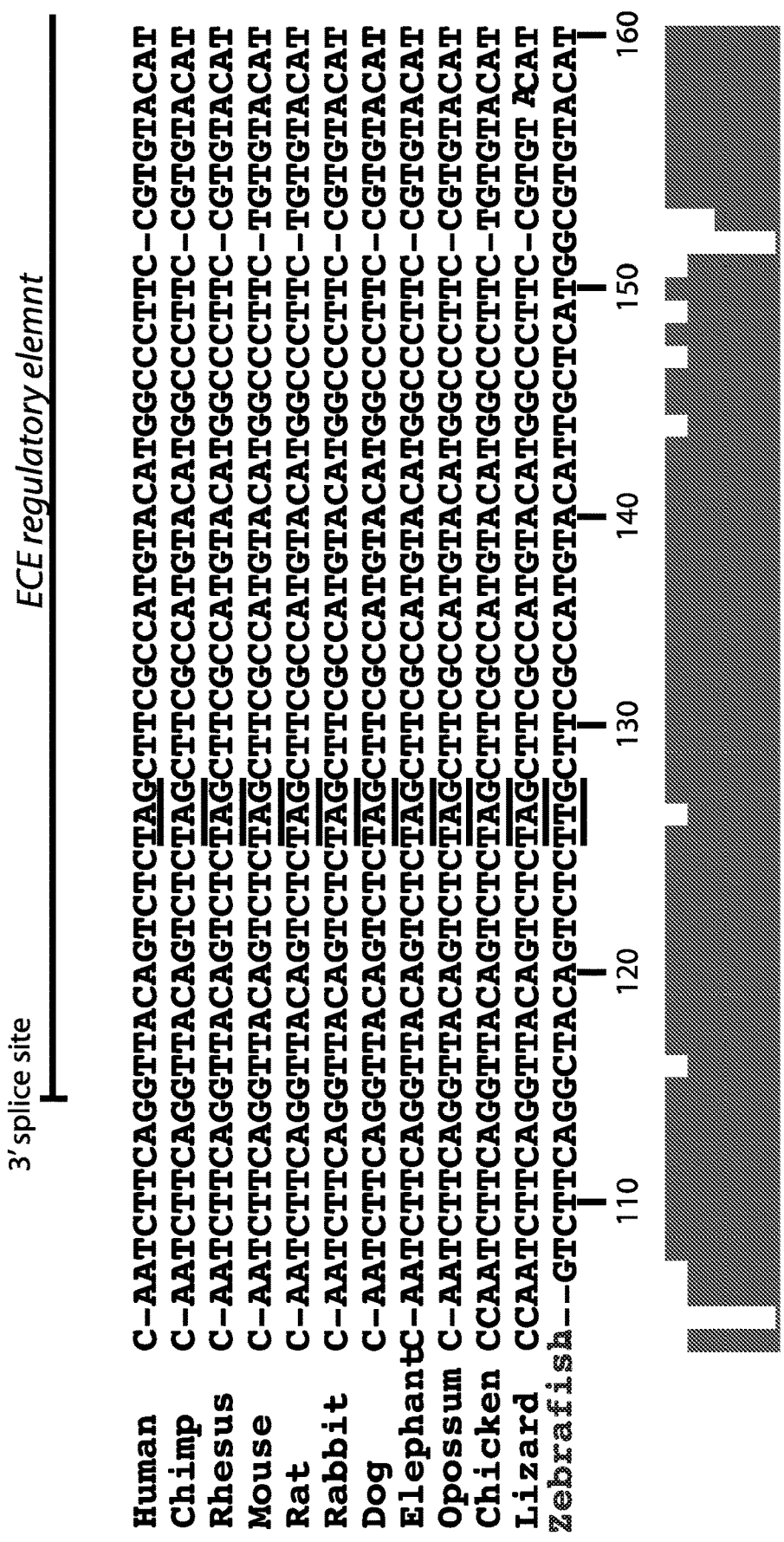
Figure 7B:
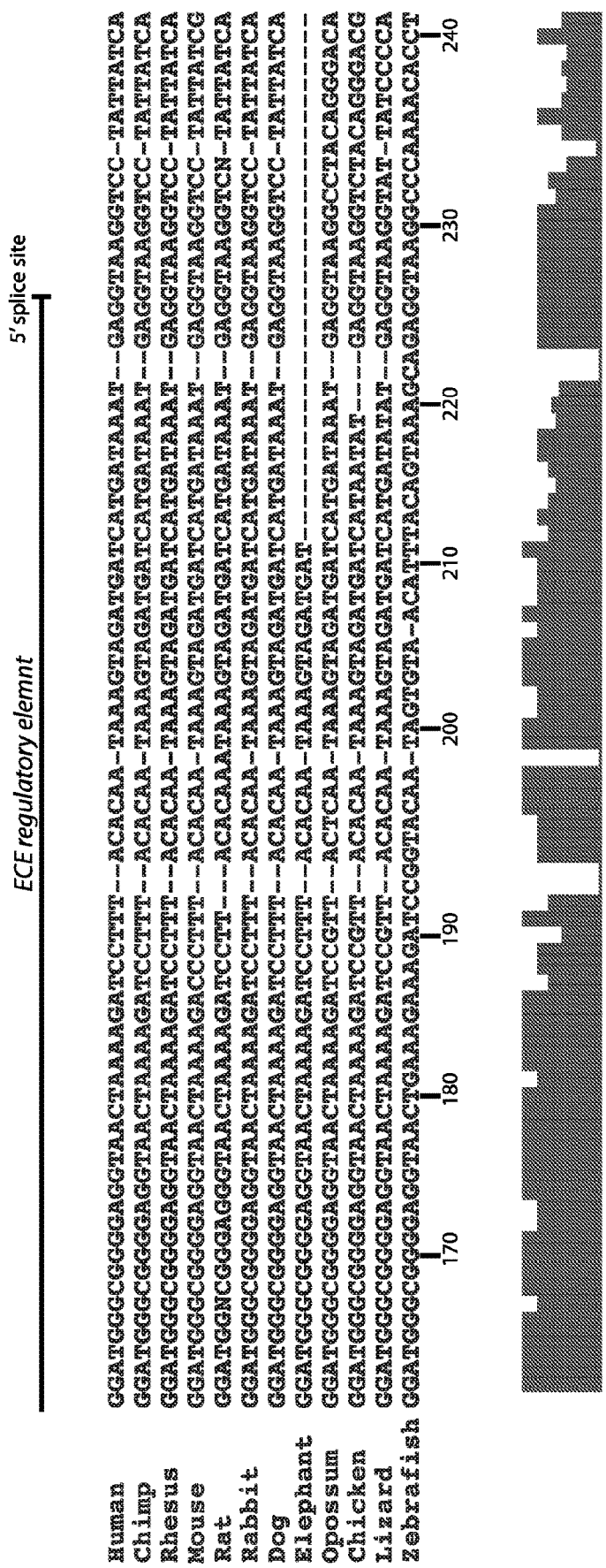

As is demonstrated in FIG. 6, ECE-GUS gene expression in the transformed T1 tobacco plantlet was altered in a PEI (polyamine) depended manner: GUS was expressed only when the plantlets were soaked in PEI but not when soaked in $H_2O$.

Example 4: Controlling Expression of Exogenous Therapeutic Proteins in Tobacco or Carrot Cell Cultures The use of plant viral vectors for the transient expression of heterologous proteins offers a useful tool for the large-scale production of proteins of industrial importance, such as antibodies and vaccine antigens. In recent years, advances have been made both in the development of first-generation vectors (that employ the 'full virus') and second-generation ('deconstructed virus') vectors (Gleba Y et al., 2007. Curr Opin Biotechnol. 2007 18 (2): 134-41). The system of the present invention can be used to provide an additional level of control of the expression of a desired protein encoded by the viral vector. The encoded protein can be the desired end-product protein or a transcription or translation factor that will activate the transcription and translation of various desired proteins.

Example 5: Control of Flowering Using the Expression System of the Invention

The initiation of flowering is a critical stage in a plant life cycle and is controlled by both environmental cues and endogenous pathways. Environmental cues include changes in temperature and daylight. Endogenous pathways function independently of environmental signals and are related to the developmental state of the plant, and thus are sometimes referred to as "autonomous" to indicate the lack of environmental influence. To prevent or delay flowering we targeted, for the first time, three pathways, by controlling the expression of (1) FLC (SEQ ID NO:38)—flowering inhibitor (autonomous pathway); (2) DELLA GI dominant negative mutation (SEQ ID NO:39) repressing flowering (hormonal pathway); and (3) CO constant protein—a key protein in the photoperiod pathway. The first two genes were constantly expressed while the expression of CO constant protein is inhibited by the expression of dsRNA (having SEQ ID NO: 40) targeted to this gene. The modulated expression delays/prevents flowering by constitutive expression of flowering inhibitors genes (FLC, GI DELLA dominant negative) and inhibition of CO constant protein by constitutive expression of siRNA targeted to the encoding gene. Flowering is induced by repressing the tetracycline (TET) operator located upstream to the promoter of these transgenic genes in an inducer-depended manner controlled by the "expression control element." Two options examined as described hereinbelow and in FIGS. 3 and 4:

1. The first system includes the "expression control element" embedded in the TET repressor sequence. In the absence of inducer, the TET repressor does not express and therefore the flowering inhibition genes, controlled by TET operator, are expressed continuously, resulting in no flowering/delayed flowering time. Once the inducer is supplemented/added, the TET repressor gene is expressed and inhibits the TET operator, reducing the expression of the flowering inhibiting genes; resulting in flowering induction.

2. The second system includes the "expression control element" embedded in GAL4pv16 sequence (a transcription factor that activates genes downstream to UAS promoter sequence). UAS promoter sequence located upstream to the TET repressor sequence. The aim of using GAL4PV16 expression system is to increase the expression level of the repressor under inducer supplementation condition. At the absent of inducer, GAL4PV16 does not express and TET repressor, controlled by the UAS promoter, does not express. Therefore, the flowering inhibition genes (controlled by the TET operator) are continuously expressed and inhibit flowering. In the presence of inducer, the GAL4PV16 transcription factor is expressed and activates the UAS promoter, located upstream to the TET repressor gene, which results in TET repressor transcription and inhibition of the TET operator located upstream to the flowering inhibition genes, leading to flowering.

Five fragments (SEQ ID NOs: 41-45) were synthesized and cloned into pPZP (T-DNA) plasmid by Gibson assembly. The constructs are described in Example 6 hereinbelow.

The plasmid is transferred into tobacco plants using Agrobacteria (as described hereinabove), and transgenic tobacco plants are generated. T1 plants are grown, and the level of the proteins FLC, DELLA G, and CO constants are examined in leaf samples. Assay plants are then exposed to the inducer or to water (by, for example, growing the plants in a medium containing the inducer/water or spaying the plants leaves with the inducer/water). The effect of the inducer on flowering is examined by comparing the level of FLC, DELLA G, and CO constants protein to the base level. The effect of the inducer is further examined phenotypically, i.e., the plants are left to grow until flowering occurs, and time of flower appearance is measured.

Example 6: Plasmid Generation

The fragments assembled by Gibson assembly to generate the four long fragments cloned into Ppzp-RCS2 plasmid by pIPSPI restriction enzyme digestion are as follows:
Plasmid A: Assembly of Sequences: 41+43+44:
  SEQ ID NO:41: pIPSPI site for cloning into Ppzp-RCS2 left+Gal4vp16+ "expression control element"+35S T (terminator)+UAS (promoter)+nlsTETrep (repressor)+35S T
  SEQ ID NO:43: Short homolog sequence to SEQ ID NO:41+nosP (promoter)+TET operator+siRNA CO+nos T (terminator)
  SEQ ID NO:44: Short homolog sequence to SEQ ID NO:43+ost P (promoter)+
  FLC+ost T (terminator)+pIPSPI site for cloning in to Ppzp-RCS2 right
Plasmid B: Assembly of Sequences: 41+43+44+45:
  SEQ ID NO:41: pIPSPI site for cloning in to Ppzp-RCS2 left+Gal4vp16+ "expression control element"+35S T (terminator)+UAS (promoter)+nlsTETrep (repressor)+35S T
  SEQ ID NO:43: Short homolog sequence to SEQ ID NO:41+nosP (promoter)+TET operator+siRNA CO+nos T (terminator) SEQ ID NO:44: Short homolog sequence to SEQ ID NO:43+ost P (promoter)+FLC+ost T (terminator)+pIPSPI site for cloning in to Ppzp-RCS2 right
  SEQ ID NO:45: Short homologous sequence to SEQ ID NO:44+C1 Robisco P (promoter)+DELLA mutant+Robisco T (terminator)+pIPSPI site for cloning into Ppzp-RCS2 right
Plasmid C: Assembly of Sequences: 42+43+44:
  SEQ ID NO:42: pIPSPI site for cloning into Ppzp-RCS2 left+35S P (promoter)+
  TET repressor (with the "expression control element" embedded).
  SEQ ID NO:43: Short homolog sequence to SEQ ID NO:41+nosP (promoter)+TET operator+siRNA CO+nos T (terminator)
  SEQ ID NO:44: Short homolog sequence to SEQ ID NO:43+ost P (promoter)+FLC+ost T (terminator)+pIPSPI site for cloning in to Ppzp-RCS2 right
Plasmid D: Assembly of Sequences: 42+43+44+45:
  SEQ ID NO:42: pIPSPI site for cloning into Ppzp-RCS2 left+35S P (promoter)+TET repressor (with the "expression control element" embedded)
  SEQ ID NO:43: Short homolog sequence to SEQ ID NO:42+nosP (promoter)+TET operator+siRNA CO+nos T (terminator)
  SEQ ID NO:44: Short homolog sequence to SEQ ID NO:43+ost P (promoter)+FLC+ost T (terminator)+pIPSPI site for cloning into Ppzp-RCS2 right
  SEQ ID NO:45: Short homologous sequence to SEQ ID NO:44+C1 Robisco P (promoter)+DELLA mutant+Robisco T (terminator)+pIPSPI site for cloning in to Ppzp-RCS2 right Different mutations embedded to the "expression control element" and their effect on the control of genes expression and flowering apparent is examined.

"Expression control element"=the regulatory element at the base of the invention describe herby.

Example 7: Use of the ECE Element for Controlling the Expression of Different Resistance Genes in Plants DNA Constructs:
A cassette is designed to serve as a template to control genes expression (SEQ ID NO: 54). The cassette assembled into pPZP (T-DN) plasmid by Gibson assembly, nucleotide 2625 serving as the site for insertion of any gene desired to be regulated.
The cassette includes (SEQ ID NO:54):
  pIPSPI site pPZP-RCS2 Right,
  Gal4VP16 (+SAT-PTC regulatory element)+35St
  UAS promotor+the gene to be regulated (such as herbicide Gens)-35T
  pIPSPI site pPZP-RCS2 Left An example of the gene to be regulated is Enolpyruvyl-shikimate 3-phosphate synthase (EPSPS) enzyme, the target of the herbicide glyphosate.

The sequence of the herbicide tolerant enolpyruvylshikimate 3-phosphate synthase (EPSPS) enzyme (SEQ ID NO:49) can be synthesized and cloned into ECE-cassette using Gibson assembly (SEQ ID NO:56).

Transformed tobacco plants (*Nicotiana benthamiana*) are produced and grown as described hereinabove.

Tobacco plants are tested for glyphosate resistance. Tobacco leaf fragments from plants containing vector alone (PZP-T-DNA) or the PZP-T-DNA+ECE cassette+EPSPS gene are incubated on callus medium containing 0.5 mM glyphosate with or without PEI (final concentration was about 0.0284-0.046 gr per ml). After 10 days, callus growth is examined. Callus growth of leaf fragments of control tobacco and tobacco transfected with the ECE-EPSPS gene, grown on a callus medium containing 0.5 mM glyphosate are expected to be inhibited. Leaf fragments from plants transfected with the ECE-EPSPS gene grown on a callus medium containing 0.5 mM glyphosate with PEI are expected to show glyphosate resistance.

In addition tobacco plants transfected with PZP-T-DNA plasmid with the ECE+the resistance mutant 4-Hydroxyphenylpyruvate dioxygenase gene (SEQ ID NO:52) to form an expression cassette (SEQ ID NO:55) are expected to show resistance to mesotrione herbicides only when grown in a medium with PEI. Plants are visually selected on the basis of a color difference between the transformed plants when subjected to the said herbicide. When grown in MS medium the plant may become and stay white when subjected to the selection procedure, whereas the transformed plants may become white but later turn green, or may remain green when grown in MS+PEI medium.

Example 8: Use of the ECE Element to Manipulate Genome Editing Level

In one example, the ECE regulatory element of the present invention can be used to determine the expression level of the CRISPR-CAS9 complex (Gene Bank Accession No. KF264451) allowing timely editing of the genome. The viral (Px330) CRISPR CAS system can be acquired from "addgene" (plasmid #117919). The ECE regulatory element is synthesized with the sequence of the BseRI restriction site to produce an expression system of the invention having SEQ ID NO:51, and then to be inserted into the 117919 plasmid (SEQ ID NO:57). The ECE sequence is located within the artificial hybrid intron, known to increase transcription levels.

Plasmid was transfected in to F293 cells by Lipofectamine 3000 (L3000015 ThermoFisher) according to the manufacturer instructions. Immediately following transfection cells were incubated with either DMEM or DMEM supplemented with BENZ for 48 hours.

The sgRNA is designed to target the cyclin D1 gene (Accession BC023620) at the Bpu 10I restriction site (sgRNA=agtatttgcataaccctgag, SEQ ID NO:60). The efficiency of the CRISPER assay is determined by extracting the DNA, digesting it with Bpu10I and measuring, by bioanalyser, the ratio between the cut and uncut fragments, uncut indicates an efficient CAS activity.

An increase in CAS activity in cells transfected with the designed ECE-CAS9 plasmid is expected only when the cells are grown in a DMEM medium supplemented with 10 µM BENZ, as indicated by an increase of the uncut fragments.

In additional example, The ECE regulatory element is introduced to gene by CRISPER CAS to determine the targeted gene expression level.

The ECE regulatory element is synthesized with 200nt flacking sequences, homolog to the CCR5 receptor sequence (Accession No. AH005786), within CCR5 intron, forming SEQ ID NO:61

In addition, the sequence of the PmII restriction site is included. ECE element and the CRISPR/Cas plasmid (addgene" plasmid #117919) are cut with PmII and ligated together. Plasmid is transfected in to PBMC cells using standard protocol (lipofectamine) and selected for ECE insertion using NGS analyses. Cells are incubated in CTS™ OpTmizer™ (ThermoFisher A3705001) with or without 50 µM spermin. Cells are then stained with CCR5 antibody (BioLegend 359105) and passed through flow cytometry column to detect the level of CCR5 expression. CCR5 expression is expected to increase in ECE included cells incubated with 50 µM spermin, indicating increase in CRISPER CAS efficiency.

Example 9: Use of the ECE Element for Controlling the Expression of Genes Conferring Insect-Resistance The ECE regulatory element can be used to regulate the expression of genes that encode proteins conferring insecticidal resistance. For example, the Bt (*Bacillus thuringiensis* bacterium) gene that naturally produces crystal-like proteins (Cry proteins), selectively eliminate the harmful moth European corn borer. The Bt gene (Accession No. HM107006) is synthesize with the ECE regulatory element embedded within artificial intron (SEQ ID NO:58) and cloned into the pSB1 plasmid adjacent to the stop codon of the Bt gene, using Gibson assembly (SEQ ID NO:59). Maize cells are transfected as described before to yield transgenic corn plants (U.S. Pat. No. 5,384,253A). The plants are sprayed twice (24 h apart) either with Triton 0.1% or Triton 0.1%+PEI and the expression of Cry protein is measured using Western blot analysis using anti Cry antibody (sigma SAB1401086).

The survival rate of the European corn borer is examined by feeding the moth with corn leaves from plants engineered to include the ECE regulatory element sprayed with Triton 0.1% or Triton 0.1%+PEI. The corn life time is measured.

Example 10: Controlling Lignin Content in Poplar

Lignin polymers are composed of monolignols. Monolignols synthesis occurs in the phenylpropanoid and monolignol biosynthetic pathways. Cinnamoyl-CoA reductase (CCR) is key to monolignol biosynthesis. Down regulation of CCR in poplar has been shown to lead to significant reduction in lignin content in young and mature trees (Boerian W et al., Plant Cell. 2007 November; 19 (11): 3669-3691). Yet, while lower lignin connect is desired in mature trees, it may hinder tree development and resistance to insects and diseases during early stages of development and growth.

*Populus trichocarpa* cv. Trichobel CCR cDNA (Accession No. AJ224986) is cloned in to pTA vector using standard PCR reaction. ECE assembled by Gibson in to the middle CCR gene by introducing artificial intron. The resulted sequence is cloned under a tandem repeat of the CaMV 35S constitutive promoter and is transferred into the binary vector pBIG-HYG conferring resistance to hygromycin. Binary vector is transferred into *Agrobacterium* strain LB4404.

Poplar (*Populus tremula×Populus alba*) plants are transformed by *Agrobacterium* as described (Leplé et al. 1992, Plant Cell Rep. 11:137-141.) Transformants are selected by hygromycin resistance. Transformation is confirmed by molecular analysis of the insertions.

Four-to-five-month old greenhouse-grown trees are sprayed daily with 100 µM BENZ during a period of 6 months. Control, untreated trees and control non-transformed trees are grown without the application of BENZ. At the end of the growth period, all trees are transferred to fresh pots and continue to grow for another 12 months without the application of BENZ.

RT-PCR analysis of CCR is performed at different stages of the growth and development of the trees. Samples of xylem are collected from branches and twigs of selected trees. Total RNA is extracted from tree tissues and RT reactions is performed using the SuperScript II kit (Invitrogen). Quantification of cDNA molecules is performed in five replicates by qPCR machine.

Lignin content is analyzed in samples from different stages of the growth and development of the trees according to Dence, 1992 (Lignin determination. In: Dence C, Lin S, editors. Methods in Lignin Chemistry. Berlin: Springer-Verlag; 1992. pp. 33-61). Lignin is extracted in a thioacidolysis reagent (a mixture of $BF_3$ etherate (Sigma); ethane thiol EtSH (Sigma); and dioxane). Thioacidolysis is performed at 100° C. for 4 hours. The cool mixture is then diluted with water and pH is adjusted to 4.0 with $NaHCO_3$. Lignin is then extracted with $CH_2Cl_2$, dried over $Na_2SO_4$, evaporated under reduced pressure at 40° C., re-dissolved in 1 mL of $CH_2Cl_2$ and analyzed by GC-MS The levels of lignin in transgenic trees which are BENZ-treated are expected to be comparable to wild type plants during early stages of growth and development.

Lignin levels in transgenic trees, upon completion of BENZ treatment cycle, are expected to be comparable to transgenic plants, and lower than wild type plants.

Example 11: Altering Amylose Content in Rice Seeds

High levels of the starch branching IIb gene in rice (SBEIIb, GQ150904.1) are typically linked to lower amylose content. Downregulating the activity of SBEIIb can lead to rice seeds with higher amylose content. The SBEIIb coding sequence is cloned from Nipponbare cDNA into pTA vector using the standard PCR reaction. The resulted clone is manipulated to carry the ECE regulatory element. The resulted altered fragment is closed into rice-transformation vector containing the wHMWG promoter and NOS terminator. The vector also contains the hygromycin resistance gene under the control of the CaMV 35S promoter. The vector is transferred into *Agrobacterium tumefaciens* AGL1.

Nipponbare genetic transformation is carried using hygromycin for selection using a standard transformation protocol (e.g. Upadhyaya et al. Australian Journal of Plant Physiology. 2000; 27:201-210). Transgenic plants are kept in pots and grown to maturity and allowed to set seeds. 1-2 days after flowers emerge, selected transgenic lines are treated with various concentrations of BENZ by spraying rice flowers during anthesis.

RNA is extracted from rice grains, 10 days post anthesis. cDNA is synthesized from 5 µg of total RNA using cDNA syntheses kit. Quantitative real-time PCR is conducted on 100 ng of cDNA using the SBEIIb primers. The expression of SBEIIb in transgenic plants is expected to increase under BENZ treatment.

Protein analysis is conducted on soluble native proteins extracted from rice grains obtained 10 days post anthesis. Proteins are separated on non-denaturation gel and subjected to Western blot analysis using anti-wheat SBEIIb rabbit polyclonal antibodies and goat anti-rabbit immunoglobulins conjugated to HRP. Signals are recorded by automatic film processor. An increase in SBEIIb in transgenic plants activated by BENZ is expected.

Mature panicles are analyzed for their starch content. Fully developed and mature seeds are collected, weighed, dried and ground and total starch is determined using Total Starch HK Assay (Megazyme) and resistant starch is determined using Resistant Starch Assay Kit (Megazyme). The starch content in BENZ-induced transgenic plants is expected to be higher than in non-induced plants.

Example 12: Conditional Expression of Selection Genes

Expression of selection genes is required only during early stages of plant transformation. Following the establishment of a transgenic plant, expression of the selection gene is not required. The hpt gene, conferring resistance to hygromycin, is generated by standard PCR reaction on the pBIGHYG plasmid (binary plasmid) and cloned into pTA vector. The ECE regulatory element is inserted into the hpt gene just after the its ATG start codon by standard Gibson assembly. In addition, the reporting gene GUS: B-glucuronidase is cloned into the pTA vector downstream to the hpt gene under the 35S promoter.

The vector is transferred into *Agrobacterium tumefaciens* EHAP105.

Tobacco genetic transformation is carried using hygromycin as for selection using a standard transformation protocol. 20 µM BENZ is added to the regeneration and selection medium to facilitate the expression of the selection gene. Established transgenic plants are analyzed for GUS expression and selected lines with superior GUS expression are allowed to set seeds. Seeds of heterozygous plants with single insert are selected. Seeds from selected lines cultured on MS-based media supplemented with hygromycin and 10 µM BENZ are expected to develop and survive, while seedlings cultures on medium supplemented with hygromycin alone are expected to fail to develop properly due to inhibition of the hygromycin resistance gene by the ECE element.

Ten days following planting plants transformed to either MS-based media or remained on MS+20 µM BENZ media. Seven day after, RNA is extracted from transgenic plants. cDNA is synthesized from 20 µg of total RNA using cDNA syntheses kit. Quantitative real-time PCR is conducted on 100 ng of cDNA using the hygromycin-encoding gene primers. The expression of hygromycin-encoding gene reduced in the transgenic seedlings when grown on MS media compared to seedling that grow on MS+20 µM BENZ.

Transgene stability and expression of GUS gene is conducted by GUS expression as described above.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. An isolated expression control element (ECE), comprising a polyamine or polyamine analog responsive nucleic acid sequence having the nucleic acid sequence as set forth in SEQ ID NO: 3 flanked at its 5' end and 3' end by splice sites, further comprising at least one intron sequence flanking each of the splice sites, wherein the at least one intron length is from 10 nucleotides to 150 nucleotides.

2. The isolated ECE of claim 1, wherein the flanking splice sites comprise a nucleic acid sequence of a splice acceptor site located 5' to the polyamine or polyamine analog responsive nucleic acid sequence and a nucleic acid sequence of a splice donor site located 3' to the polyamine or polyamine analog responsive nucleic acid sequence.

3. The isolated ECE of claim 2, wherein the ECE splice acceptor site comprises a consecutive nucleotide sequence selected from the group consisting of SEQ ID NO: 4, SEQ ID NO: 15, SEQ ID NO: 32, and functional variants thereof, wherein:
the functional variant of SEQ ID NO: 4 reducing the splicing frequency at the ECE splice acceptor site comprises the nucleic acid sequence set forth in SEQ ID NO:5;
the functional variant of SEQ ID NO: 4 enhancing the splicing frequency at the ECE splice acceptor site comprises the nucleic acid sequence set forth in SEQ ID NO: 6;
the functional variant of SEQ ID NO: 15 reducing the splicing frequency at the ECE splice acceptor site comprises the nucleic acid sequence set forth in SEQ ID NO: 17;
the functional variant of SEQ ID NO: 15 enhancing the splicing frequency at the ECE splice acceptor site comprises the nucleic acid sequence set forth in SEQ ID NO: 16;
the functional variant of SEQ ID NO: 32 reducing the splicing frequency at the ECE splice acceptor site comprises the nucleic acid sequence set forth in SEQ ID NO: 34; and
the functional variant of SEQ ID NO: 32 enhancing the splicing frequency at the ECE splice acceptor site comprises the nucleic acid sequence set forth in SEQ ID NO: 33.

4. The isolated ECE of claim 1, wherein said isolated ECE comprises a nucleic acid sequence set forth in SEQ ID NO: 21; or a nucleic acid sequence set forth in SEQ ID NO: 26; or a nucleic acid sequence set forth in SEQ ID NO: 27; or a nucleic acid sequence set forth in SEQ ID NO: 51; or a nucleic acid sequence set forth in SEQ ID NO: 58.

5. The isolated ECE of claim 1, wherein the at least one intron comprises a chimeric combination of intron nucleic acid sequences and wherein:
a. the chimeric combination comprises the nucleic acid sequence set forth in SEQ ID NO: 22 flanked by the nucleic acid sequence set forth in SEQ ID NO: 23; or b. the chimeric combination comprises the nucleic acid sequence set forth in SEQ ID NO: 24 flanked by the nucleic acid sequence set forth in SEQ ID NO: 25; or c. the chimeric combination comprises the nucleic acid sequence set forth in SEQ ID NO: 22 flanked by the nucleic acid sequence set forth in SEQ ID NO: 30; or d. the chimeric combination comprises the nucleic acid sequence set forth in SEQ ID NO: 24 flanked by the nucleic acid sequence set forth in SEQ ID NO: 31.

6. The isolated ECE of claim 2, wherein the intron is located 5' to the splice acceptor site and wherein said intron sequence comprises a branch point comprising the consecutive nucleotide sequence set forth in SEQ ID NO: 11 or a functional variant thereof, wherein the functional variant of the branch point enhancing the splicing frequency at the splice acceptor site comprises the nucleic acid sequence set forth in SEQ ID NO:13 and wherein the functional variant of the branch point reducing the splicing frequency at the splice acceptor site comprises the nucleic acid sequence set forth in SEQ ID NO:12.

7. A eukaryotic host cell selected from the group consisting of a plant cell, an algal cell, and a fungal cell or an organism comprising same, wherein the eukaryotic host cell comprises a splicing system comprising the isolated ECE of claim 1.

8. The eukaryotic host cell or the organism comprising same of claim 7, wherein the isolated ECE is located within an intron of a transcribable polynucleotide of said host cell.

9. An isolated polynucleotide expression system comprising at least one promoter operably linked to at least one transcribable polynucleotide to be expressed in a host cell, wherein the transcribable polynucleotide comprises the expression control element (ECE) of claim 1, wherein the eukaryotic host cell is selected from the group consisting of a plant cell, an algal cell, and a fungal cell.

10. The isolated polynucleotide expression system of claim 9, wherein the expression control element is located at a position selected from the group consisting of a position between two exons of the transcribable polynucleotide; a position within an intron of the transcribable polynucleotide; a position within an exon of the transcribable polynucleotide; and a position between the promoter and the coding sequence of the transcribable polynucleotide; and a position between the coding sequence of the transcribable polynucleotide and a terminator sequence.

11. The eukaryotic organism of claim 10, wherein said eukaryotic organism is a plant and wherein the transcribable polynucleotide encodes a product conferring resistance to at least one of herbicides, pesticides, and fungicides.

12. A method for regulating the expression of a transcribable polynucleotide within a host cell, the method comprises transforming into the host cell at least one polynucleotide comprising the expression control element (ECE) of claim 1 or a polynucleotide expression system comprising same; and regulating the amount of polyamine or analog thereof to which the host cell is exposed, wherein the eukaryotic host cell is selected from the group consisting of a plant cell, an algal cell, and a fungal cell.

13. The method of claim 12, wherein said method comprises exposing the cell to an effective amount of polyamine or analog thereof, thereby inducing exclusion of the polyamine or polyamine analog-responsive nucleic acid sequence from the transcript of the transcribable polynucleotide.

14. The method of claim 13, wherein exclusion of the polyamine or polyamine analog-responsive nucleic acid sequence results in one of a functional transcript of the transcribable polynucleotide or a non-functional transcript of the transcribable polynucleotide.

15. The method of claim 14, wherein exclusion of the polyamine or polyamine analog-responsive nucleic acid sequence results in a functional transcript of the transcribable polynucleotide, wherein the host cell forms part of a plant, and wherein said transcribable polynucleotide encodes a product conferring resistance to the plant to at least one of a herbicide, a pesticide, or a fungicide.

16. The method of any claim 15, wherein said method further comprises applying to the plant an effective amount of the at least one of a herbicide, a fungicide, or a pesticide.

17. The eukaryotic host cell of claim 7, wherein said eukaryotic host cell is a plant cell.

18. The isolated polynucleotide expression system of claim 9, wherein the eukaryotic host cell is a plant cell.

19. The method of claim 12, wherein the eukaryotic host cell is a plant cell.

* * * * *

SEQUENCE LISTING

```
<160> NUMBER OF SEQ ID NOS: 62

<210> SEQ ID NO 1
<211> LENGTH: 1278
<212> TYPE: DNA
<213> ORGANISM: Mus musculus

<400> SEQUENCE: 1
tgcttcggcg ggctttcatc cttactggtc gcgatctctc cggctccccg tccagggagg      60
agcttctgcg gacttaaaag gcaccgtctt gccacttctt agctgcgcag tttccccgaa     120
gtaagtttgc cagtttctg tcttatactg aggttcgccg ggtcatggtg ccagcctgac     180
tgagaagagg acgctcccgg gaaacgaatg aggaaccacc tcctcctgct gttcaagtac     240
```

```
aggggcctgg tgcgcaaagg gaagaaaagc aaaagacgaa aatggctaaa tttaagatcc      300
gtccagccac tgcctctgac tgcagtgaca tcctgcgact gatcaaggaa ctggctaaat      360
atgaatacat ggaagatcaa gtcattttaa ctgagaaaga tctccaagag gatggctttg      420
gagaacaccc cttctaccac tgcctggttg cagaagtgcc taaagagcac tggacccctg      480
aaggttacag tctctagctt cgccatgtac atggcccttc tgtgtacatg gatgggcggg      540
gaggtaacta aaagaccctt tacacaataa agtagatgat catgataaat gaggacatag      600
cattgttggg ttcgccatgt actatttac ctatgaccca tggattggca agttgctgta       660
tcttgaagac ttcttcgtga tgagtgatta cagaggcttt ggtataggat cagaaatttt       720
gaagaatcta agccaggttg ccatgaagtg tcgctgcagc agtatgcact tcttggtagc      780
agaatggaat gaaccatcta tcaacttcta caaagaaga ggtgcttcgg atctgtccag        840
tgaagaggga tggaggctct tcaagattga caaagagtac ttgctaaaaa tggcagcaga      900
ggagtgaggc gtgccggtgt agacaatgac aacctccatt gtgctttaga ataattctca      960
gcttcccttg ctttctatct tgtgtgtagt gaaataatag agcgagcacc cattccaaag     1020
ctttattacc agtgacgttg ttgcatgttt gaaattcggt ctgtttaaag tggcagtcat     1080
gtatgtggtt tggaggcaga attcttgaac atctttgat gaagaacaag gtggtatgat      1140
cttactatat aagaaaaaca aaacttcatt cttgtgagtc atttaaatgt gtacaatgta     1200
cacactggta cttagagttt ctgttttgat tcttttttttt taaataaaac tactctttga     1260
tttaaatatt cagcctga                                                    1278
```

<210> SEQ ID NO 2
<211> LENGTH: 99
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (10)..(10)
<223> OTHER INFORMATION: n = c, t
<220> FEATURE:
<221> NAME/KEY: misc_feature
<222> LOCATION: (36)..(36)
<223> OTHER INFORMATION: n = c, t
<220> FEATURE:
<221> NAME/KEY: misc_feature
<222> LOCATION: (56)..(57)
<223> OTHER INFORMATION: n = a, g
<220> FEATURE:
<221> NAME/KEY: misc_feature
<222> LOCATION: (71)..(71)
<223> OTHER INFORMATION: n = c, t
<220> FEATURE:
<221> NAME/KEY: misc_feature
<222> LOCATION: (74)..(74)
<223> OTHER INFORMATION: n = t, g
<220> FEATURE:
<221> NAME/KEY: misc_feature
<222> LOCATION: (79)..(79)
<223> OTHER INFORMATION: n = a, t

<400> SEQUENCE: 2

```
tacagtctcn agcttcgcca tgtacatggc ccttcygtgt acatggatgg gcgggnnggt       60
aactaaaaga yccnttacnc aataaagtag atgataaat                              99
```

<210> SEQ ID NO 3
<211> LENGTH: 105
<212> TYPE: DNA
<213> ORGANISM: Artificial Sequence -continued

```
<220> FEATURE:
<223> OTHER INFORMATION: Synthetic polynucleotide

<400> SEQUENCE: 3
tacagtctct agcttcgcca tgtacatggc ccttctgtgt acatggatgg gcggggaggt    60
aactaaaaga ccctttacac aataaagtag atgatcatga taaat                  105

<210> SEQ ID NO 4
<211> LENGTH: 8
<212> TYPE: DNA
<213> ORGANISM: Artificial Sequence
<220> FEATURE:
<223> OTHER INFORMATION: Splicing Sequence

<400> SEQUENCE: 4 cttcaggt                                                             8

<210> SEQ ID NO 5
<211> LENGTH: 8
<212> TYPE: DNA
<213> ORGANISM: Artificial Sequence
<220> FEATURE:
<223> OTHER INFORMATION: Splicing Sequence

<400> SEQUENCE: 5 ctttaggt                                                             8

<210> SEQ ID NO 6
<211> LENGTH: 8
<212> TYPE: DNA
<213> ORGANISM: Artificial Sequence
<220> FEATURE:
<223> OTHER INFORMATION: Splicing Sequence

<400> SEQUENCE: 6 ttgcaggt                                                             8

<210> SEQ ID NO 7
<211> LENGTH: 12
<212> TYPE: DNA
<213> ORGANISM: Artificial Sequence
<220> FEATURE:
<223> OTHER INFORMATION: Splicing Sequence

<400> SEQUENCE: 7
gaggtaaggt cc                                                       12

<210> SEQ ID NO 8
<211> LENGTH: 12
<212> TYPE: DNA
<213> ORGANISM: Artificial Sequence
<220> FEATURE:
<223> OTHER INFORMATION: Splicing Sequence

<400> SEQUENCE: 8
taggtaagtt cc                                                       12

<210> SEQ ID NO 9
<211> LENGTH: 12
<212> TYPE: DNA
<213> ORGANISM: Artificial Sequence
<220> FEATURE:
<223> OTHER INFORMATION: Splicing Sequence

<400> SEQUENCE: 9
```

```
aaggtaagtt cc                                                        12
```

<210> SEQ ID NO 10
<211> LENGTH: 12
<212> TYPE: DNA
<213> ORGANISM: Artificial Sequence
<220> FEATURE:
<223> OTHER INFORMATION: Splicing Sequence

<400> SEQUENCE: 10

```
gaggtaagag tc                                                        12
```

<210> SEQ ID NO 11
<211> LENGTH: 7
<212> TYPE: DNA
<213> ORGANISM: Artificial Sequence
<220> FEATURE:
<223> OTHER INFORMATION: Branch Point

<400> SEQUENCE: 11

```
ctttaat                                                               7
```

<210> SEQ ID NO 12
<211> LENGTH: 7
<212> TYPE: DNA
<213> ORGANISM: Artificial Sequence
<220> FEATURE:
<223> OTHER INFORMATION: Branch Point

<400> SEQUENCE: 12

```
cttttat                                                               7
```

<210> SEQ ID NO 13
<211> LENGTH: 7
<212> TYPE: DNA
<213> ORGANISM: Artificial Sequence
<220> FEATURE:
<223> OTHER INFORMATION: Branch Point

<400> SEQUENCE: 13

```
ctcttat                                                               7
```

<210> SEQ ID NO 14
<211> LENGTH: 4355
<212> TYPE: DNA
<213> ORGANISM: Homo sapiens
<220> FEATURE:
<221> NAME/KEY: misc_feature
<222> LOCATION: (3704)..(3803)
<223> OTHER INFORMATION: n is a, c, g, or t

<400> SEQUENCE: 14

```
tctatttatt tagcaataat agagaaagca tttaagagaa taaagcaatg gaaataagaa     60
atttgtaaat ttccttctga taactagaaa tagaggatcc agtttctttt ggttaaccta    120
aattttattt catttttattg ttttatttta ttttatttta ttttatttta ttttgtgtaa   180
tcgtagtttc agagtgttag agctgaaagg aagaagtagg agaaacatgc aaagtaaaag    240
tataacactt tccttactaa accgacatgg gtttccaggt aggggcagga ttcaggatga    300
ctgacagggc ccttagggaa cactgagacc ctacgctgac ctcataaatg cttgctacct    360
ttgctgtttt aattacatct tttaatagca ggaagcagaa ctctgcactt caaaagtttt    420
tcctcacctg aggagttaat ttagtacaag gggaaaagt acaggggat gggagaaagg     480 cgatcacgtt gggaagctat agagaaagaa gagtaaattt tagtaaagga ggtttaaaca    540
```

```
aacaaaatat aaagagaaat aggaacttga atcaaggaaa tgattttaaa acgcagtatt    600
cttagtggac tagaggaaaa aaataatctg agccaagtag aagacctttt cccctcctac    660
ccctactttc taagtcacag aggcttttg ttcccccaga cactcttgca gattagtcca    720
ggcagaaaca gttagatgtc cccagttaac ctcctatttg acaccactga ttaccccatt    780
gatagtcaca ctttgggttg taagtgactt tttatttatt tgtattttg actgcattaa    840 gaggtctcta gttttttatc tcttgtttcc caaaacctaa taagtaacta atgcacagag    900
cacattgatt tgtatttatt ctatttttag acataattta ttagcatgca tgagcaaatt    960
aagaaaaaca acaacaaatg aatgcatata tatgtatatg tatgtgtgta catatacaca    1020
tatatatata tattttttt cttttcttac cagaaggttt taatccaaat aaggagaaga    1080
tatgcttaga actgaggtag agttttcatc cattctgtcc tgtaagtatt ttgcatattc    1140
tggagacgca ggaagagatc catctacata tcccaaagct gaattatggt agacaaaact    1200
cttccacttt tagtgcatca atttcttatt tgtgtaataa gaaaattggg aaaacgatct    1260
tcaatatgct taccaagctg tgattccaaa tattacgtaa atacacttgc aaaggaggat    1320
gtttttagta gcaatttgta ctgatggtat ggggccaaga gatatatctt agagggaggg    1380
ctgagggttt gaagtccaac tcctaagcca gtgccagaag agccaaggac aggtacggct    1440
gtcatcactt agacctcacc ctgtggagcc acacccctagg gttggccaat ctactcccag    1500
gagcagggag ggcaggagcc agggctgggc ataaaagtca gggcagagcc atctattgct    1560
tacatttgct tctgacacaa ctgtgttcac tagcaacctc aaacagacac catggtgcac    1620
ctgactcctg aggagaagtc tgccgttact gccctgtggg gcaaggtgaa cgtggatgaa    1680
gttggtggtg aggccctggg caggttggta tcaaggttac aagacaggtt taaggagacc    1740
aatagaaact gggcatgtgg agacagagaa gactcttggg tttctgatag gcactgactc    1800
tctctgccta ttggtctatt tcccacccct taggctgctg gtggtctacc cttggaccca    1860
gaggttcttt gagtcctttg gggatctgtc cactcctgat gctgttatgg gcaaccctaa    1920
ggtgaaggct catggcaaga aagtgctcgg tgcctttagt gatggcctgg ctcacctgga    1980
caacctcaag ggcacctttg ccacactgag tgagctgcac tgtgacaagc tgcacgtgga    2040
tcctgagaac ttcagggtga gtctatggga cccttgatgt tttctttccc cttcttttct    2100
atggttaagt tcatgtcata ggaagggag aagtaacagg gtacagttta gaatgggaaa    2160
cagacgaatg attgcatcag tgtggaagtc tcaggatcgt tttagtttct tttattgct    2220 gttcataaca attgttttct tttgtttaat tcttgctttc ttttttttc ttctccgcaa    2280 tttttactat tatacttaat gccttaacat tgtgtataac aaaaggaaat atctctgaga    2340
tacattaagt aacttaaaaa aaactttac acagtctgcc tagtacatta ctatttggaa    2400
tatatgtgtg cttatttgca tattcataat ctccctactt tatttctttt tattttaat    2460 tgatacataa tcattataca tatttatggg ttaaagtgta atgttttaat atgtgtacac    2520
atattgacca aatcagggta attttgcatt tgtaatttta aaaaatgctt tcttcttta    2580 atatactttt ttgttatct tatttctaat actttcccta atctctttct ttcagggcaa    2640
taatgataca atgtatcatg cctctttgca ccattctaaa gaataacagt gataatttct    2700
gggttaaggc aatagcaata tttctgcata taaatatttc tgcatataaa ttgtaactga    2760
tgtaagaggt tcatattgc taatagcagc tacaatccag ctaccattct gctttattt    2820 tatggttggg ataaggctgg attattctga gtccaagcta ggccctttg ctaatcatgt    2880
```

```
tcatacctct tatcttcctc ccacagctcc tgggcaacgt gctggtctgt gtgctggccc    2940
atcactttgg caaagaattc accccaccag tgcagccaca cctatcagtg gtgtggctaa    3000
tgccctggcc cacaagtatc actaagctcg ctttcttgct gtccaatttc tattaaaggt    3060
tcctttgttc cctaagtcca actactaaac tgggggatat tatgaagggc cttgagcatc    3120
tggattctgc ctaataaaaa acatttattt tcattgcaat gatgtattta aattattct     3180 gaatatttta ctaaaaggg aatgtgggag gtcagtgcat ttaaaacata agaaatgaa      3240 gagctagttc aaaccttggg aaaatacact atatcttaaa ctccatgaaa gaaggtgagg    3300
ctgcaaacag ctaatgcaca ttggcaacag ccctgatgcc tatgccttat tcatccctca    3360
gaaaaggatt caagtagagg cttgatttgg aggttaaagt tttctatgct gtattttaca    3420
ttacttattg ttttagctgt cctcatgaat gtcttttcac tacccatttg cttatcctgc    3480
atctctcagc cttgactcca ctcagttctc ttgcttagag ataccacctt tcccctgaag    3540
tgttccttcc atgttttacg gcgagatggt ttctcctcgc ctggccactc agccttagtt    3600
gtctctgttg tcttatagag gtctacttga agaaggaaaa acaggggca cggttttgact   3660 gtcctgtgag cccttcttcc ctgcctcccc cactcacagt gacnnnnnnn nnnnnnnnn    3720 nnnnnnnnnn nnnnnnnnnn nnnnnnnnnn nnnnnnnnnn nnnnnnnnnn nnnnnnnnnn    3780
nnnnnnnnnn nnnnnnnnnn nnntctgcat ataaattgta actgatgtaa gaggtttcat    3840
attgctaata gcagctacaa tccagctacc attctgcttt tattttatgg ttgggataag    3900
gctggattat tctgagtcca agctaggccc ttttgctaat catgttcata cctcttatct    3960
tcctcccaca gctcctgggc aacgtgctgg tctgtgtgct ggcccatcac tttggcaaat    4020
aattcacccc accagtgcag gctgcctatc agaaagtggt ggctggtgtg gctaatgccc    4080
tggcccacaa gtatcactaa gctcgctttc ttgctgtcca atttctatta aaggttcctt    4140
tgttccctaa gtccaactac taaactgggg gatattatga agggccttga gcatctggat    4200
tctgcctaat aaaaaacatt tattttcatt gcaatgatgt atttaaatta tttctgaata    4260
ttttactaaa aagggaatgt gggaggtcag tgcatttaaa acataaagaa atgaagagct    4320
agttcaaacc ttgggaaaat acactatatc ttaaa                              4355

<210> SEQ ID NO 15
<211> LENGTH: 11
<212> TYPE: DNA
<213> ORGANISM: Artificial Sequence
<220> FEATURE:
<223> OTHER INFORMATION: Splicing Sequence

<400> SEQUENCE: 15 cccacccctta g                                                          11

<210> SEQ ID NO 16
<211> LENGTH: 11
<212> TYPE: DNA
<213> ORGANISM: Artificial Sequence
<220> FEATURE:
<223> OTHER INFORMATION: Splicing Sequence

<400> SEQUENCE: 16
cccacccgca g                                                           11

<210> SEQ ID NO 17
<211> LENGTH: 11
<212> TYPE: DNA
<213> ORGANISM: Artificial Sequence
```

```
<220> FEATURE:
<223> OTHER INFORMATION: Splicing Sequence

<400> SEQUENCE: 17
ccccccctta g                                                            11

<210> SEQ ID NO 18
<211> LENGTH: 12
<212> TYPE: DNA
<213> ORGANISM: Artificial Sequence
<220> FEATURE:
<223> OTHER INFORMATION: Splicing Sequence

<400> SEQUENCE: 18
ggcggttggt at                                                           12

<210> SEQ ID NO 19
<211> LENGTH: 12
<212> TYPE: DNA
<213> ORGANISM: Artificial Sequence
<220> FEATURE:
<223> OTHER INFORMATION: Splicing Sequence

<400> SEQUENCE: 19
aagggttggt at                                                           12

<210> SEQ ID NO 20
<211> LENGTH: 12
<212> TYPE: DNA
<213> ORGANISM: Artificial Sequence
<220> FEATURE:
<223> OTHER INFORMATION: Splicing Sequence

<400> SEQUENCE: 20
ggcggttgtt at                                                           12

<210> SEQ ID NO 21
<211> LENGTH: 312
<212> TYPE: DNA
<213> ORGANISM: Artificial Sequence
<220> FEATURE:
<223> OTHER INFORMATION: Synthetic Polynucleotide

<400> SEQUENCE: 21
gtttcataaa atggtttttg tttgacccta acctaactt tttttttttt gtaattgtgt         60
taaatcacat tttttctt aatttgtccc aatcttcagg ttacagtctc tagcttcgcc         120
atgtacatgg cccttctgtg tacatggatg ggcggggagg taactaaaag acccttaca        180 caataaagta gatgatcatg ataaatgagg taagagtcta ttatcgcaca cttaaaacac       240
agtagatcag aaattattt tcgcttcctg tctgtctgca agaaataca aaatggctag         300 aaaatttaag at                                                          312

<210> SEQ ID NO 22
<211> LENGTH: 99
<212> TYPE: DNA
<213> ORGANISM: Artificial Sequence
<220> FEATURE:
<223> OTHER INFORMATION: Synthetic Polynucleotide

<400> SEQUENCE: 22
gtttcataaa atggtttttg tttgacccta acctaactt tttttttttt gtaattgtgt         60
taaatcacat tttttctt aatttgtccc aatcttcag                                99
```

<210> SEQ ID NO 23
<211> LENGTH: 92
<212> TYPE: DNA
<213> ORGANISM: Artificial Sequence
<220> FEATURE:
<223> OTHER INFORMATION: Synthetic Polynucleotide

<400> SEQUENCE: 23

```
gttggtatca aggttacaag acaggtttaa ggagaccaat agaaactggg catgtggaga      60
cagagaagac tcttgggttt ctgatagggc cc                                    92
```

<210> SEQ ID NO 24
<211> LENGTH: 103
<212> TYPE: DNA
<213> ORGANISM: Artificial Sequence
<220> FEATURE:
<223> OTHER INFORMATION: Synthetic Polynucleotide

<400> SEQUENCE: 24

```
gtaaggtcct attatcgcac acttaaaaca cagtagatca gaaatttatt ttcgcttcct      60
gtctgtctgc aaagaaatac aaaatggcta gaaaatttaa gat                       103
```

<210> SEQ ID NO 25
<211> LENGTH: 85
<212> TYPE: DNA
<213> ORGANISM: Artificial Sequence
<220> FEATURE:
<223> OTHER INFORMATION: Synthetic Polynucleotide

<400> SEQUENCE: 25

```
ctgggcatgt ggagacagag aagactcttg ggtttctgat aggcactgac tctctctgcc      60
tattggtcta ttttcccacc cttag                                            85
```

<210> SEQ ID NO 26
<211> LENGTH: 312
<212> TYPE: DNA
<213> ORGANISM: Artificial Sequence
<220> FEATURE:
<223> OTHER INFORMATION: Synthetic Polynucleotide

<400> SEQUENCE: 26

```
gtttcataaa atggtttttg tttgacccta acctaacttt ttttttttttt gtaattgtgt     60 taaatcacat ttttttcttt aatttgtccc aatcttcagg ttacagtctc tagcttcgcc    120
atgtacatgg cccttctgtg tacatggatg ggcggggagg taactaaaag acccttcaca    180
caataaagta gatgatcatg ataaatgagg taaggtccta ttatcgcaca cttaaaacac    240
agtagatcag aaatttattt tcgcttcctg tctgtctgca aagaaataca aaatggctag    300
aaaatttaag at                                                        312
```

<210> SEQ ID NO 27
<211> LENGTH: 287
<212> TYPE: DNA
<213> ORGANISM: Artificial Sequence
<220> FEATURE:
<223> OTHER INFORMATION: Synthetic Polynucleotide

<400> SEQUENCE: 27

```
gttggtatca aggttacaag acaggtttaa ggagaccaat agaaactggg catgtggaga     60
cagagaagac tcttgggttt ctgatagggc ccgttacagt ctctagcttc gccatgtaca   120
tggcccttct gtgtacatgg atgggcgggg aggtaactaa aagaccctt acacaataaa    180
```

```
gtagatgatc atgataaatg agctgggcat gtggagacag agaagactct tgggtttctg    240
ataggcactg actctctctg cctattggtc tattttccca cccttag                  287
```

<210> SEQ ID NO 28
<211> LENGTH: 171
<212> TYPE: PRT
<213> ORGANISM: Mus musculus

<400> SEQUENCE: 28

```
Met Ala Lys Phe Lys Ile Arg Pro Ala Thr Ala Ser Asp Cys Ser Asp
1               5                   10                  15

Ile Leu Arg Leu Ile Lys Glu Leu Ala Lys Tyr Glu Tyr Met Glu Asp
            20                  25                  30

Gln Val Ile Leu Thr Glu Lys Asp Leu Gln Glu Asp Gly Phe Gly Glu
        35                  40                  45

His Pro Phe Tyr His Cys Leu Val Ala Glu Val Pro Lys Glu His Trp
    50                  55                  60

Thr Pro Glu Gly His Ser Ile Val Gly Phe Ala Met Tyr Tyr Phe Thr
65                  70                  75                  80

Tyr Asp Pro Trp Ile Gly Lys Leu Leu Tyr Leu Glu Asp Phe Phe Val
                85                  90                  95

Met Ser Asp Tyr Arg Gly Phe Gly Ile Gly Ser Glu Ile Leu Lys Asn
            100                 105                 110

Leu Ser Gln Val Ala Met Lys Cys Arg Cys Ser Ser Met His Phe Leu
        115                 120                 125

Val Ala Glu Trp Asn Glu Pro Ser Ile Asn Phe Tyr Lys Arg Arg Gly
    130                 135                 140

Ala Ser Asp Leu Ser Ser Glu Glu Gly Trp Arg Leu Phe Lys Ile Asp
145                 150                 155                 160

Lys Glu Tyr Leu Leu Lys Met Ala Ala Glu Glu
                165                 170
```

<210> SEQ ID NO 29
<211> LENGTH: 2082
<212> TYPE: DNA
<213> ORGANISM: Artificial Sequence
<220> FEATURE:
<223> OTHER INFORMATION: Synthetic Polynucleotide

<400> SEQUENCE: 29

```
gtaaatttct agttttctc cttcattttc ttggttagga ccctttttctc tttttatttt    60 tttgagcttt gatctttctt taaactgatc tatttttaa ttgattggtt atggtgtaaa    120
tattacatag ctttaactga taatctgatt actttatttc gtgtgtctat gatgatgatg    180
atagttacag aaccgacgac tcgtccgtcc tgtagaaacc ccaacccgtg aaatcaaaaa    240
actcgacggc ctgtgggcat tcagtctgga tcgcgaaaac tgtggaattg atcagcgttg    300
gtgggaaagc gcgttacaag aaagccgggc aattgctgtg ccaggcagtt ttaacgatca    360
gttcgccgat gcagatattc gtaattatgc gggcaacgtc tggtatcagc gcgaagtctt    420
tataccgaaa ggttgggcag ccagcgtat cgtgctgcgt ttcgatgcgg tcactcatta    480
cggcaaagtg tgggtcaata atcaggaagt gatggagcat cagggcggct atacgccatt    540
tgaagccgat gtcacgccgt atgttattgc cgggaaaagt gtacgtatca ccgtttgtgt    600
gaacaacgaa ctgaactggc agactatccc gccgggaatg gtgattaccg acgaaaacgg    660
caagaaaaag cagtcttact tccatgattt ctttaactat gccggaatcc atcgcagcgt    720
```

-continued

```
aatgctctac accacgccga acacctgggt ggacgatatc accgtggtga cgcatgtcgc      780
gcaagactgt aaccacgcgt ctgttgactg caggtggtg gccaatggtg atgtcagcgt      840
tgaactgcgt gatgcggatc aacaggtggt tgcaactgga caaggcacta gcgggacttt      900
gcaagtggtg aatccgcacc tctggcaacc gggtgaaggt tatctctatg aactcgaagt      960
cacagccaaa agccagacag agtctgatat ctacccgctt cgcgtcggca tccggtcagt     1020
ggcagtgaag ggccaacagt tcctgattaa ccacaaaccg ttctacttta ctggctttgg     1080
tcgtcatgaa gatgcggact acgtggcaa aggattcgat aacgtgctga tggtgcacga     1140
ccacgcatta atggactgga ttggggccaa ctcctaccgt acctcgcatt accttacgc      1200 tgaagagatg ctcgactggg cagatgaaca tggcatcgtg gtgattgatg aaactgctgc     1260
tgtcggcttt cagctgtctt taggcattgg tttcgaagcg ggcaacaagc cgaaagaact     1320
gtacagcgaa gaggcagtca cggggaaac tcagcaagcg cacttacagg cgattaaaga     1380
gctgatagcg cgtgacaaaa accacccaag cgtggtgatg tggagtattg ccaacgaacc     1440
ggatacccgt ccgcaaggtg cacgggaata tttcgcgcca ctggcggaag caacgcgtaa     1500
actcgacccg acgcgtccga tcacctgcgt caatgtaatg ttctgcgacg ctcacaccga     1560
taccatcagc gatctctttg atgtgctgtg cctgaaccgt tattacggat ggtatgtcca     1620
aagcggcgat ttggaaacgg cagagaaggt actggaaaaa gaacttctgg cctggcagga     1680
gaaactgcat cagccgatta tcatcaccga atacggcgtg gatacgttag ccgggctgca     1740
ctcaatgtac accgacatgt ggagtgaaga gtatcagtgt gcatggctgg atatgtatca     1800 ccgcgtctt gatcgcgtca gcgccgtcgt cggtgaacag gtatggaatt cgccgatt      1860 tgcgacctcg caaggcatat tgcgcgttgg cggtaacaag aaaggggatct tcactcgcga     1920 ccgcaaaccg aagtcggcgg ctttctgct gcaaaaacgc tggactggca tgaacttcgg     1980
tgaaaaaccg cagcagggag gcaaacaagc tagccaccac caccaccacc acgtgtgaat     2040
tacaggtgac cagctcgaat ttccccgatc gttcaaggat cc                        2082
```

<210> SEQ ID NO 30
<211> LENGTH: 102
<212> TYPE: DNA
<213> ORGANISM: Artificial Sequence
<220> FEATURE:
<223> OTHER INFORMATION: Synthetic Polynucleotide

<400> SEQUENCE: 30

```
gtaaatttct agttttctc cttcatttc ttggttagga ccctttctc tttttatttt       60 tttgagcttt gatctttctt taaactgatc tattttttaa tt                        102
```

<210> SEQ ID NO 31
<211> LENGTH: 88
<212> TYPE: DNA
<213> ORGANISM: Artificial Sequence
<220> FEATURE:
<223> OTHER INFORMATION: Synthetic Polynucleotide

<400> SEQUENCE: 31

```
gattggttat ggtgtaaata ttacatagct ttaactgata atctgattac tttatttcgt      60
gtgtctatga tgatgatgat agttacag                                         88
```

<210> SEQ ID NO 32
<211> LENGTH: 10
<212> TYPE: DNA

```
<213> ORGANISM: Artificial Sequence
<220> FEATURE:
<223> OTHER INFORMATION: Splicing Sequence

<400> SEQUENCE: 32
atagttacag                                                            10

<210> SEQ ID NO 33
<211> LENGTH: 9
<212> TYPE: DNA
<213> ORGANISM: Artificial Sequence
<220> FEATURE:
<223> OTHER INFORMATION: Splicing Sequence

<400> SEQUENCE: 33 tttttgcag                                                              9

<210> SEQ ID NO 34
<211> LENGTH: 8
<212> TYPE: DNA
<213> ORGANISM: Artificial Sequence
<220> FEATURE:
<223> OTHER INFORMATION: Splicing Sequence

<400> SEQUENCE: 34 agttatag                                                               8

<210> SEQ ID NO 35
<211> LENGTH: 12
<212> TYPE: DNA
<213> ORGANISM: Artificial Sequence
<220> FEATURE:
<223> OTHER INFORMATION: Splicing Sequence

<400> SEQUENCE: 35
gagggtaaat tt                                                         12

<210> SEQ ID NO 36
<211> LENGTH: 11
<212> TYPE: DNA
<213> ORGANISM: Artificial Sequence
<220> FEATURE:
<223> OTHER INFORMATION: Splicing Sequence

<400> SEQUENCE: 36
aaggtaagtt t                                                          11

<210> SEQ ID NO 37
<211> LENGTH: 11
<212> TYPE: DNA
<213> ORGANISM: Artificial Sequence
<220> FEATURE:
<223> OTHER INFORMATION: Splicing Sequence

<400> SEQUENCE: 37
aaagtaaatt t                                                          11

<210> SEQ ID NO 38
<211> LENGTH: 591
<212> TYPE: DNA
<213> ORGANISM: Arabidopsis thaliana

<400> SEQUENCE: 38
atgggaagaa aaaaactaga aatcaagcga attgagaaca aaagtagccg acaagtcacc      60
ttctccaaac gtcgcaacgg tctcatcgag aaagctcgtc agctttctgt tctctgtgac     120
```

```
gcatccgtcg ctcttctcgt cgtctccgcc tccggcaagc tgtacagctt ctcctccggc    180
gataacctgg tcaagatcct tgatcgatat gggaaacagc atgctgatga tcttaaagcc    240
ttggatcatc agtcaaaagc tctgaactat ggttcacact atgagctact tgaacttgtg    300
gatagcaagc ttgtgggatc aaatgtcaaa aatgtgagta tcgatgctct tgttcaactg    360
gaggaacacc ttgagactgc cctctccgtg actagagcca agaagaccga actcatgttg    420
aagcttgttg agaatcttaa agaaaaggag aaaatgctga agaagagaa ccaggttttg    480 gctagccaga tggagaataa tcatcatgtg ggagcagaag ctgagatgga gatgtcacct    540
gctggacaaa tctccgacaa tcttccggtg actctcccac tacttaatta g             591
```

<210> SEQ ID NO 39
<211> LENGTH: 1716
<212> TYPE: DNA
<213> ORGANISM: Solanum lycopersicum.

<400> SEQUENCE: 39

```
atgaagagag atcgagatcg agatcgagaa agagagaaaa gagcattctc taatggtgct     60
gtttcttcag ggaaaagtaa gatttgggaa gaagatgaag aagaaaaacc agatgctgga    120
atggatgttg ctcaaaaact tgaacagctt gagatggcta tgggtacaac gatggaagat    180
ggtattactc atcttcctac tgataccgtt cataaaaacc catctgatat ggctggttgg    240
gtacaaagta tgttatcttc gatttcgaca aactttgata tgtgtaatca ggaaaacgat    300
gtgcttgtat ctggttgtgg ttcttcttct tctataatcg atttctcaca aaatcatcga    360
acaagtacca tttctgatga tgatttaaga gctatacctg tggtgctgt tttcaattcg    420 gatagtaata aaagacacag atcaacaact tctagttttt caactacatc ctcatctatg    480
gtgacagatt catcagcaac gagacctgtt gtactagttg attcacaaga actgggggtt    540
cgtcttgttc atactttaat ggcgtgtgct gaagctgtac aacagaaaa tttaactta     600 gcggatcaac ttgttagaca tattggtatt cttgcggttt cacaatctgg tgctatgaga    660
aaagttgcta cttactttgc tgaagcatta gcaagaagaa tctacaaaat ttatccacaa    720
gattcaatgg aatcatcata tacagatgtt ttacaaatgc atttctatga acttgccct    780 tatctcaaat tcgctcattt tactgctaat caagccattc ttgaagcgtt tacaggttgt    840
aacaaagttc atgtaattga tttcagctta aaacagggta gcaatggcc tgcacttatg    900 caagctttag ctttacgccc cggtggacct ccggcattta gactcaccgg aatcggacct    960
ccacagccgg ataacacaga tgccttgcaa caagttggat ggaagttggc tcagttagcg   1020
gaaactattg ggttgaatt tgaattcagg ggatttgttg ctaattcgtt agcagatctt   1080
gatgcgacta tacttgatat aaggccaagt gaaactgaag cagtagctat aaactctgtt   1140
tttgagcttc atcgattgtt atcccggccg ggagcaattg aaaaagtgtt gaactctatt   1200
aaacagatta cccgaagat tgttactctt gttgagcaag aagcgaatca taacgcaggg   1260
gtttttattg atagatttaa cgaagctttg cattattact caaccatgtt tgattcgtta   1320
gaaagctctg gtcttcgtc ttcagcttca ccaactggga ttcttcctca acctccggtg   1380
aacaatcaag atttggtgat gtcggaggtt tatttaggga cagatttg taacgtggtg   1440 gcttgtgaag gttcagatcg agttgaacga catgaaacac tgaatcaatg gagggttagg   1500
atgaactcat ctgggttcga tccggttcat ctgggttcaa atgcgttcaa acaagcttcc   1560
atgcttttag ctctgttcgc cggcggcgat ggttacaggg tggaagaaaa cgatgggtgt   1620
```

```
cttatgttgg ggtggcatac acggccactt atagctacct ccgcctggaa gctattgccg    1680
gactccggca ccggcgccgg agaagtcgag ttgtaa                              1716

<210> SEQ ID NO 40
<211> LENGTH: 987
<212> TYPE: DNA
<213> ORGANISM: Artificial Sequence
<220> FEATURE:
<223> OTHER INFORMATION: Synthetic Polynucleotide

<400> SEQUENCE: 40
taaaatttct aattcctaaa accaaaatcc agtgaccggt gatcatgagc ggagaattaa      60
gggagtcacg ttatgacccc cgccgatgac gcgggacaag ccgttttacg tttggaactg     120
acagaaccgc aacgttgaag gagccactca gccgcgggtt tctggagttt aatgagctaa     180
gcacatacgt cagaaaccat tattgcgcgt tcaaaagtcg cctaaggtca ctatcagcta     240
gcaaatattt cttgtcaaaa atgctccact gacgttccat aaattcccct cggtatccaa     300
ttagagtctc atattcactc tcaatagatc cttcgtcttc actcgagttt accactccct     360
atcagtgata gagaaaagtg aaagtcgagt ttaccactcc ctatcagtga tagagaaaag     420
tgaaagtcga gtttaccact ccctatcagt gatagagaaa agtgaaagtc gagtttacca     480
ctccctatca gtgatagaga aaagtgaaag tcgagtttac cactccctat cagtgataga     540
gaaaagtgaa agtcgagttt accactccct atcagtgata gagaaaagtg aaagtcgagt     600
ttaccactcc ctatcagtga tagagaaaag tgaaagtcgg gctcggttcc cgggtcgaga     660
tataatattg taccttacat cattatcaat ttttttgata atgatgtaag gtacaatatt     720
cccgatcgtt caaacatttg gcaataaagt ttcttaagat tgaatcctgt tgccggtctt     780
gcgatgatta tcatataatt tctgttgaat tacgttaagc atgtaataat taacatgtaa     840
tgcatgacgt tatttatgag atgggttttt atgattagag tcccgcaatt atacatttaa     900
tacgcgatag aaaacaaaat atagcgcgca aactaggata aattatcgcg cgcggtgtca     960
tctatgttac tagatcgggg cggccgc                                         987

<210> SEQ ID NO 41
<211> LENGTH: 3456
<212> TYPE: DNA
<213> ORGANISM: Artificial Sequence
<220> FEATURE:
<223> OTHER INFORMATION: Synthetic Polynucleotide

<400> SEQUENCE: 41
taactataac ggtcctaagg tagcgatggc aaacagctat tatgggtatt atgggtcaac      60
atgtggagca cgacacactt gtctactcca aaaatatcaa agatacagtc tcagaagacc     120
aaagggcaat tgagactttt caacaagggg taatatccgg aaacctcctc ggattccatt     180
gcccagctat ctgtcacttt attgtgaaga gtggaaaaag gaaggtggct cctacaaatg     240 ccatcattg cgataaagga aaggccatcg ttgaagatgc ctctgccgac agtggtccca     300
aagatggacc cccacccacg aggagcatcg tggaaaaaga gacgttccaa ccacgtcttc     360 aaagcaagt ggattgatgt gataacatgg tggagcacga cacttgtc tactccaaaa     420 atatcaaaga tacagtctca gaagaccaaa gggcaattga cttttcaa caagggtaa     480 tatccggaaa cctcctcgga ttccattgcc cagctatctg tcactttatt gtgaagatag     540
tggaaaagga aggtggctcc tacaaatgcc atcattgcga taaaggaaag gccatcgttg     600
aagatgcctc tgccgacagt ggtcccaaag atggaccccc acccacgagg agcatcgtgg     660
```

```
aaaaagaaga cgttccaacc acgtcttcaa agcaagtgga ttgatgtgat atctccactg     720
acgtaaggga tgacgcacaa tcccactatc cttcgcaaga cccttcctct atataaggaa     780
gttcatttca tttggagagg acgtcgagag ttctcaacac aacatataca aaacaaacga     840
atctcaagca atcaagcatt ctacttctat tgcagcaatt taaatcattt cttttaaagc     900
aaaagcaatt ttctgaaaat tttcaccatt tacgaacgat agtgaatttt atggtaagtt     960
cctgggcggt tggtatcaag gttacaagac aggtttaagg agaccaatag aaactgggca    1020
tgtggagaca gagaagactc ttgggtttct gatggggccc gtttcataaa atggtttttg    1080
tttgacccta acctaacttt tttttttttt gtaattgtgt taaatcacat ttttttcttt    1140
aatttgtccc aatcttcagg ttacagtctc tagcttcgcc atgtacatgg cccttctgtg    1200
tacatggatg ggcggggagg taactaaaag accctttaca caataaagta gatgatcatg    1260
ataaatgagg taaggtccta ttatcgcaca cttaaaacac agtagatcag aaatttattt    1320
tcgcttcctg tctgtctgca aagaaataca aaatggctag aaaatttaag atctgggcat    1380
gtggagacag agaagactct tgggtttctg ataggcactg actctctctg cctattggtc    1440
tattttccca tttgcagaag ctcctgtcct ccatcgagca ggcctgcgac atctgccgcc    1500
tcaagaagct caagtgctcc aaggagaagc cgaagtgcgc caagtgtctg aagaacaact    1560
gggagtgtcg ctactctccc aaaccaagc gctccccgct gacccgcgcc cacctcaccg    1620
aagtggagtc ccgcctggag cgcctggagc agctcttcct cctgatcttc cctcgagagg    1680
acctcgacat gatcctgaaa atggactccc tccaggacat caaagccctg ctcaccggcc    1740
tcttcgtcca ggacaacgtg aacaaagacg ccgtcaccga ccgcctggcc tccgtggaga    1800
ccgacatgcc cctcacccta cgccagcacc gcatcagcgc gacctcctcc tcggaggaga    1860
gcagcaacaa gggccagcgc cagttgaccg tctcgacggc cccccccgacc gacgtcagcc    1920 tgggggacga gctccactta gacggcgagg acgtggcgat ggcgcatgcc gacgcgctag    1980
acgatttcga tctggacatg ttgggggacg gggattcccc ggggccggga tttacccccc    2040
acgactccgc cccctacggc gctctggata tggccgactt cgagtttgag cagatgtttA    2100
ccgatgccct tggaattgac gagtacggtg ggtaggtccg caaaaatcac cagtctctct    2160
ctacaaatct atctctctct atttttctcc agaataatgt gtgagtagtt cccagataag    2220
ggaattaggg ttcttatagg gtttcgctca tgtgttgagc atataagaaa cccttagtat    2280
gtatttgtat ttgtaaaata cttctatcaa taaaatttct aattcctaaa accaaaatcc    2340
agtgacggac tgtagaggtt ccgggtgaca gccctccgac gggtgacagc cctccgacgg    2400
gtgacagccc tccgaattct agaggatccg ggtgacagcc ctccgacggg tgacagccct    2460
ccgacgggtg acagccctcc gaattcgagc tcggtacccg ggatctgtc gacctcgatc    2520 gagatcttcg caagacccctt cctctatata aggaagttca tttcatttgg agaggacacg    2580
ctgaaatggg gccaaaaaag aagagaaagg tagaagaccc cgtctctaga ttagataaaa    2640
gtaaagtgat taacagcgca ttagagctac ttaatgaggt cggaatcgaa ggtttaacaa    2700
cccgtaaact cgcccagaag ctaggtgtag agcagcctac attgtattgg catgtaaaaa    2760
ataagcgggc tttgctcgac gccttagcca ttgagatgtt agataggcac catactcact    2820
tttgcccttt agaaggggaa agctggcaag atttttttacg taataacgct aaaagtttta    2880
gatgtgcttt actaagtcat cgcgatggag caaaagtaca tttaggtaca cggcctacag    2940
aaaaacagta tgaaactctc gaaaatcaat tagccttttt atgccaacaa ggtttttcac    3000
```

```
tagagaatgc attatatgca ctcagcgctg tggggcattt tactttaggt tgcgtattgg    3060
aagatcaaga gcatcaagtc gctaaagaag aaagggaaac acctactact gatagtatgc    3120
cgccattatt acgacaagct atcgaattat ttgatcacca aggtgcagag ccagccttct    3180
tattcggcct tgaattgatc atatgcggat tagaaaaaca acttaaatgt gaaagtgggt    3240
cttaggtccg caaaaatcac cagtctctct ctacaaatct atctctctct attttttctcc   3300 agaataatgt gtgagtagtt cccagataag ggaattaggg ttcttatagg gtttcgctca    3360
tgtgttgagc atataagaaa ccccttagtat gtatttgtat ttgtaaaata cttctatcaa   3420
taaaatttct aattcctaaa accaaaatcc agtgac                              3456

<210> SEQ ID NO 42
<211> LENGTH: 2350
<212> TYPE: DNA
<213> ORGANISM: Artificial Sequence
<220> FEATURE:
<223> OTHER INFORMATION: Synthetic Polynucleotide

<400> SEQUENCE: 42
taactataac ggtcctaagg tagcgatggc aaacagctat tatgggtatt atgggtcaac      60
atgtggagca cgacacactt gtctactcca aaaatatcaa agatacagtc tcagaagacc    120
aaagggcaat tgagactttt caacaaaggg taatatccgg aaacctcctc ggattccatt    180
gcccagctat ctgtcacttt attgtgaaga gagtggaaaa ggaaggtggc tcctacaaat    240
gccatcattg cgataaagga aaggccatcg ttgaagatgc ctctgccgac agtggtccca    300
aagatggacc cccacccacg aggagcatcg tggaaaaaga agacgttcca accacgtctt    360
caaagcaagt ggattgatgt gataacatgg tggagcacga cacttgtc tactccaaaa      420 atatcaaaga tacagtctca gaagaccaaa gggcaattga acttttcaa caaagggtaa    480 tatccggaaa cctcctcgga ttccattgcc cagctatctg tcactttatt gtgaagatag    540
tggaaaagga aggtggctcc tacaaatgcc atcattgcga taaaggaaag gccatcgttg    600
aagatgcctc tgccgacagt ggtcccaaag atggaccccc acccacgagg agcatcgtgg    660
aaaaagaaga cgttccaacc acgtcttcaa agcaagtgga ttgatgtgat atctccactg    720
acgtaaggga tgacgcacaa tcccactatc cttcgcaaga cccttcctct atataaggaa    780
gttcatttca tttggagagg acgtcgagag ttctcaacac aacatataca aaacaaacga    840
atctcaagca atcaagcatt ctacttctat tgcagcaatt taaatcattt cttttaaagc    900
aaaagcaatt ttctgaaaat tttcaccatt tacgaacgat agtgaatttt atggtaagtt    960
cctgggcggt tggtatcaag gttacaagac aggtttaagg agaccaatag aaactgggca   1020
tgtggagaca gagaagactc ttgggtttct gatgggcc gtttcataaa atggttttg      1080 tttgacccta acctaacttt tttttttttt gtaattgtgt taaatcacat ttttttcttt    1140
aatttgtccc aatcttcagg ttacagtctc tagcttcgcc atgtacatgg cccttctgtg   1200
tacatggatg ggcggggagg taactaaaag acccctttaca caataaagta gatgatcatg   1260
ataaatgagg taaggtccta ttatcgcaca cttaaaacac agtagatcag aaatttatt    1320 tcgcttcctg tctgtctgca aagaaataca aaatggctag aaaatttaag atctgggcat    1380
gtggagacag agaagactct tgggtttctg ataggcactg actctctctg cctattggtc   1440 tatttttccca tttgcaggtg ccaaaaaaga agagaaaggt agaagacccc gtctctagat   1500
tagataaaag taaagtgatt aacagcgcat tagagctact taatgaggtc ggaatcgaag    1560
gtttaacaac ccgtaaactc gcccagaagc taggtgtaga gcagcctaca ttgtattggc    1620
```

| | |
|---|---|
| atgtaaaaaa taagcgggct ttgctcgacg ccttagccat tgagatgtta gataggcacc | 1680 |
| atactcactt ttgccccttta aaggggaaa gctggcaaga tttttttacgt aataacgcta | 1740 |
| aaagttttag atgtgcttta ctaagtcatc gcgatggagc aaaagtacat ttaggtacac | 1800 |
| ggcctacaga aaaacagtat gaaactctcg aaaatcaatt agcctttta tgccaacaag | 1860 |
| gttttttcact agagaatgca ttatatgcac tcagcgctgt ggggcatttt actttaggtt | 1920 |
| gcgtattgga agatcaagag catcaagtcg ctaaagaaga aagggaaaca cctactactg | 1980 |
| atagtatgcc gccattatta cgacaagcta tcgaattatt tgatcaccaa ggtgcagagc | 2040 |
| cagccttctt attcggcctt gaattgatca tatgcggatt agaaaaacaa cttaaatgtg | 2100 |
| aaagtgggtc ttaggtccgc aaaaatcacc agtctctctc tacaaatcta tctctctcta | 2160 |
| ttttttctcca gaataatgtg tgagtagttc ccagataagg gaattagggt tcttataggg | 2220 |
| tttcgctcat gtgttgagca tataagaaac ccttagtatg tatttgtatt tgtaaaatac | 2280 |
| ttctatcaat aaaatttcta attcctaaaa ccaaaatcca gtgaccggtg atcatgagcg | 2340 |
| gagaattaag | 2350 |

<210> SEQ ID NO 43
<211> LENGTH: 1955
<212> TYPE: DNA
<213> ORGANISM: Artificial Sequence
<220> FEATURE:
<223> OTHER INFORMATION: Synthetic Polynucleotide

<400> SEQUENCE: 43

| | |
|---|---|
| taaaatttct aattcctaaa accaaaatcc agtgaccggt gatcatgagc ggagaattaa | 60 |
| gggagtcacg ttatgacccc cgccgatgac gcgggacaag ccgttttacg tttggaactg | 120 |
| acagaaccgc aacgttgaag gagccactca gccgcgggtt tctggagttt aatgagctaa | 180 |
| gcacatacgt cagaaaccat tattgcgcgt tcaaaagtcg cctaaggtca ctatcagcta | 240 |
| gcaaatattt cttgtcaaaa atgctccact gacgttccat aaattcccct cggtatccaa | 300 |
| ttagagtctc atattcactc tcaatagatc cttcgtcttc actcgagttt accactccct | 360 |
| atcagtgata gagaaaagtg aaagtcgagt ttaccactcc ctatcagtga tagagaaaag | 420 |
| tgaaagtcga gtttaccact ccctatcagt gatagagaaa agtgaaagtc gagtttacca | 480 |
| ctccctatca gtgatagaga aagtgaaag tcgagtttac cactccctat cagtgataga | 540 |
| gaaagtgaa agtcgagttt accactccct atcagtgata gagaaagtg aaagtcgagt | 600 |
| ttaccactcc ctatcagtga tagagaaaag tgaaagtcgg gctcggttcc cgggtcgaga | 660 |
| taagcttatg agaagataaa gatgaagcag cttcatggtt attgctgaat cttcctgtta | 720 |
| agaacaacaa caagaacatt aataacaaca ataacaacca aaataactat gggatgttgt | 780 |
| ttggtgggga agtagtggat gaatacttgg atcttgcgga gtatggaggg gatagtcagt | 840 |
| ttaatgatca gtacagtgtt aatcagcagc aacaaaatta ctctgttcct cagaagaatt | 900 |
| acggaggaga tagcgtggtg ccagttcagg acagacaggg gaaatctatg attctctacc | 960 |
| aacaacaaca acaacaacag cagcagcaca atcaccacct gagttttcag ctaggaatgg | 1020 |
| agtatgacaa ctctaacaca ggatatggtt accctgcttc tatgagtcac agtgtttcga | 1080 |
| tttcgtccat tgatgttagt gttgttccag aatctgcact tagtgaaact tcaaactccc | 1140 |
| accccgcgact tccaaaaggg accattgacc tcttaatata tataagaggt caatggtccc | 1200 |
| ttttggaagt cgcgggtggg agtttgaagt ttcactaagt gcagattctg gaacaacact | 1260 |

| | |
|---|---|
| aacatcaatg gacgaaatcg aaacactgtg actcatagaa gcagggtaac catatcctgt | 1320 |
| gttagagttg tcatactcca ttcctagctg aaaactcagg tggtgattgt gctgctgctg | 1380 |
| ttgttgttgt tgttgttggt agagaatcat agatttcccc tgtctgtcct gaactggcac | 1440 |
| cacgctatct cctccgtaat tcttctgagg aacagagtaa ttttgttgct gctgattaac | 1500 |
| actgtactga tcattaaact gactatcccc tccatactcc gcaagatcca agtattcatc | 1560 |
| cactacttcc ccaccaaaca acatcccata gttattttgg ttgttattgt tgttattaat | 1620 |
| gttcttgttg ttgttcttaa caggaagatt cagcaataac catgaagctg cttcatcttt | 1680 |
| atcttcttcc cgatcgttca aacatttggc aataaagttt cttaagattg aatcctgttg | 1740 |
| ccggtcttgc gatgattatc atataatttc tgttgaatta cgttaagcat gtaataatta | 1800 |
| acatgtaatg catgacgtta tttatgagat gggtttttat gattagagtc ccgcaattat | 1860 |
| acatttaata cgcgatagaa aacaaaatat agcgcgcaaa ctaggataaa ttatcgcgcg | 1920 |
| cggtgtcatc tatgttacta gatcggggcg gccgc | 1955 |

<210> SEQ ID NO 44
<211> LENGTH: 2124
<212> TYPE: DNA
<213> ORGANISM: Artificial Sequence
<220> FEATURE:
<223> OTHER INFORMATION: Synthetic Polynucleotide

<400> SEQUENCE: 44

| | |
|---|---|
| tcgcgcgcgg tgtcatctat gttactagat cggggcggcc gctgaaagcg acgttggatg | 60 |
| ttaacatcta caaattgcct tttcttatcg accatgtacg taagcgctta cgttttttggt | 120 |
| ggacccttga ggaaactggt agctgttgtg ggcctgtggt ctcaagatgg atcattaatt | 180 |
| tccaccttca cctacgatgg ggggcatcgc accggtgagt aatattgtac ggctaagagc | 240 |
| gaatttggcc tgtaagatcc tttttaccga caactcatcc acattgatgg taggcagaaa | 300 |
| gttaaaggat tatcgcaagt caatacttgc ccattcattg atctatttaa aggtgtggcc | 360 |
| tcaaggataa tcgccaaacc attatatttg caatctacca aagatccttc gtcttcactc | 420 |
| gagtttacca ctccctatca gtgatagaga aaagtgaaag tcgagtttac cactccctat | 480 |
| cagtgataga gaaaagtgaa agtcgagttt accactccct atcagtgata gagaaaagtg | 540 |
| aaagtcgagt ttaccactcc ctatcagtga tagagaaaag tgaaagtcga gtttaccact | 600 |
| ccctatcagt gatagagaaa agtgaaagtc gagtttacca ctccctatca gtgatagaga | 660 |
| aaagtgaaag tcgagtttac cactccctat cagtgataga gaaaagtgaa agtcgggctc | 720 |
| ggttcccggg tcgagataag cttatgatgg gaagaaaaaa actagaaatc aagcgaattg | 780 |
| agaacaaaag tagccgacaa gtcaccttct ccaaacgtcg caacggtctc atcgagaaag | 840 |
| ctcgtcagct ttctgttctc tgtgacgcat ccgtcgctct tctcgtcgtc tccgcctccg | 900 |
| gcaagctgta cagcttctcc tccggcgata acctggtcaa gatccttgat cgatatggga | 960 |
| aacagcatgc tgatgatctt aaagccttgg atcatcagtc aaaagctctg aactatggtt | 1020 |
| cacactatga gctacttgaa cttgtggata gcaagcttgt gggatcaaat gtcaaaaatg | 1080 |
| tgagtatcga tgctccttgtt caactggagg aacaccttga gactgccctc tccgtgacta | 1140 |
| gagccaagaa gaccgaactc atgttgaagc ttgttgagaa tcttaaagaa aaggagaaaa | 1200 |
| tgctgaaaga agagaaccag gttttggcta gccagatgga gaataatcat catgtgggag | 1260 |
| cagaagctga gatggagatg tcacctgctg gacaaatctc cgacaatctt ccggtgactc | 1320 |
| tcccactact taattagact agtccctaga gtcctgcttt aatgagatat gcgagacgcc | 1380 |

```
tatgatcgca tgatatttgc tttcaattct gttgtgcacg ttgtaaaaaa cctgagcatg    1440
tgtagctcag atccttaccg ccggtttcgg ttcattctaa tgaatatatc acccgttact    1500
atcgtatttt tatgaataat attctccgtt caatttactg attgtaccct actacttata    1560
tgtacaatat taaaatgaaa acaatatatt gtgctgaata ggtttatagc gacatctatg    1620
atagagcgcc acaataacaa acaattgcgt tttattatta caaatccaat tttaaaaaaa    1680
gcggcagaac cggtcaaacc taaaagactg attacataaa tcttattcaa atttcaaaag    1740
tgccccaggg gctagtatct acgacacacc gagcggcgaa ctaataacgc tcactgaagg    1800
gaactccggt tccccgccgg cgcgcatggg tgagattcct tgaagttgag tattggccgt    1860
ccgctctacc gaaagttacg ggcaccattc aacccggtcc agcacggcgg ccgggtaacc    1920
gacttgctgc cccgagaatt atgcagcatt ttttggtgt atgtgggccc caaatgaagt      1980
gcaggtcaaa ccttgacagt gacgacaaat cgttgggcgg gtccagggcg aattttgcga    2040
caacatgtcg aggctcagca ggatggcaaa cagctattat gggtattatg ggtggttctt    2100
tatgcggaca ctgacggctt tatg                                            2124
```

<210> SEQ ID NO 45
<211> LENGTH: 4176
<212> TYPE: DNA
<213> ORGANISM: Artificial Sequence
<220> FEATURE:
<223> OTHER INFORMATION: Synthetic Polynucleotide

<400> SEQUENCE: 45

```
gacaacatgt cgaggctcag caggagctta gacaaacacc ccttgttata caagaatttt     60
cgctttacaa aatcaaattc gagaaaataa tatatgcact aaataagatc attcggatcc    120
aatctaacca attacgatac gctttgggta cacttgattt ttgtttcagt agttacatat    180
atcttgtttt tatatgctatc tttaaggatc ttcactcaaa gactatttgt tgatgttctt    240 gatgggctc ggaagatttg atatgataca ctctaatctt taggagatac cagccaggat    300
tatattcagt aagacaatca aattttacgt gttcaaactc gttatctttt catttaatgg    360
atgagccaga atctctatag aatgattgca atcgagaata tgttcggccg atatccctttt  420 gttggcttca atattctaca tatcacacaa gaatcgaccg tattgtaccc tctttccata    480
aaggaacaca cagtatgcag atgctttttt cccacatgca gtaacatagg tattcaaaaa    540
tggctaaaag aagttggata acaaattgac aactatttcc atttctgtta tataaatttc    600
acaacacaca aaagcccgta atcaagagtc tgcccatgta cgaaataact tctattattt    660
ggtattgggc ctaagcccag ctcagagtac gtgggggtac cacatatagg aaggtaacaa    720
aatactgcaa gatagcccca taacgtacca gcctctcctt accacgaaga gataagatat    780
aagacccacc ctgccacgtg tcacatcgtc atggtggtta atgataaggg attacatcct    840
tctatgtttg tggacatgat gcatgtaatg tcatgagcca catgatccaa tggccacagg    900
aacgtaagaa tgtagataga tttgatttg tccgttagat agcaaacaac attataaaag      960
gtgtgtatca atacgaacta attcactcat tggattcata gaagtccatt cctcctaagt    1020
atctaaacca tggatgctaa gaactttagt ggcccagttt gtttccgtca tgccgccctc    1080
tcgcctttgg gatatgaaac tgccagatcc ttcgtcttca ctcgagttta ccactccctta   1140 tcagtgatag agaaaagtga aagtcgagtt taccactccc tatcagtgat agagaaaagt    1200
gaaagtcgag tttaccactc cctatcagtg atagagaaaa gtgaaagtcg agtttaccac    1260
```

```
tccctatcag tgatagagaa aagtgaaagt cgagtttacc actccctatc agtgatagag    1320
aaaagtgaaa gtcgagttta ccactcccta tcagtgatag agaaaagtga agtcgagtt     1380 taccactccc tatcagtgat agagaaaagt gaaagtcggg ctcggttccc gggtcgagat    1440
aagcttatga tgaagagaga tcgagatcga gatcgagaaa gagagaaaag agcattctct    1500
aatggtgctg tttcttcagg gaaaagtaag atttgggaag aagatgaaga agaaaaacca    1560
gatgctggaa tggatgttgc tcaaaaactt gaacagcttg agatggctat gggtacaacg    1620
atggaagatg gtattactca tctttctact gataccgttc ataaaaaccc atctgatatg    1680
gctggttggg tacaaagtat gttatcttcg atttcgacaa actttgatat gtgtaatcag    1740
gaaaacgatg tgcttgtatc tggttgtggt tcttcttctt ctataatcga tttctcacaa    1800
aatcatcgaa caagtaccat ttctgatgat gatttaagag ctatacctgg tggtgctgtt    1860
ttcaattcgg atagtaataa aagacacaga tcaacaactt ctagtttttc aactacatcc    1920
tcatctatgg tgacagattc atcagcaacg agacctgttg tactagttga ttcacaagaa    1980
actggggttc gtcttgttca tactttaatg gcgtgtgctg aagctgtaca acaagaaaat    2040
ttaactttag cggatcaact tgttagacat attggtattc ttgcggtttc acaatctggt    2100
gctatgagaa aagttgctac ttactttgct gaagcattag caagaagaat ctacaaaatt    2160
tatccacaag attcaatgga atcatcatat acagatgttt tacaaatgca tttctatgaa    2220 acttgcccctt atctcaaatt cgctcatttt actgctaatc aagccattct tgaagcgttt    2280
acaggttgta acaaagttca tgtaattgat ttcagcttaa acagggtat gcaatggcct     2340 gcacttatgc aagctttagc tttacgcccc ggtggacctc cggcatttag actcaccgga    2400
atcggacctc cacagccgga taacacagat gccttgcaac aagttggatg aagttggct     2460 cagttagcgg aaactattgg ggttgaattt gaattcaggg gatttgttgc taattcgtta    2520
gcagatcttg atgcgactat acttgatata aggccaagtg aaactgaagc agtagctata    2580
aactctgttt tgagcttca tcgattgtta tcccggccgg gagcaattga aaaagtgttg    2640
aactctatta aacagattaa cccgaagatt gttactcttg ttgagcaaga agcgaatcat    2700
aacgcagggg ttttattga tagatttaac gaagctttgc attattactc aaccatgttt     2760
gattcgttag aaagctctgg gtcttcgtct tcagcttcac caactgggat tcttcctcaa    2820
cctccggtga acaatcaaga tttggtgatg tcggaggttt atttagggag acagatttgt    2880
aacgtggtgg cttgtgaagg ttcagatcga gttgaacgac atgaaacact gaatcaatgg    2940
agggttagga tgaactcatc tgggttcgat ccggttcatc tgggttcaaa tgcgttcaaa    3000
caagcttcca tgctttagc tctgttcgcc ggcggcgatg gttacagggt ggaagaaaac     3060
gatgggtgtc ttatgttggg gtggcataca cggccactta tagctacctc cgcctggaag    3120
ctattgccgg actccggcac cggcgccgga gaagtcgagt tgtaacggcc gcataagttt    3180
tactatttac caagcttttt gaatattaac cttcttgtaa cgagtcggtt aaatttgatt    3240
gtttagggtt ttgtattatt ttttttggt cttttaattc atcactttaa ttccctaatt     3300
gtctgttcat ttcgttgttt gtttccggat cgataatgaa atgtaagaga tatcatatat    3360
aaataataaa ttgtcgtttc atatttgcaa tctttttta caaaccttta attaattgta    3420
tgtatgacat tttcttcttg ttatattagg gggaaataat gttaaataaa agtacaaaat    3480
aaactacagt acatccgtact gaataaaatta cctagccaaa aagtacacct ttccatatac    3540
ttcctacatg aaggcatttt caacattttc aaataaggaa tgctacaacc gcataataac    3600
atccacaaat tttttttataa aataacatgt cagacagtga ttgaaagatt ttattatagt    3660
```

| | |
|---|---|
| ttcgttatct tcttttctca ttaagcgaat cactacctaa cacgtcattt tgtgaaatat | 3720 |
| tttttgaatg ttttttatata gttgtagcat tcctctttc aaattagggt ttgtttgaga | 3780 |
| tagcatttca gccggttcat acaacttaaa agcatactct aatgctggaa aaagactaa | 3840 |
| aaaatcttgt aagttagcgc agaatattga cccaaattat atacacacat gaccccatat | 3900 |
| agagactaat tacactttta accactaata attattactg tattataaca tctactaatt | 3960 |
| aaacttgtga gttttgcta gaattattat catatatact aaaaggcagg aacgcaaaca | 4020 |
| ttgccccggt actgtagcaa ctacggtaga cgcattaatt gtctatagtg gacgcattaa | 4080 |
| ttaaccaaaa ccgcctcttt cccttcttc ttgaatggca aacagctatt atgggtatta | 4140 |
| tgggtggttc tttatgcgga cactgacggc tttatg | 4176 |

<210> SEQ ID NO 46
<211> LENGTH: 1457
<212> TYPE: DNA
<213> ORGANISM: Nicotiana tabacum

<400> SEQUENCE: 46

| | |
|---|---|
| tattgactgc aacacggtct acaaggaaga cctctcttta catatacaac aatgcagaga | 60 |
| atttaacaaa atcctctgtg gaaaactact ttagtacatt tctcattatt caatagctag | 120 |
| ttagattgat aatgatgtaa ggtacaatat taatattagg tttagggact tgtagttgat | 180 |
| cttctctttg ctgcattcaa aatgatggca cgattccata actgctatct gcaattaact | 240 |
| gtgtggagaa catctggtct acttcagcct ctacatctgt tcttttcgcg aatcgacctt | 300 |
| tgattcttgg ccgtgtttct gcatacgctt ttcttgaagc atacctatg gttttctcaa | 360 |
| atttacggtt tcttttcttc tctctgtacc taaggactct ggcttccctg tccattggag | 420 |
| taagctgggt aggcatttga atcggagggc ctgagaagag gtcaatggtc ccttttggaa | 480 |
| gtcgcgggtg ggagtttgaa gtttcactaa gtgcagattc tggaacaaca ctaacatcaa | 540 |
| tggacgaaat cgaaacactg tgactcatag aagcagggta accatatcct gtgttagagt | 600 |
| tgtcatactc cattcctagc tgaaaactca ggtggtgatt tgctgctgc tgttgttgtt | 660 |
| gttgttgttg gtagagaaca tagatttccc ctgtctgtcc tgaactggca ccacgctatc | 720 |
| tcctccgtaa ttcttctgag gaacagagta atttttgttgc tgctgattaa cactgtactg | 780 |
| atcattaaac tgactatccc ctccatactc cgcaagatcc aagtattcat ccactacttc | 840 |
| cccaccaaac aacatcccat agttattttg gttgttattg ttgttattaa tgttcttgtt | 900 |
| gttgttctta acaggaagat tcagcaataa ccatgaagct gcttcatctt tatcttcttc | 960 |
| atctattgtc gtatcatctg catcctgagt caaactcaag aacccatcat cctccgtggc | 1020 |
| atccccctcg gggccaccaa tcatcaaagt accaccgcta agggtgtcaa cagctggagg | 1080 |
| accatatagg gtacctggaa tgggcataat tgggacacgg tggtgacggc gtgccaaggg | 1140 |
| gttagcagaa tggatatcag cgtcgcagga ggcacaaagc gaggcagcat ccgccttgca | 1200 |
| aagaaaggct gcaggagcgc gttcacacgc ctcgcaaacc caaacgcgct catgacgtga | 1260 |
| agccacaagg tttgctgcat gtatgcgggc gtcacagccc gcacacaaat atgcagaatc | 1320 |
| ggccctgcag taaacggtgc atgcagtaga ccggcaagtg tcgcacacct ttgcccagtt | 1380 |
| gttgctgctg ttttccttttt tcaacattga actaatttg gcttcttttt tcttcttctt | 1440 |
| gctctctatt ttctgtt | 1457 |

<210> SEQ ID NO 47

<211> LENGTH: 1703
<212> TYPE: DNA
<213> ORGANISM: Homo sapiens

<400> SEQUENCE: 47

```
agtcctggcc tccccgggcg cagcacactc ccagccggcc gcagcctgac acgccgcgcg      60
gccccccagt ctcccgcggc tgctccccca ggcatggcac agggcctcgc ctcactatgg     120
cagcagcacg gcacagcacg ctcgacttca tgctcggcgc caaagctgat ggtgagacca     180
ttctaaaagg cctccagtcc attttccagg agcagggat ggcggagtcg gtgcacacct      240
ggcaggacca tggctattta gcaacctaca caaacaagaa cggcagcttt gccaatttga     300
gaatttaccc acatggattg gtgttgctgg accttcagag ttatgatggt gatgcgcaag     360
gcaaagaaga gatcgacagt attttgaaca agtagagga agaatgaaa gaattgagtc       420
aggacagtac tgggcgggtg aaacgattac cacccatagt gcgaggagga gccatcgaca     480
gatactggcc caccgccgac gggcgcctgg ttgaatatga catagatgaa gtggtatatg     540
acgaagattc accttatcaa aatataaaaa ttctacactc gaagcagttt ggaaatattc     600
tcatccttag tgggatgtt aatttggcag agagtgattt ggcatatacc cggccatca      660
tgggcagtgg caaagaagat tacactggca agatgtact cattctggga ggtggagacg     720
gaggcatatt gtgtgaaata gtcaaactaa accaaagat ggtcactatg gtagagattg      780
accaaatggt gattgatggg tgtaagaaat acatgcgaaa aacgtgtggc gatgtcttag     840
acaatcttaa aggagactgc tatcaggttc taatagaaga ctgtatcccg gtactgaaga     900
ggtacgccaa agaagggaga gaatttgatt atgtgattaa tgatttgaca gctgttccaa     960
tctccacgtc tccagaagaa gattccacat gggagtttct cagactgatt cttgacctct    1020
caatgaaagt gttgaaacag gatgggaaat atttttacaca ggggaactgt gtcaatctga    1080
cagaagcact gtcgctctat gaagaacagc tggggcgcct gtattgtcct gtggaatttt    1140
caaaggagat cgtctgtgtc ccttcatact tggaattgtg ggtattttac actgtttgga    1200
agaaagctaa accctgaaga tcagtagccc ctaatcacat gtgctgcaaa tagccttcct    1260
gacctccata tgctgtacat gacatcaaaa tgagtcaggc aattgattgt gaattcctta    1320
aagttttcct ttttttaata attattttta atttaaaaaa gcaaatggaa aatgtatatt    1380
ttgatgagct tagggtgttt tttttttgaa agtcagctga aggatggtta gacagcacag    1440
cgaagactgc taaatgcact gacccccccc attagaatgt gattttttgtt ccttttttatt    1500
tctctgtggg cttttgtttt tgtttttgtt ttggtagatc ttcaatttgg atatttggag    1560
gagtgaacat cgttgttttg ctggagggaa gatcttgatg gtgttctttt ccccaaaaat    1620
tgacttagat attaaaattt ggtgcttata agagagagtt aaaaaaaaaat aggattgctt    1680
caattaaaat tacaaaagag aca                                          1703
```

<210> SEQ ID NO 48
<211> LENGTH: 243
<212> TYPE: DNA
<213> ORGANISM: Artificial Sequence
<220> FEATURE:
<223> OTHER INFORMATION: Synthetic Polynucleotide

<400> SEQUENCE: 48

```
gaattccctc aatctttact ttcaagaatg gcacaaatta caacatggc acaagggata      60
caaacccctta atcccaattc caatttccat aaaccccaag ttcctaaatc ttcaagtttt     120
cttgttttttg gatctaaaaa actgaaaaat tcagcaaatt ctatgttggt tttgaaaaaa    180
```

```
gattcaattt ttatgcaaaa gttttgttcc tttaggattt cagcatcagt ggctacagca    240
cag                                                                  243

<210> SEQ ID NO 49
<211> LENGTH: 1946
<212> TYPE: DNA
<213> ORGANISM: Artificial Sequence
<220> FEATURE:
<223> OTHER INFORMATION: Synthetic Polynucleotide

<400> SEQUENCE: 49
cacataaaac cccaagttcc taaatcttca agttttcttg ttttggatc taaaaaactg     60 aaaaattcag caaattctat gttggttttg aaaaaagatt caatttttat gcaaagtttt   120
tgttccttta ggatttcagc atcagtggct acagcctgca tgcttcacgg tgcaagcagc   180
cggcccgcaa ccgcccgcaa atcctctggc cttccggaa ccgtccgcat tcccggcgac    240
aagtcgatct cccaccggtc cttcatgttc ggcggtctcg cgagcggtga acgcgcatc    300 accggccttc tggaaggcga ggacgtcatc aatacgggca aggccatgca ggccatgggc   360
gccaggatcc gtaaggaagg cgacacctgg atcatcgatg cgtcggcaa tggcggcctc    420 ctggcgcctg aggcgccgct cgatttcggc aatgccgcca cgggctgccg gctgaccatg   480
ggcctcgtcg gggtctacga tttcgacagc accttcatcg cgacgcctc gctcacaaag    540 cgcccgatgg gccgcgtgtt gaacccgctg cgcgaaatgg gcgtgcaggt gaaatcggaa   600
gacggtgacc gtcttcccgt taccttgcgc gggccgaaga cgccgacgcc gatcacctac   660
cgcgtgccga tggcctccgc acaggtgaag tccgccgtgc tgctcgccgg cctcaacacg   720
cccggcatca cgacggtcat cgagccgatc atgacgcgcg atcatacgga aaagatgctg   780
cagggctttg gcgccaacct taccgtcgag acggatgcgg acggcgtgcg caccatccgc   840
ctggaaggcc gcggcaagct caccggccaa gtcatcgacg tgcccggcga cccgtcctcg   900
acggccttcc gctggttgc ggccctgctt gttccgggct ccgacgtcac catcctcaac    960
gtgctgatga cccccaccccg caccggcctc atcctgacgc tgcaggaaat gggcgccgac  1020
atcgaagtca tcaacccgcg ccttgccggc ggcgaagacg tggcggacct cgcgttcgc   1080 tcctccacgc tgaagggcgt cacggtgccg aagaccgcg cgccttcgat gatcgacgaa   1140
tatccgattc tcgctgtcgc cgccgccttc gcggaagggg cgaccgtgat gaacggtctg   1200
gaagaactcc gcgtcaagga aagcgaccgc ctctcggccg tcgccaatgg cctcaagctc   1260
aatggcgtgg attgcgatga gggcgagacg tcgctcgtcg tgcgtggccg ccctgacggc   1320
aaggggctcg gcaacgcctc gggcgccgcc gtcgccaccc atctcgatca ccgcatcgcc   1380
atgagcttcc tcgtcatggg cctcgtgtcg gaaaaccctg tcacggtgga cgatgccacg   1440
atgatcgcca cgagcttccc ggagttcatg gacctgatgg ccgggctggg cgcgaagatc   1500
gaactctccg atacgaaggc tgcctgatga gctcgaattc gagctcggta ccggatccaa   1560
ttcccgatcg ttcaaacatt tggcaataaa gtttcttaag attgaatcct gttgccggtc   1620
ttgcgatgat tatcatataa tttctgttga attacgttaa gcatgtaata attaacatgt   1680
aatgcatgac gttatttatg agatgggttt ttatgattag agtcccgcaa ttatacattt   1740
aatacgcgat agaaaacaaa atatagcgcg caaactagga taaattatcg cgcgcggtgt   1800
catctatgtt actagatcgg ggatcgatcc cccaccggtc cttcatgttc ggcggtctcg   1860
cgagcggtga acgcgcatc accggccttc tggaaggcga ggacgtcatc aatacgggca   1920
```

```
aggccatgca ggccatgggc gccagg                                          1946
```

<210> SEQ ID NO 50
<211> LENGTH: 707
<212> TYPE: DNA
<213> ORGANISM: Artificial Sequence
<220> FEATURE:
<223> OTHER INFORMATION: Synthetic Polynucleotide

<400> SEQUENCE: 50

```
gctcctacaa atgccatcat tgcgataaag gaaaggccat cgttgaagat gcctctgccg    60
acagtggtcc caaagatgga cccccaccca cgaggagcac cgtggaaaaa gaagacgttc   120
caaccacgtc ttcaaagcaa gtggattgat gtgatatctc cactgacgta agggatgacg   180
cacaatccca ctatccttcg caagacccct cctctatata aggaagttca tttcatttgg   240
agaggacacg ctgacaagct gactctagca gatctttcaa gaatggcaca aattaacaac   300
atggcacaag ggatacaaac ccttaatccc aattccaatt tccataaacc ccaagttcct   360
aaatcttcaa gttttcttgt ttttggatct aaaaaactga aaaattcagc aaattctatg   420
ttggttttga aaaagattc aatttttatg caaaagtttt gttcctttag gatttcagca   480
tcagtggcta cagcctgcat gcttcacggt gcaagcagcc ggcccgcaac cgcccgcaaa   540
tcctctggcc tttccggaac cgtccgcatt cccggcgaca gtcgatctc ccaccggtcc    600
ttcatgttcg gcggtctcgc gagcggtgaa acgcgcatca ccggccttct ggaaggcgag   660
gacgtcatca atacgggcaa ggccatgcag gccatgggcg ccaggat                 707
```

<210> SEQ ID NO 51
<211> LENGTH: 145
<212> TYPE: DNA
<213> ORGANISM: Artificial Sequence
<220> FEATURE:
<223> OTHER INFORMATION: Synthetic Polynucleotide

<400> SEQUENCE: 51

```
gacggcccctt ctcctcaggt tacagtctca agcttcgcca tgtacatggc ccttcagtgt   60
acatggatgg gcgggttggt aactaaaaga cccctttactc aataaagtag atgatcatga  120
taaatgaggg acggcccttc tcctc                                         145
```

<210> SEQ ID NO 52
<211> LENGTH: 1503
<212> TYPE: DNA
<213> ORGANISM: Artificial Sequence
<220> FEATURE:
<223> OTHER INFORMATION: Synthetic Polynucleotide

<400> SEQUENCE: 52

```
atggcttcta tttcttcttc tgtggctact gtttctagga ctgctccagc tcaagctaat    60
atggtggctc cattcacagg cttgaaatcc aatgctgctt cccaactac taagaaggct   120
aacgatttct ctactctccc atctaatggt ggaagggttc agtgtatgca agtttggcca   180
gcttacggaa ataagaagtt cgagactctt tcttaccttc caccactttc tatggctcca   240
actgtgatga tggcttcttc tgctactgct gttgctccat tccaaggatt gaagtctact   300
gcttctttgc cagttgctag aaggtcatct cgttctcttg gaaacgtttc taacggtgga   360
aggattagat gtgctatggc tcatcatcat caccatcact acggaaagaa ccttatttct   420
gagcttagag agaaagagat cttcaagagg cttcatcacg ttgagttcta cgtttcttcc   480
gctaagactt ggtcctactt catgaatagg ggactcggat tcaagactgt tgcttatgct   540
```

-continued

```
ggaccagaaa ctggaatcag ggataagatc tcctacgtta tgtctcaagg tactgctagg      600
atttctttca cttcctccat gaacgatgat tcctacattt ccaaccacgt taagaaacac      660
ggtgatggtg ttaaggatat cgctctcgaa gtggatgatc ttgatgaggc taagtctctc      720
attgagaagt acgaaactaa ggtgtccaag atcaacgaga tcaaggatgg aaacggaaag      780
attaggactg ctgagatcaa gacttacggt gaaactgtgc acactcttat cgagactggt      840
gattacaacg tgttttcat gccaggatac gaagagtctg agatcaactc caagaacact       900
ggtatcaaaa aaatcgatca cattgtggga aatgtttacg agggtgaaat ggattcttgg      960
gtgaacttct acattgagaa gttgggattc gagcacctta tcactttcga tgataaggat     1020
atcaggactg attactctgc tcttaggtct aaggtggtga agtacaacga tgatatcgtg     1080
ttccctatta acgaaccagc taagggactt aggaagtccc aaatcgaaga gtacctcgat     1140
tattaccgtt ctgagggtgt tcaacacatt gctttgctca cagacgatat catcaagact     1200
gtgtccatga tggaagagaa cggaattgag ttccttaaga ctccaggatc ttactacgag     1260
tctttgtcct ctaggattgg atctatcgat gaggatctca acgaaatcga aagcacaac      1320 attcttgtgg atagggatga gaacggatac cttctccaga ttttcactaa gccagtgact     1380
gataggccaa cattcttctt cgaagtgatc caaagaaagg gtgctagatc tttcggaaac     1440
ggaaacttca aggctctttt cgaggctatt gagagagaac aagctaagag gggaaacctt     1500
tga                                                                    1503
```

<210> SEQ ID NO 53  
<211> LENGTH: 1944  
<212> TYPE: DNA  
<213> ORGANISM: Petunia x hybrida

<400> SEQUENCE: 53

```
gaattccctc aatctttact ttcaagaatg gcacaaatta caacatggc tcaagggata        60 caaaccctta atcccaattc caatttccat aaaccccaag ttcctaaatc ttcaagtttt      120 cttgttttg gatctaaaaa actgaaaaat tcagcaaatt ctatgttggt tttgaaaaaa       180
gattcaattt ttatgcaaaa gttttgttcc tttaggattt cagcatcagt ggctacagca      240
cagaagcctt ctgagatagt gttgcaaccc attaaagaga tttcaggcac tgttaaattg      300
cctggctcta atcattatc taatagaatt ctccttcttg ctgccttatc tgaaggaaca       360
actgtggttg acaatttact aagtagtgat gatattcatt acatgcttgg tgccttgaaa      420
acacttggac tgcatgtaga agaagatagt gcaaccaac gagctgttgt tgaaggttgt       480
ggtgggcttt tccctgttgg taaagagtcc aaggaagaaa ttcaactgtt ccttggaaat      540
gcaggaacag caatgcggcc actaacagca gcagttactg tagctggtgg aaattcaagg      600
tatgtacttg atggagttcc tcgaatgaga gagagaccaa ttagtgattt ggttgatggt      660
cttaaacagc ttggtgcaga ggttgattgt tccttggta cgaaatgtcc tcctgttcga       720
attgtcagca agggaggtct tcctggaggg aaggtcaagc tctctggatc cattagcagc      780
caatacttga ctgctctgct tatggctgct ccactggctt taggagatgt ggagattgaa      840
atcattgaca aactaattag tgtaccttat gtcgagatga cattgaagtt gatggagcga      900
tttggtattt ctgtggagca cagtagtagc tgggacaggt tctttgtccg aggaggtcag      960
aaatacaagt ctcctggaaa agcttttgtc gaaggtgatg cttcaagtgc tagctacttc     1020
ttggctggtg cagcagtcac aggtggaact atcactgttg aaggttgtgg acaaacagt      1080
```

| | |
|---|---|
| ttacagggggg atgtcaaatt tgctgaggta cttgaaaaaa tgggagctga agttacgtgg | 1140 |
| acagagaaca gtgtcacagt caaaggacct ccaaggagtt cttctgggag gaagcatttg | 1200 |
| cgtgccattg atgtgaacat gaataaaatg cctgatgttg ccatgacact tgctgttgtt | 1260 |
| gcactttatg ctgatggtcc cacagctata agagatgttg ctagctggag agtcaaggaa | 1320 |
| actgagcgca tgatcgccat atgcacagaa cttaggaagt taggagcaac cgttgaagaa | 1380 |
| ggaccagact actgcataat caccccaccg gagaaactaa atgtgaccga tattgataca | 1440 |
| tacgatgatc acaggatggc catggctttt tctcttgctg cttgtgcaga tgttcccgtc | 1500 |
| accatcaatg ccctggctg cacgcggaaa accttcccta actactttga tgtacttcag | 1560 |
| cagtactcca agcattgaac cgcttcccta tattgcagaa tgtaagtaag aatatgtgaa | 1620 |
| gagtttagtt cttgtacaag acaggctacg actgcctggt atcagaacca caatgggttc | 1680 |
| catttcagtt cagaagggca ttccaaggct tcgaactctt tacttatttg cgagtgatga | 1740 |
| aatgtatttg ttagagttga gcttcttttt gtctttaagg aatgtacact aatagagtta | 1800 |
| agaattacta gtatgggcca gtgtaaggag tactattact ctttgcttat tttattgatt | 1860 |
| gagttttgtc aaggatctgg ctttgtcaag aattactggt taatttatt gacaatctca | 1920 |
| tgtgtctaaa tgaaattgtt tgat | 1944 |

<210> SEQ ID NO 54
<211> LENGTH: 2896
<212> TYPE: DNA
<213> ORGANISM: Artificial Sequence
<220> FEATURE:
<223> OTHER INFORMATION: Synthetic Polynucleotide

<400> SEQUENCE: 54

| | |
|---|---|
| taactataac ggtcctaagg tagcgatggc aaacagctat tatgggtatt atgggtcaac | 60 |
| atgtggagca cgacacactt gtctactcca aaaatatcaa agatacagtc tcagaagacc | 120 |
| aaagggcaat tgagactttt caacaaaggg taatatccgg aaacctcctc ggattccatt | 180 |
| gcccagctat ctgtcacttt attgtgaaga gagtggaaaa ggaaggtggc tcctacaaat | 240 |
| gccatcattg cgataaagga aaggccatcg ttgaagatgc ctctgccgac agtggtccca | 300 |
| aagatggacc cccaccacg aggagcatcg tggaaaaaga agacgttcca accacgtctt | 360 |
| caaagcaagt ggattgatgt gataacatgg tggagcacga cacttgtc tactccaaaa | 420 |
| atatcaaaga tacagtctca gaagaccaaa gggcaattga acttttcaa caaagggtaa | 480 |
| tatccggaaa cctcctcgga ttccattgcc cagctatctg tcactttatt gtgaagatag | 540 |
| tggaaaagga aggtggctcc tacaaatgcc atcattgcga taaaggaaag gccatcgttg | 600 |
| aagatgcctc tgccgacagt ggtcccaaag atggaccccc acccacgagg agcatcgtgg | 660 |
| aaaaagaaga cgttccaacc acgtcttcaa agcaagtgga ttgatgtgat atctccactg | 720 |
| acgtaaggga tgacgcacaa tcccactatc cttcgcaaga cccttcctct atataaggaa | 780 |
| gttcatttca tttggagagg acgtcgagag ttctcaacac aacatataca aaacaaacga | 840 |
| atctcaagca atcaagcatt ctacttctat tgcagcaatt taaatcattt cttttaaagc | 900 |
| aaaagcaatt ttctgaaaat tttcaccatt tacgaacgat agtgaatttt atggtaagtt | 960 |
| cctgggcggt tggtatcaag gttacaagac aggtttaagg agaccaatag aaactgggca | 1020 |
| tgtggagaca gagaagactc ttgggtttct gatgggccc gtttcataaa atggttttg | 1080 |
| tttgacccta acctaacttt ttttttttt gtaattgtgt taaatcacat tttttcttt | 1140 |
| aatttgtccc aatcttcagg ttacagtctc tagcttcgcc atgtacatgg cccttctgtg | 1200 |

-continued

```
tacatggatg ggcggggagg taactaaaag acccttttaca caataaagta gatgatcatg    1260
ataaatgagg taaggtccta ttatcgcaca cttaaaacac agtagatcag aaatttattt    1320
tcgcttcctg tctgtctgca aagaaataca aaatggctag aaaatttaag atctgggcat    1380
gtggagacag agaagactct tgggtttctg ataggcactg actctctctg cctattggtc    1440
tattttccca tttgcagaag ctcctgtcct ccatcgagca ggcctgcgac atctgccgcc    1500
tcaagaagct caagtgctcc aaggagaagc cgaagtgcgc caagtgtctg aagaacaact    1560
gggagtgtcg ctactctccc aaaaccaagc gctccccgct gacccgcgcc cacctcaccg    1620
aagtggagtc ccgcctggag cgcctggagc agctcttcct cctgatcttc cctcgagagg    1680
acctcgacat gatcctgaaa atggactccc tccaggacat caaagccctg ctcaccggcc    1740
tcttcgtcca ggacaacgtg aacaaagacg ccgtcaccga ccgcctggcc tccgtggaga    1800
ccgacatgcc cctcaccctg cgccagcacc gcatcagcgc gacctcctcc tcggaggaga    1860
gcagcaacaa gggccagcgc cagttgaccg tctcgacggc cccccccgacc gacgtcagcc    1920 tgggggacga gctccactta gacggcgagg acgtggcgat ggcgcatgcc gacgcgctag    1980
acgatttcga tctggacatg ttgggggacg gggattcccc ggggccggga tttacccccc    2040
acgactccgc ccctacggc gctctggata tggccgactt cgagtttgag cagatgttta    2100
ccgatgccct tggaattgac gagtacggtg ggtaggtccg caaaaatcac cagtctctct    2160
ctacaaatct atctctctct attttctcc agaataatgt gtgagtagtt cccagataag    2220
ggaattaggg ttcttatagg gtttcgctca tgtgttgagc atataagaaa cccttagtat    2280
gtatttgtat ttgtaaaata cttctatcaa taaaatttct aattcctaaa accaaaatcc    2340
agtgacggac tgtagaggtt ccgggtgaca gccctccgac gggtgacagc cctccgacgg    2400
gtgacagccc tccgaattct agaggatccg ggtgacagcc ctccgacggg tgacagccct    2460
ccgacgggtg acagccctcc gaattcgagc tcggtacccg gggatctgtc gacctcgatc    2520
gagatcttcg caagacccctt cctctatata aggaagttca tttcatttgg agaggacacg    2580
ctgaaatggt gccaaaaaag aagagaaagg tagaagaccc cgtcgtccgc aaaaatcacc    2640
agtctctctc tacaaatcta tctctctcta tttttctcca gaataatgtg tgagtagttc    2700
ccagataagg gaattagggt tcttataggg tttcgctcat gtgttgagca tataagaaac    2760
ccttagtatg tatttgtatt tgtaaaatac ttctatcaat aaaatttcta attcctaaaa    2820
ccaaaatcca gtgactggca aacagctatt atgggtatta tgggtggttc tttatgcgga    2880
cactgacggc tttatg                                                     2896
```

<210> SEQ ID NO 55
<211> LENGTH: 4399
<212> TYPE: DNA
<213> ORGANISM: Artificial Sequence
<220> FEATURE:
<223> OTHER INFORMATION: Synthetic Polynucleotide

<400> SEQUENCE: 55

```
taactataac ggtcctaagg tagcgatggc aaacagctat tatgggtatt atgggtcaac      60
atgtggagca cgacacactt gtctactcca aaaatatcaa agatacagtc tcagaagacc     120
aaagggcaat tgagactttt caacaaaggg taatatccgg aaacctcctc ggattccatt     180
gcccagctat ctgtcacttt attgtgaaga tagtggaaaa ggaaggtggc tcctacaaat     240
gccatcattg cgataaagga aaggccatcg ttgaagatgc ctctgccgac agtggtccca     300
```

```
aagatggacc cccacccacg aggagcatcg tggaaaaaga agacgttcca accacgtctt    360
caaagcaagt ggattgatgt gataacatgg tggagcacga cacacttgtc tactccaaaa    420
atatcaaaga tacagtctca gaagaccaaa gggcaattga gacttttcaa caaagggtaa    480
tatccggaaa cctcctcgga ttccattgcc cagctatctg tcactttatt gtgaagatag    540
tggaaaagga aggtggctcc tacaaatgcc atcattgcga taaaggaaag gccatcgttg    600
aagatgcctc tgccgacagt ggtcccaaag atggaccccc acccacgagg agcatcgtgg    660
aaaaagaaga cgttccaacc acgtcttcaa agcaagtgga ttgatgtgat atctccactg    720
acgtaaggga tgacgcacaa tcccactatc cttcgcaaga cccttcctct atataaggaa    780
gttcatttca tttggagagg acgtcgagag ttctcaacac aacatataca aaacaaacga    840
atctcaagca atcaagcatt ctacttctat tgcagcaatt taaatcattt cttttaaagc    900
aaaagcaatt ttctgaaaat tttcaccatt tacgaacgat agtgaatttt atggtaagtt    960
cctgggcggt tggtatcaag gttacaagac aggtttaagg agaccaatag aaactgggca   1020
tgtggagaca gagaagactc ttgggtttct gatgggccc gtttcataaa atggttttg    1080 tttgacccta acctaacttt tttttttttt gtaattgtgt taaatcacat ttttttcttt   1140
aatttgtccc aatcttcagg ttacagtctc tagcttcgcc atgtacatgg cccttctgtg   1200
tacatggatg ggcggggagg taactaaaag acccttaca caataaagta gatgatcatg    1260
ataaatgagg taaggtccta ttatcgcaca cttaaaacac agtagatcag aaatttattt   1320
tcgcttcctg tctgtctgca aagaaataca aaatggctag aaaatttaag atctgggcat   1380
gtggagacag agaagactct tgggtttctg ataggcactg actctctctg cctattggtc   1440
tattttccca tttgcagaag ctcctgtcct ccatcgagca ggcctgcgac atctgccgcc   1500
tcaagaagct caagtgctcc aaggagaagc cgaagtgcgc caagtgtctg aagaacaact   1560
gggagtgtcg ctactctccc aaaaccaagc gctccccgct gacccgcgcc cacctcaccg   1620
aagtggagtc ccgcctggag cgcctggagc agctcttcct cctgatcttc cctcgagagg   1680
acctcgacat gatcctgaaa atggactccc tccaggacat caaagccctg ctcaccggcc   1740
tcttcgtcca ggacaacgtg aacaaagacg ccgtcaccga ccgcctggcc tccgtggaga   1800
ccgacatgcc cctcacccctg cgccagcacc gcatcagcgc gacctcctcc tcggaggaga   1860
gcagcaacaa gggccagcgc cagttgaccg tctcgacggc cccccgacc gacgtcagcc    1920 tgggggacga gctccactta gacggcgagg acgtggcgat ggcgcatgcc gacgcgctag   1980
acgatttcga tctggacatg ttgggggacg gggattcccc ggggccggga tttaccccc    2040 acgactccgc cccctacggc gctctggata tggccgactt cgagtttgag cagatgttta   2100
ccgatgccct tggaattgac gagtacggtg ggtaggtccg caaaaatcac cagtctctct   2160
ctacaaatct atctctctct attttctcc agaataatgt gtgagtagtt cccagataag    2220
ggaattaggg ttcttatagg gtttcgctca tgtgttgagc atataagaaa cccttagtat   2280
gtatttgtat ttgtaaaata cttctatcaa taaaatttct aattcctaaa accaaaatcc    2340
agtgacggac tgtagaggtt ccgggtgaca gccctccgac gggtgacagc cctccgacgg   2400
gtgacagccc tccgaattct agaggatccg ggtgacagcc ctccgacggg tgacagccct   2460
ccgacgggtg acagccctcc gaattcgagc tcggtacccg gggatctgtc gacctcgatc   2520
gagatcttcg caagcccctt cctctatata aggaagttca tttcatttgg agaggacacg   2580
ctgaaatggt gccaaaaaag aagagaaagg tagaagaccc cgtcatggct tctatttctt   2640
cttctgtggc tactgtttct aggactgctc cagctcaagc taatatggtg gctccattca   2700
```

```
caggcttgaa atccaatgct gctttcccaa ctactaagaa ggctaacgat ttctctactc    2760
tcccatctaa tggtggaagg gttcagtgta tgcaagtttg gccagcttac ggaaataaga    2820
agttcgagac tctttcttac cttccaccac tttctatggc tccaactgtg atgatggctt    2880
cttctgctac tgctgttgct ccattccaag gattgaagtc tactgcttct ttgccagttg    2940
ctagaaggtc atctcgttct cttggaaacg tttctaacgg tggaaggatt agatgtgcta    3000
tggctcatca tcatcaccat cactacgaaa agaaccttat ttctgagctt agagagaaag    3060
agatcttcaa gaggcttcat cacgttgagt tctacgtttc ttccgctaag acttggtcct    3120
acttcatgaa tagggactc ggattcaaga ctgttgctta tgctggacca gaaactggaa    3180
tcagggataa gatctcctac gttatgtctc aaggtactgc taggatttct ttcacttcct    3240
ccatgaacga tgattcctac atttccaacc acgttaagaa acacggtgat ggtgttaagg    3300
atatcgctct cgaagtggat gatcttgatg aggctaagtc tctcattgag aagtacggaa    3360
ctaaggtgtc caagatcaac gagatcaagg atggaaacgg aaagattagg actgctgaga    3420
tcaagactta cggtgaaact gtgcacactc ttatcgagac tggtgattac aacggtgttt    3480
tcatgccagg atacgaagag tctgagatca actccaagaa cactggtatc aaaaaaatcg    3540
atcacattgt gggaaatgtt tacgagggtg aaatggattc ttgggtgaac ttctacattg    3600
agaagttggg attcgagcac cttatcactt tcgatgataa ggatatcagg actgattact    3660
ctgctcttag gtctaaggtg gtgaagtaca acgatgatat cgtgttccct attaacgaac    3720
cagctaaggg acttaggaag tcccaaatcg aagagtacct cgattattac cgttctgagg    3780
gtgttcaaca cattgctttg ctcacagacg atatcatcaa gactgtgtcc atgatggaag    3840
agaacggaat tgagttcctt aagactccag gatcttacta cgagtctttg tcctctagga    3900
ttggatctat cgatgaggat ctcaacgaaa tcgaagagca acacattctt gtggataggg    3960
atgagaacgg ataccttctc cagattttca ctaagccagt gactgatagg ccaacattct    4020
tcttcgaagt gatccaaaga aagggtgcta gatctttcgg aaacggaaac ttcaaggctc    4080 tttttcgaggc tattgagaga gaacaagcta agagggaaa cctttgagtc cgcaaaaatc    4140
accagtctct ctctacaaat ctatctctct ctatttttct ccagaataat gtgtgagtag    4200
ttcccagata agggaattag ggttcttata gggtttcgct catgtgttga gcatataaga    4260 aaccccttagt atgtatttgt atttgtaaaa tacttctatc aataaaattt ctaattccta    4320
aaaccaaaat ccagtgactg gcaaacagct attatgggta ttatgggtgg ttctttatgc    4380
ggacactgac ggctttatg                                                 4399
```

<210> SEQ ID NO 56
<211> LENGTH: 4842
<212> TYPE: DNA
<213> ORGANISM: Artificial Sequence
<220> FEATURE:
<223> OTHER INFORMATION: Synthetic Polynucleotide

<400> SEQUENCE: 56

```
taactataac ggtcctaagg tagcgatggc aaacagctat tatgggtatt atgggtcaac      60
atgtggagca cgacacactt gtctactcca aaaatatcaa agatacagtc tcagaagacc     120
aaagggcaat tgagactttt caacaaaggg taatatccgg aaacctcctc ggattccatt     180
gcccagctat ctgtcacttt attgtgaaga tagtggaaaa ggaaggtggc tcctacaaat     240
gccatcattg cgataaagga aaggccatcg ttgaagatgc ctctgccgac agtggtccca     300
```

```
aagatggacc cccacccacg aggagcatcg tggaaaaaga agacgttcca accacgtctt    360
caaagcaagt ggattgatgt gataacatgg tggagcacga cacacttgtc tactccaaaa    420
atatcaaaga tacagtctca gaagaccaaa gggcaattga gacttttcaa caaagggtaa    480
tatccggaaa cctcctcgga ttccattgcc cagctatctg tcactttatt gtgaagatag    540
tggaaaagga aggtggctcc tacaaatgcc atcattgcga taaaggaaag gccatcgttg    600
aagatgcctc tgccgacagt ggtcccaaag atggaccccc acccacgagg agcatcgtgg    660
aaaaagaaga cgttccaacc acgtcttcaa agcaagtgga ttgatgtgat atctccactg    720
acgtaaggga tgacgcacaa tcccactatc cttcgcaaga cccttcctct atataaggaa    780
gttcatttca tttggagagg acgtcgagag ttctcaacac aacatataca aaacaaacga    840
atctcaagca atcaagcatt ctacttctat tgcagcaatt taaatcattt cttttaaagc    900
aaaagcaatt ttctgaaaat tttcaccatt tacgaacgat agtgaatttt atggtaagtt    960
cctgggcggt tggtatcaag gttacaagac aggtttaagg agaccaatag aaactgggca   1020
tgtggagaca gagaagactc ttgggtttct gatggggccc gtttcataaa atggtttttg   1080
tttgacccta acctaacttt tttttttttt gtaattgtgt taaatcacat ttttttcttt   1140
aatttgtccc aatcttcagg ttacagtctc tagcttcgcc atgtacatgg cccttctgtg   1200
tacatggatg ggcggggagg taactaaaag acccttaca caataaagta gatgatcatg   1260
ataaatgagg taaggtccta ttatcgcaca cttaaaacac agtagatcag aaatttattt   1320
tcgcttcctg tctgtctgca aagaaataca aaatggctag aaaatttaag atctgggcat   1380
gtggagacag agaagactct tgggtttctg ataggcactg actctctctg cctattggtc   1440
tattttccca tttgcagaag ctcctgtcct ccatcgagca ggcctgcgac atctgccgcc   1500
tcaagaagct caagtgctcc aaggagaagc cgaagtgcgc caagtgtctg aagaacaact   1560
gggagtgtcg ctactctccc aaaaccaagc gctccccgct gacccgcgcc cacctcaccg   1620
aagtggagtc ccgcctggag cgcctggagc agctcttcct cctgatcttc cctcgagagg   1680
acctcgacat gatcctgaaa atggactccc tccaggacat caaagccctg ctcaccggcc   1740
tcttcgtcca ggacaacgtg aacaaagacg ccgtcaccga ccgcctggcc tccgtggaga   1800
ccgacatgcc cctcaccctg cgccagcacc gcatcagcgc gacctcctcc tcggaggaga   1860
gcagcaacaa gggccagcgc cagttgaccg tctcgacggc cccccgacc gacgtcagcc   1920 tgggggacga gctccactta gacggcgagg acgtggcgat ggcgcatgcc gacgcgctag   1980
acgatttcga tctggacatg ttggggggacg gggattcccc ggggccggga tttaccccc   2040 acgactccgc cccctacggc gctctggata tggccgactt cgagtttgag cagatgttta   2100
ccgatgccct tggaattgac gagtacggtg ggtaggtccg caaaaatcac cagtctctct   2160
ctacaaatct atctctctct attttctcc agaataatgt gtgagtagtt cccagataag   2220
ggaattaggg ttcttatagg gtttcgctca tgtgttgagc atataagaaa cccttagtat   2280
gtatttgtat ttgtaaaata cttctatcaa taaaatttct aattcctaaa accaaaatcc   2340
agtgacggac tgtagaggtt ccgggtgaca gccctccgac gggtgacagc cctccgacgg   2400
gtgacagccc tccgaattct agaggatccg ggtgacagcc ctccgacggg tgacagccct   2460 ccgacggtg acagccctcc gaattcgagc tcggtacccg gggatctgtc gacctcgatc   2520
gagatcttcg caagcccctt cctctatata aggaagttca tttcatttgg agaggacacg   2580
ctgaaatggt gccaaaaaag aagagaaagg tagaagaccc cgtccacata aaaccccaag   2640
ttcctaaatc ttcaagtttt cttgtttttg gatctaaaaa actgaaaaat tcagcaaatt   2700
```

```
ctatgttggt tttgaaaaaa gattcaattt ttatgcaaaa gttttgttcc tttaggattt   2760
cagcatcagt ggctacagcc tgcatgcttc acgtgcaag cagccggccc gcaaccgccc    2820
gcaaatcctc tggcctttcc ggaaccgtcc gcattcccgg cgacaagtcg atctcccacc   2880
ggtccttcat gttcggcggt ctcgcgagcg gtgaaacgcg catcaccggc cttctggaag   2940
gcgaggacgt catcaatacg ggcaaggcca tgcaggccat gggcgccagg atccgtaagg   3000
aaggcgacac ctggatcatc gatggcgtcg gcaatggcgg cctcctggcg cctgaggcgc   3060
cgctcgattt cggcaatgcc gccacgggct gccggctgac catgggcctc gtcggggtct   3120
acgatttcga cagcaccttc atcggcgacg cctcgctcac aaagcgcccg atgggccgcg   3180
tgttgaaccc gctgcgcgaa atgggcgtgc aggtgaaatc ggaagacggt gaccgtcttc   3240
ccgttacctt gcgcgggccg aagacgccga cgccgatcac ctaccgcgtg ccgatggcct   3300
ccgcacaggt gaagtccgcc gtgctgctcg ccggcctcaa cacgcccggc atcacgacgg   3360
tcatcgagcc gatcatgacg cgcgatcata cggaaaagat gctgcagggc tttggcgcca   3420
accttaccgt cgagacggat gcggacggcg tgcgcaccat ccgcctggaa ggccgcggca   3480
agctcaccgg ccaagtcatc gacgtgccgg gcgacccgtc ctcgacggcc ttcccgctgg   3540
ttgcggccct gcttgttccg ggctccgacg tcaccatcct caacgtgctg atgaacccca   3600
cccgcaccgg cctcatcctg acgctgcagg aaatgggcgc cgacatcgaa gtcatcaacc   3660
cgcgccttgc cggcggcgaa gacgtggcgg acctgcgcgt tcgctcctcc acgctgaagg   3720
gcgtcacggt gccggaagac cgcgcgcctt cgatgatcga cgaatatccg attctcgctg   3780
tcgccgccgc cttcgcggaa ggggcgaccg tgatgaacgg tctggaagaa ctccgcgtca   3840
aggaaagcga ccgcctctcg gccgtcgcca atggcctcaa gctcaatggc gtggattgcg   3900
atgagggcga gacgtcgctc gtcgtgcgtg gccgccctga cggcaagggg ctcggcaacg   3960
cctcgggcgc cgccgtcgcc acccatctcg atcaccgcat cgccatgagc ttcctcgtca   4020
tgggcctcgt gtcggaaaac cctgtcacgg tggacgatgc cacgatgatc gccacgagct   4080
tcccggagtt catggacctg atggccgggc tgggcgcgaa gatcgaactc tccgatacga   4140
aggctgcctg atgagctcga attcgagctc ggtaccggat ccaattcccg atcgttcaaa   4200
catttggcaa taaagtttct taagattgaa tcctgttgcc ggtcttgcga tgattatcat   4260
ataatttctg ttgaattacg ttaagcatgt aataattaac atgtaatgca tgacgttatt   4320
tatgagatgg gttttatga ttagagtccc gcaattatac atttaatacg cgatagaaaa   4380
caaaatatag cgcgcaaact aggataaatt atcgcgcgcg gtgtcatcta tgttactaga   4440
tcggggatcg atcccccacc ggtccttcat gttcggcggt ctcgcgagcg gtgaaacgcg   4500
catcaccggc cttctggaag gcgaggacgt catcaatacg ggcaaggcca tgcaggccat   4560
gggcgccagg gtccgcaaaa atcaccagtc tctctctaca aatctatctc tctctatttt   4620
tctccagaat aatgtgtgag tagttcccag ataagggaat tagggttctt atagggtttc   4680
gctcatgtgt tgagcatata agaaaccctt agtatgtatt tgtatttgta aaatacttct   4740
atcaataaaa tttctaattc ctaaaaccaa aatccagtga ctggcaaaca gctattatgg   4800
gtattatggg tggttctttta tgcggacact gacggcttta tg                    4842
```

<210> SEQ ID NO 57
<211> LENGTH: 8623
<212> TYPE: DNA
<213> ORGANISM: Artificial Sequence
<220> FEATURE:

<223> OTHER INFORMATION: Synthetic Polynucleotide

<400> SEQUENCE: 57

| | |
|---|---|
| gagggcctat ttcccatgat tccttcatat ttgcatatac gatacaaggc tgttagagag | 60 |
| ataattggaa ttaatttgac tgtaaacaca aagatattag tacaaaatac gtgacgtaga | 120 |
| aagtaataat ttcttgggta gtttgcagtt ttaaaattat gttttaaaat ggactatcat | 180 |
| atgcttaccg taacttgaaa gtatttcgat ttcttggctt tatatatctt gtggaaagga | 240 |
| cgaaacaccg ggtcttcgag aagacctgtt ttagagctag aaatagcaag ttaaaataag | 300 |
| gctagtccgt tatcaacttg aaaaagtggc accgagtcgg tgcttttttg tttagagct | 360 |
| agaaatagca agttaaaata aggctagtcc gttttagcg cgtgcgccaa ttctgcagac | 420 |
| aaatggctct agaggtaccc gttacataac ttacggtaaa tggcccgcct ggctgaccgc | 480 |
| ccaacgaccc ccgcccattg acgtcaatag taacgccaat agggactttc cattgacgtc | 540 |
| aatgggtgga gtatttacgg taaactgccc acttggcagt acatcaagtg tatcatatgc | 600 |
| caagtacgcc ccctattgac gtcaatgacg gtaaatggcc cgcctggcat tgtgcccagt | 660 |
| acatgacctt atgggacttt cctacttggc agtacatcta cgtattagtc atcgctatta | 720 |
| ccatggtcga ggtgagcccc acgttctgct tcactctccc catctccccc cctccccac | 780 |
| ccccaatttt gtatttattt attttttaat tattttgtgc agcgatgggg gcggggggg | 840 |
| gggggggcg gggcgagggg cggggcgggg cgaggcggag aggtgcggcg gcagccaatc | 900 |
| agagcggcgc gctccgaaag tttccttta tggcgaggcg gcggcggcgg cggccctata | 960 |
| aaaagcgaag cgcgcggcgg gcgggagtcg ctgcgcgctg ccttcgcccc gtgccccgct | 1020 |
| ccgccgccgc ctcgcgccgc ccgccccggc tctgactgac cgcgttactc ccacaggtga | 1080 |
| gcgggcggga cggcccttga cggccttct cctcaggtta cagtctcaag cttcgccatg | 1140 |
| tacatggccc ttcagtgtac atggatgggc gggttggtaa ctaaaagacc ctttactcaa | 1200 |
| taaagtagat gatcatgata aatgagggac ggcccttctc ctccgggctg taattagctg | 1260 |
| agcaagaggt aagggtttaa gggatggttg gttggtgggg tattaatgtt taattacctg | 1320 |
| gagcacctgc ctgaaatcac ttttttttcag gttggaccgg tgccaccatg gactataagg | 1380 |
| accacgacgg agactacaag gatcatgata ttgattacaa agacgatgac gataagatgg | 1440 |
| ccccaaagaa gaagcggaag gtcggtatcc acggagtccc agcagccgac aagaagtaca | 1500 |
| gcatcggcct ggacatcggc accaactctg tgggctgggc cgtgatcacc gacgagtaca | 1560 |
| aggtgcccag caagaaattc aaggtgctgg gcaacaccga ccggcacagc atcaagaaga | 1620 |
| acctgatcgg agccctgctg ttcgacagcg gcgaaacagc cgaggccacc cggctgaaga | 1680 |
| gaaccgccag aagaagatac accagacgga gaaccggat ctgctatctg caagagatct | 1740 |
| tcagcaacga gatggccaag gtggacgaca gcttcttcca cagactggaa gagtccttcc | 1800 |
| tggtggaaga ggataagaag cacgagcggc accccatctt cggcaacatc gtggacgagg | 1860 |
| tggcctacca cgagaagtac cccaccatct accacctgag aaagaaactg gtggacagca | 1920 |
| ccgacaaggc cgacctgcgg ctgatctatc tggccctggc ccacatgatc aagttccggg | 1980 |
| gccacttcct gatcgagggc gacctgaacc ccgacaacag cgacgtggac aagctgttca | 2040 |
| tccagctggt gcagacctac aaccagctgt tcgaggaaaa ccccatcaac gccagcggcg | 2100 |
| tggacgccaa ggccatcctg tctgccgac tgagcaagag cagacggctg gaaaatctga | 2160 |
| tcgcccagct gcccggcgag aagaagaatg gcctgttcgg aaacctgatt gccctgagcc | 2220 |
| tgggcctgac ccccaacttc aagagcaact tcgacctggc cgaggatgcc aaactgcagc | 2280 |

```
tgagcaagga cacctacgac gacgacctgg acaacctgct ggcccagatc ggcgaccagt   2340
acgccgacct gtttctggcc gccaagaacc tgtccgacgc catcctgctg agcgacatcc   2400
tgagagtgaa caccgagatc accaaggccc ccctgagcgc ctctatgatc aagagatacg   2460
acgagcacca ccaggacctg accctgctga agctctcgt gcggcagcag ctgcctgaga   2520
agtacaaaga dattttcttc gaccagagca gaacggcta cgccggctac attgacggcg   2580
gagccagcca ggaagagttc tacaagttca tcaagcccat cctggaaaag atggacggca   2640
ccgaggaact gctcgtgaag ctgaacagag aggacctgct gcggaagcag cggaccttcg   2700
acaacggcag catcccccac cagatccacc tgggagagct gcacgccatt ctgcggcggc   2760
aggaagattt ttacccattc ctgaaggaca ccgggaaaa gatcgagaag atcctgacct   2820
tccgcatccc ctactacgtg ggccctctgg ccaggggaaa cagcagattc gcctggatga   2880
ccagaaagag cgaggaaacc atcacccct ggaacttcga ggaagtggtg acaagggcg   2940 cttccgccca gagcttcatc gagcggatga ccaacttcga taagaacctg cccaacgaga   3000
aggtgctgcc caagcacagc ctgctgtacg agtacttcac cgtgtataac gagctgacca   3060
aagtgaaata cgtgaccgag ggaatgagaa agcccgcctt cctgagcggc gagcagaaaa   3120
aggccatcgt ggacctgctg ttcaagacca accggaaagt gaccgtgaag cagctgaaag   3180
aggactactt caagaaaatc gagtgcttcg actccgtgga aatctccggc gtggaagatc   3240
ggttcaacgc ctccctgggc acataccacg atctgctgaa aattatcaag gacaaggact   3300
tcctggacaa tgaggaaaac gaggacattc tggaagatat cgtgctgacc ctgcacactgt   3360 ttgaggacag agagatgatc gaggaacggc tgaaaaccta tgcccacctg ttcgacgaca   3420
aagtgatgaa gcagctgaag cggcggagat acaccggctg gggcaggctg agccggaagc   3480
tgatcaacgg catccgggac aagcagtccg gcaagacaat cctggatttc ctgaagtccg   3540
acggcttcgc caacagaaac ttcatgcagc tgatccacga cgacagcctg accttttaaag   3600 aggacatcca gaaagcccag gtgtccggcc agggcgatag cctgcacgag cacattgcca   3660
atctggccgg cagccccgcc attaagaagg gcatcctgca gacagtgaag gtggtggacg   3720
agctcgtgaa agtgatgggc cggcacaagc ccgagaacat cgtgatcgaa atggccagag   3780
agaaccagac cacccagaag ggacagaaga cagccgcga gaatgaag cggatcgaag   3840 agggcatcaa agagctgggc agccagatcc tgaaagaaca cccgtggaa acacccagc   3900 tgcagaacga gaagctgtac ctgtactacc tgcagaatgg gcgggatatg tacgtggacc   3960
aggaactgga catcaaccgg ctgtccgact acgatgtgga ccatatcgtg cctcagagct   4020
ttctgaagga cgactccatc gacaacaagg tgctgaccag aagcgacaag aaccggggca   4080
agagcgacaa cgtgccctcc gaagaggtcg tgaagaagat gaagaactac tggcggcagc   4140
tgctgaacgc caagctgatt acccagagaa agttcgacaa tctgaccaag gccgagagag   4200
gcggcctgag cgaactggat aaggccggct tcatcaagag acagctggtg gaaacccggc   4260
agatcacaaa gcacgtggca cagatcctgg actccggat gaacactaag tacgacgaga   4320
atgacaagct gatccgggaa gtgaaagtga tcacccctgaa gtccaagctg gtgtccgatt   4380
tccgaaagga tttccagttt tacaaagtgc gcgagatcaa caactaccac cacgcccacg   4440
acgcctacct gaacgccgtc gtgggaaccg ccctgatcaa aaagtaccct aagctggaaa   4500
gcgagttcgt gtacggcgac tacaaggtgt acgacgtgcg gaagatgatc gccaagagcg   4560
agcaggaaat cggcaaggct accgccaagt acttcttcta cagcaacatc atgaactttt   4620
```

```
tcaagaccga gattaccctg gccaacggcg agatccggaa gcggcctctg atcgagacaa    4680
acggcgaaac cggggagatc gtgtgggata agggccggga ttttgccacc gtgcggaaag    4740
tgctgagcat gccccaagtg aatatcgtga aaagaccga ggtgcagaca ggcggcttca     4800
gcaaagagtc tatccggccc aagaggaaca gcgataagct gatcgccaga aagaaggact    4860
gggaccctaa gaagtacggc ggcttcgtta gccccaccgt ggcctattct gtgctggtgg    4920
tggccaaagt ggaaaagggc aagtccaaga aactgaagag tgtgaaagag ctgctgggga    4980
tcaccatcat ggaaagaagc agcttcgaga agaatcccat cgactttctg gaagccaagg    5040
gctacaaaga agtgaaaaag gacctgatca tcaagctgcc taagtactcc ctgttcgagc    5100
tggaaaacgg ccggaagaga atgctggcct ctgcccggtt cctgcagaag ggaaacgaac    5160
tggccctgcc ctccaaatat gtgaacttcc tgtacctggc cagccactat gagaagctga    5220
agggctcccc cgaggataat gagcagaaac agctgtttgt ggaacagcac aagcactacc    5280
tggacgagat catcgagcag atcagcgagt ctccaagag agtgatcctg gccgacgcta    5340
atctggacaa agtgctgtcc gcctacaaca gcaccgggga taagcccatc agagagcagg    5400
ccgagaatat catccaccctg tttaccctga ccaatctggg agcccctcgg gccttcaagt    5460
actttgacac caccatcgac cggaaggtgt accggagcac caaagaggtg ctggacgcca    5520
ccctgatcca ccagagcatc accggcctgt acgagacacg gatcgacctg tctcagctgg    5580
gaggcgacaa aaggccggcg ccacgaaaa aggccggcca ggcaaaaaag aaaaagtaag    5640
aattcctaga gctcgctgat cagcctcgac tgtgccttct agttgccagc catctgttgt    5700
ttgcccctcc cccgtgcctt ccttgaccct ggaaggtgcc actcccactg tccttttccta    5760 ataaaatgag gaaattgcat cgcattgtct gagtaggtgt cattctattc tggggggtgg    5820
ggtggggcag gacagcaagg gggaggattg ggaagagaat agcaggcatg ctggggagcg    5880
gccgcaggaa cccctagtga tggagttggc cactccctct ctgcgcgctc gctcgctcac    5940
tgaggccggg cgaccaaagg tcgcccgacg cccgggcttt gcccgggcgg cctcagtgag    6000
cgagcgagcg cgcagctgcc tgcaggggcg cctgatgcgg tattttctcc ttacgcatct    6060
gtgcggtatt tcacaccgca tacgtcaaag caaccatagt acgcgccctg tagcggcgca    6120
ttaagcgcgg cgggtgtggt ggttacgcgc agcgtgaccg ctacacttgc cagcgcctta    6180
gcgcccgctc ctttcgcttt cttcccttcc tttctcgcca cgttcgccgg ctttccccgt    6240
caagctctaa atcgggggct ccctttaggg ttccgattta gtgctttacg gcacctcgac    6300
cccaaaaaac ttgatttggg tgatggttca cgtagtgggc catcgccctg atagacggtt    6360
tttcgccctt tgacgttgga gtccacgttc tttaatagtg actcttgtt ccaaactgga    6420 acaacactca actctatctc gggctattct tttgatttat aagggatttt gccgatttcg    6480
gtctattggt taaaaatga gctgatttaa caaaaattta acgcgaattt taacaaaata    6540
ttaacgttta caattttatg gtgcactctc agtacaatct gctctgatgc cgcatagtta    6600
agccagcccc gacacccgcc aacacccgct gacgcgccct gacgggcttg tctgctcccg    6660
gcatccgctt acagacaagc tgtgaccgtc tccgggagct gcatgtgtca gaggttttca    6720
ccgtcatcac cgaaacgcgc gagacgaaag gcctcgtga tacgcctatt tttataggtt    6780
aatgtcatga taataatggt ttcttagacg tcaggtggca cttttcgggg aaatgtgcgc    6840 ggaacccta tttgtttatt tttctaaata cattcaaata tgtatccgct catgagacaa    6900
taaccctgat aaatgcttca ataatattga aaaaggaaga gtatgagtat caacatttc    6960 cgtgtcgccc ttattccctt ttttgcggca ttttgccttc ctgtttttgc tcacccagaa    7020
```

```
acgctggtga aagtaaaaga tgctgaagat cagttgggtg cacgagtggg ttacatcgaa      7080
ctggatctca acagcggtaa gatccttgag agttttcgcc ccgaagaacg ttttccaatg      7140
atgagcactt ttaaagttct gctatgtggc gcggtattat cccgtattga cgccgggcaa      7200
gagcaactcg gtcgccgcat acactattct cagaatgact tggttgagta ctcaccagtc      7260
acagaaaagc atcttacgga tggcatgaca gtaagagaat tatgcagtgc tgccataacc      7320
atgagtgata acactgcggc caacttactt ctgacaacga tcggaggacc gaaggagcta      7380
accgcttttt tgcacaacat gggggatcat gtaactcgcc ttgatcgttg ggaaccggag      7440
ctgaatgaag ccataccaaa cgacgagcgt gacaccacga tgcctgtagc aatggcaaca      7500
acgttgcgca aactattaac tggcgaacta cttactctag cttcccggca acaattaata      7560
gactggatgg aggcggataa agttgcagga ccacttctgc gctcggccct tccggctggc      7620
tggtttattg ctgataaatc tggagccggt gagcgtggaa gccgcggtat cattgcagca      7680
ctggggccag atggtaagcc ctcccgtatc gtagttatct acacgacggg gagtcaggca      7740
actatggatg aacgaaatag acagatcgct gagataggtg cctcactgat taagcattgg      7800
taactgtcag accaagttta ctcatatata ctttagattg atttaaaact tcatttttaa      7860
tttaaaagga tctaggtgaa gatcctttt gataatctca tgaccaaaat cccttaacgt      7920
gagttttcgt tccactgagc gtcagacccc gtagaaaaga tcaaaggatc ttcttgagat      7980 ccttttttc tgcgcgtaat ctgctgcttg caaacaaaaa aaccaccgct accagcggtg      8040
gtttgtttgc cggatcaaga gctaccaact ctttttccga aggtaactgg cttcagcaga      8100
gcgcagatac caaatactgt tcttctagtg tagccgtagt taggccacca cttcaagaac      8160
tctgtagcac cgcctacata cctcgctctg ctaatcctgt taccagtggc tgctgccagt      8220
ggcgataagt cgtgtcttac cgggttggac tcaagacgat agttaccgga taaggcgcag      8280
cggtcgggct gaacggggggg ttcgtgcaca cagcccagct tggagcgaac gacctacacc      8340
gaactgagat acctacagcg tgagctatga gaaagcgcca cgcttcccga agggagaaag      8400
gcggacaggt atccggtaag cggcagggtc ggaacaggag agcgcacgag ggagcttcca      8460
gggggaaacg cctggtatct ttatagtcct gtcgggtttc gccacctctg acttgagcgt      8520
cgatttttgt gatgctcgtc aggggggcgg agcctatgga aaaacgccag caacgcggcc      8580 ttttacggt tcctggcctt ttgctggcct tttgctcaca tgt                         8623

<210> SEQ ID NO 58
<211> LENGTH: 367
<212> TYPE: DNA
<213> ORGANISM: Artificial Sequence
<220> FEATURE:
<223> OTHER INFORMATION: Synthetic Polynucleotide

<400> SEQUENCE: 58
ggagtcgctg cgcgctgcct tcgccccgtg ccccgctccg ccgccgcctc gcgccgcccg       60
ccccggctct gactgaccgc gttactccca caggtgagcg ggcgggacgg cccttgacgg      120
cccttctcct caggttacag tctcaagctt cgccatgtac atggcccttc agtgtacatg      180
gatgggcggg ttggtaacta aaagaccctt tactcaataa agtagatgat catgataaat      240
gagggacggc ccttctcctc cgggctgtaa ttagctgagc aagaggtaag ggtttaaggg      300
atggttggtt ggtggggtat taatgtttaa ttacctggag cacctgcctg aaatcacttt      360
ttttcag                                                                367
```

<210> SEQ ID NO 59
<211> LENGTH: 2263
<212> TYPE: DNA
<213> ORGANISM: Artificial Sequence
<220> FEATURE:
<223> OTHER INFORMATION: Synthetic Polynucleotide

<400> SEQUENCE: 59

| | | | | | |
|---|---|---|---|---|---|
| atggaggaga | acaatcagaa | ccagtgtatc | ccgtacaatt | gtctgagcaa | tccggaagaa | 60 |
| gttctgctgg | atggcgaacg | catctcaact | ggtaactcat | caattgacat | ctctctctca | 120 |
| cttgttcagt | tcttggtttc | taactttgtg | ccaggaggag | gattccttgt | tggacttatc | 180 |
| gacttcgttt | ggggaatcgt | tggaccttct | caatgggatg | catttctcgt | tcagatcgaa | 240 |
| cagctcatca | acgaaagaat | cgctgagttc | gctaggaatg | ctgctattgc | taaccttgaa | 300 |
| ggacttggaa | acaacttcaa | catctacgtg | gaggcattca | aggaatggga | agaagatcct | 360 |
| aacaacccag | caaccaggac | cagagtgatc | gataggttcc | gtatccttga | tggacttctt | 420 |
| gaaagggaca | ttcctagctt | taggatctct | ggatttgaag | ttccacttct | ctctgtttac | 480 |
| gctcaagctg | ctaatctcca | tcttgctatc | cttagagatt | ctgtgatctt | cggagaaaga | 540 |
| tggggattga | caaccatcaa | cgtgaacgag | aactacaaca | gactcatcag | gcacatcgat | 600 |
| gagtacgctg | atcactgtgc | taacacttac | aaccgtggac | tcaacaacct | tcctaagtct | 660 |
| acctatcaag | attggatcac | atacaaccga | cttaggagag | accttacatt | gactgttctt | 720 |
| gatatcgctg | ctttctttcc | aaactatgac | aataggagat | atccaattca | gccagttggt | 780 |
| caacttacaa | gggaagttta | cactgaccca | ctcatcaact | caacccaca | gcttcagtct | 840 |
| gttgctcagc | ttcctacctt | caacgttatg | gagagcagcg | caatcagaaa | tcctcacctc | 900 |
| ttcgacatct | tgaacaacct | tacaatcttt | accgattggt | ttagtgttgg | acgtaacttc | 960 |
| tactggggag | acatcgact | gatctctagc | ctcatcggag | gtggtaacat | cacatctcct | 1020 |
| atctacggaa | gagaggctaa | ccaggagcct | ccaagatcat | tcactttcaa | cggacctgtg | 1080 |
| ttcaggactc | tttcaaatcc | tactcttcga | cttcttcagc | aaccttggcc | agctccacca | 1140 |
| ttcaaccttc | gtggtgttga | aggagttgag | ttctctacac | ctacaaacag | cttcacctat | 1200 |
| cgtggaagag | gtactgttga | ttctcttact | gaacttccac | ctgaggacaa | cagtgtgcca | 1260 |
| cctcgtgaag | gatacagtca | tcgtctttgt | catgcaacct | tcgttcaaag | atctggaaca | 1320 |
| cctttcctta | caactggtgt | gtgttctct | tggactcatc | gtagtgcaac | tcttaccaac | 1380 |
| acaattgatc | cagagaggat | caaccagatc | cctcttgtga | aaggattcag | agtttgggga | 1440 |
| ggaacctctg | tgattacagg | accaggattc | acaggaggtg | atatccttcg | aagaaacacc | 1500 |
| tttggtgact | cgtttctct | tcaagtgaac | atcaactcac | caatcaccca | aagataccgt | 1560 |
| cttagatttc | gttacgcttc | tagtagggat | gcacgagtta | tcgttcttac | aggagctgca | 1620 |
| tctacaggag | tgggaggtca | agttagtgtg | aacatgcctc | ttcagaaaac | tatggagatc | 1680 |
| ggagagaacc | tcacatctag | aacattcaga | tacaccgact | tcagtaatcc | tttctcattc | 1740 |
| agagctaatc | cagacatcat | cggtatcagt | gaacaacctc | tcttcggtgc | aggttctatc | 1800 |
| agtagcggtg | aactttacat | cgacaagatc | gagatcatcc | ttgcagatgc | aacatttgaa | 1860 |
| gcagaatctg | accttgaaag | agcacaaaag | ggagtcgctg | cgcgctgcct | tcgccccgtg | 1920 |
| ccccgctccg | ccgccgcctc | gcgccgcccg | cccggctct | gactgaccgc | gttactccca | 1980 |
| caggtgagcg | ggcgggacgg | cccttgacgg | cccttctcct | caggttacag | tctcaagctt | 2040 |
| cgccatgtac | atggcccttc | agtgtacatg | gatgggcggg | ttggtaacta | aaagaccctt | 2100 |

```
tactcaataa agtagatgat catgataaat gagggacggc ccttctcctc cgggctgtaa      2160
ttagctgagc aagaggtaag ggtttaaggg atggttggtt ggtggggtat taatgtttaa      2220
ttacctggag cacctgcctg aaatcacttt ttttcagtag tga                       2263
```

<210> SEQ ID NO 60
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 60

```
agtatttgca taaccctgag                                                   20
```

<210> SEQ ID NO 61
<211> LENGTH: 545
<212> TYPE: DNA
<213> ORGANISM: Artificial Sequence
<220> FEATURE:
<223> OTHER INFORMATION: Synthetic Polynucleotide

<400> SEQUENCE: 61

```
cacgtggtgt gagtcctcat aaatgcttac tggtttgaag ggcaacaaaa tagtgaacag        60
agtgaaaatc cccactaaga tcctgggtcc agaaaaagat gggaaacctg tttagctcac       120
ccgtgagccc atagttaaaa ctctttagac aacaggttgt ttccgtttac agagaacaat       180
aatattgggt ggtgagcatc tgtgtggggg cttcaggtgt tacagtctct agcttcgcca       240
tgtacatggc ccttctgtgt acatggatgg gcggggaggt aactaaaaga ccctttacac       300
aataaagtag atgatcatga taaatgagct ttaggtttgg ggtgggatag gggatacggg       360
gagagtggag aaaaagggga cacagggtta atgtgaagtc caggatcccc ctctacattt       420
aaagttggtt taagttggct ttaattaata gcaactctta agataatcag aattttctta       480 acctttagc cttactgttg aaaagccctg tgatcttgta caaatcattt gcttcttggc        540
acgtg                                                                  545
```

<210> SEQ ID NO 62
<211> LENGTH: 1896
<212> TYPE: DNA
<213> ORGANISM: Artificial Sequence
<220> FEATURE:
<223> OTHER INFORMATION: Synthetic Polynucleotide

<400> SEQUENCE: 62

```
atggaggaga caatcagaa ccagtgtatc ccgtacaatt gtctgagcaa tccggaagaa         60
gttctgctgg atggcgaacg catctcaact ggtaactcat caattgacat ctctctctca       120
cttgttcagt tcttggtttc taactttgtg ccaggaggag gattccttgt tggacttatc       180
gacttcgttt ggggaatcgt tggaccttct caatgggatg catttctcgt tcagatcgaa       240
cagctcatca acgaaagaat cgctgagttc gctaggaatg ctgctattgc taaccttgaa       300
ggacttggaa caacttcaa catctacgtg gaggcattca aggaatggga agaagatcct       360
aacaacccag caaccaggac cagagtgatc gataggttcc gtatccttga tggacttctt       420
gaaagggaca ttcctagctt taggatctct ggatttgaag ttccacttct ctctgtttac       480
gctcaagctg ctaatctcca tcttgctatc cttagagatt ctgtgatctt cggagaaaga       540
tggggattga caaccatcaa cgtgaacgag aactacaaca gactcatcag gcacatcgat       600
```

```
gagtacgctg atcactgtgc taacacttac aaccgtggac tcaacaacct tcctaagtct    660
acctatcaag attggatcac atacaaccga cttaggagag accttacatt gactgttctt    720
gatatcgctg ctttctttcc aaactatgac aataggagat atccaattca gccagttggt    780
caacttacaa gggaagttta cactgaccca ctcatcaact tcaacccaca gcttcagtct    840
gttgctcagc ttcctacctt caacgttatg gagagcagcg caatcagaaa tcctcacctc    900
ttcgacatct tgaacaacct tacaatcttt accgattggt ttagtgttgg acgtaacttc    960
tactggggag gacatcgact gatctctagc ctcatcggag gtggtaacat cacatctcct   1020
atctacggaa gagaggctaa ccaggagcct ccaagatcat tcactttcaa cggacctgtg   1080
ttcaggactc tttcaaatcc tactcttcga cttcttcagc aaccttggcc agctccacca   1140
ttcaaccttc gtggtgttga aggagttgag ttctctacac ctacaaacag cttcacctat   1200
cgtggaagag gtactgttga ttctcttact gaacttccac ctgaggacaa cagtgtgcca   1260
cctcgtgaag gatacagtca tcgtctttgt catgcaacct tcgttcaaag atctggaaca   1320
cctttcctta caactggtgt tgtgttctct tggactcatc gtagtgcaac tcttaccaac   1380
acaattgatc cagagaggat caaccagatc cctcttgtga aaggattcag agtttgggga   1440
ggaacctctg tgattacagg accaggattc acaggaggtg atatccttcg aagaaacacc   1500
tttggtgact tcgtttctct tcaagtgaac atcaactcac caatcaccca aagataccgt   1560
cttagatttc gttacgcttc tagtagggat gcacagagtta tcgttcttac aggagctgca   1620
tctacaggag tgggaggtca agttagtgtg aacatgcctc ttcagaaaac tatggagatc   1680
ggagagaacc tcacatctag aacattcaga tacaccgact tcagtaatcc tttctcattc   1740
agagctaatc cagacatcat cggtatcagt gaacaacctc tcttcggtgc aggttctatc   1800
agtagcggtg aactttacat cgacaagatc gagatcatcc ttgcagatgc aacatttgaa   1860
gcagaatctg accttgaaag agcacaaaag tagtga                             1896
```